United States Patent [19]

Kaper et al.

[11] Patent Number: 5,882,653
[45] Date of Patent: Mar. 16, 1999

[54] VIBRIO CHOLERAE 01 (CVD111) AND NON-01 (CVD112 AND CVD112RM) SEROGROUP VACCINE STRAINS, METHODS OF MAKING SAME AND PRODUCTS THEREOF

[75] Inventors: James B. Kaper; Myron M. Levine, both of Columbia, Md.

[73] Assignee: The University of Maryland System, Baltimore, Md.

[21] Appl. No.: 624,601

[22] PCT Filed: Oct. 7, 1994

[86] PCT No.: PCT/US94/11424

§ 371 Date: Jul. 29, 1996

§ 102(e) Date: Jul. 29, 1996

[87] PCT Pub. No.: WO95/10300

PCT Pub. Date: Apr. 20, 1995

Related U.S. Application Data

[63] Continuation-in-part of Ser. No. 133,438, Oct. 8, 1993, abandoned, and a continuation-in-part of Ser. No. 133,439, Oct. 8, 1993, abandoned, each is a continuation-in-part of Ser. No. 931,943, Aug. 12, 1992, Pat. No. 5,470,729, which is a continuation-in-part of Ser. No. 821,872, Jan. 16, 1992, abandoned, which is a continuation of Ser. No. 533,315, Jun. 5, 1990, abandoned, which is a continuation-in-part of Ser. No. 581,406, Feb. 17, 1984, Pat. No. 5,135,862, which is a continuation-in-part of Ser. No. 472,276, Mar. 4, 1983, abandoned, said Ser. No. 533,315, is a continuation-in-part of Ser. No. 363,383, Jun. 5, 1989, Pat. No. 4,935,364, which is a continuation of Ser. No. 867,633, May 27, 1986, abandoned, which is a continuation of Ser. No. 472,276.

[51] Int. Cl.$^6$ ............................ A61K 39/106; C12N 1/20
[52] U.S. Cl. ................................ 424/261.1; 435/252.3; 435/477; 435/480; 435/909; 536/23.1; 536/23.7; 424/93.2; 424/200.1; 424/235.1
[58] Field of Search ............................ 424/184.1, 200.1, 424/234.1, 236.1, 261.1, 93.1; 435/69.1, 172.1, 172.3, 452.1

[56] References Cited

U.S. PATENT DOCUMENTS

| | | | |
|---|---|---|---|
| 4,264,737 | 4/1981 | Murphy | 435/172 |
| 4,666,837 | 5/1987 | Harford et al. | 435/68 |
| 4,882,278 | 11/1989 | Mekalanos | 435/172.3 |
| 5,631,010 | 5/1997 | Mekalanos | 424/235.1 |

FOREIGN PATENT DOCUMENTS

| | | |
|---|---|---|
| 0018154 | 10/1980 | European Pat. Off. |
| 0095452 | 11/1983 | European Pat. Off. |
| 0119031 | 9/1984 | European Pat. Off. |
| 914286 | 3/1992 | South Africa |
| 2032955 | 5/1980 | United Kingdom |
| WO9118979 | 12/1991 | WIPO |

OTHER PUBLICATIONS

Remamurthy et al (1993) Lancent 341:703–704 "Emergence of novel strain of *Vibrio cholerae* with epidemic potential in southern and eastern India".

James B. Kaper and Myron M. Levine, "Cloned Cholera Enterotoxin Genes In Study and Prevention of Cholera", Nov. 21, 1981, The Lancet, pp. 1162–1163.

B. Diane Gambill, and Anne O. Summers, "Versatile mercury–resistant cloning and expression vectors", 1985, Gene, vol. 39, pp. 293–297.

Alessio Fasano et al., "*Vibrio cholerae* produces a second enterotoxin, which effects intestinal tight junctions", Jun. 1991, Proc. Natl. Acad. Sci. USA, vol. 88, pp. 5242–5246.

Yokota, T. et al., "Genetic Behavior of R Factors in *Vibrio cholerae*", *J. of Bacteriology,* vol. 109, Jan. 1972. pp. 440–442.

Cuatrecasas, P., "*Vibrio cholerae* Choleragenoid. Mechanism of Inhibition of Cholera Toxin Action", *Biochemistry,* 12, No. 18, 1973, pp. 3577–3581.

Cash, R. et al., "Response Of Man To Infection With *Vibrio cholerae* . . .", *J. Of Infectious Diseases,* vol. 129, No. 1, by Univ. of Chicago, Jan. 1974, pp. 45–52.

Finkelstein, R. et al., "Studies On Toxinogenesis In *Vibrio cholerae* . . .", *J. Of Infectious Diseases,* vol. 129,, No. 2, by Univ. of Chicago, Feb. 1974, pp. 117–123.

Guerrant, R. et al., "Cyclic Adenosine Monophosphate and Alteration Of Chinese Hamster Ovary Cell Morphology . . .", *Infection & Immunity,* vol. 10, No. 2, Aug. 1974, pp. 320–327.

Gill, D., "Involvement of Nicotinamide Adenine Dinucleotide in the Action of Cholera Toxin In Vitro", *Proc. Nat. Acad. Sci. USA,* vol. 72, No. 6, Jun. 1975, pp. 2064–2068.

Southern, E., "Detection of Specific Sequences Among DNA Fragments Separated by Gel Electrophoresis", *J. Mol. Biol.,* vol. 98, (1975), pp. 503–517.

Noriki, H., "Evaluation of Toxoid Field Trial In The Philippines", *Symposium on Cholera Sapporo,* 1976, pp. 302–310.

Levine, M., "Immunity to Cholera as Evaluated In Volunteers", *Cholera and Related Diarrheas,* 43rd Nobel Symp., Stockholm, 1978, pp. 195–203.

Beringer, J. et al., "Transfer Of The Drug–Resistance Transposon Tn5 to Rhizobium", *Nature,* vol. 276, Dec. 7, 1978, pp. 633–634.

Johnson, S. et al., "*Vibrio cholerae* Hybrid Sex Factor That Contains Ampicillin Transposon Tn1", *J. Bacteriology,* Jan. 1979, pp. 531–536.

Honda, T. et al., "Selection And Characteristics Of A *Vibrio cholerae* Mutant . . .", *Proc. Natl. Acad. Sci. USA,* vol. 76, No. 4, Apr. 1979, pp. 2052–2056.

(List continued on next page.)

*Primary Examiner*—Robert A. Wax
*Assistant Examiner*—Nashaat T. Nashed
*Attorney, Agent, or Firm*—Kile McIntyre & Harbin

[57] ABSTRACT

Avirulent *Vibrio cholerae* strains of O1 (CVD111) and non-O1 (CVD112 and CVD112RM) serogroups having the DNA of the cholera toxin core and the RS1 sequences of the cholera toxin locus deleted, and further having a DNA encoding a resistance to mercury, and a DNA encoding the cholera toxin B subunit, or a part thereof sufficient to confer immunogenicity, re-inserted in the chromosome. Methods of making the avirulent *V. cholerae* O1 and non-O1 strains of the invention, and cholera vaccines using these strains.

29 Claims, 29 Drawing Sheets

OTHER PUBLICATIONS

Dallas, W. et al., "Cistrons Encoding *Escherichia Coli* Heat–Labile Toxin", *J. Bacteriology,* vol. 139, No. 3, Sep. 1979, pp. 850–858.

Chilton, M. et al., "Tailoring The Agrobacterium Ti Plasmid As a Vector For Plant Genetic Engineering", *Stadler Symp.,* vol. 13, Univ. of Missouri, 1981, pp. 39–52.

Matzke, A. et al., "Site–Specific Insertion Of Genes Into T–DNA Of The Agrobacterium Tumor–Inducing Plasmid . . . ", *J. of Molecular and Applied Genetics,* vol. 1, No. 1, 1981, pp. 39–49.

Kaper, J. et al., "Molecular Characterization of Environmental and Nontoxigenic Strains of *Vibrio cholerae*", *Infection and Immunity,* vol. 32, No. 2, May 1981, pp. 661, 667.

Sigel, S. et al., "Ability Of An Avirulent Mutant of *Vibrio cholerae* . . . ", *Infection and Immunity,* vol. 32, No. 2, May 1981, pp. 474–479.

Holmgren, J., "Actions Of Cholera Toxin And The Prevention And Treatment Of Cholera", *Nature,* vol. 292, Jul. 30, 1981, pp. 413–417.

Sublett, R. et al., "Transposon–Facilitated Recombination in Classical Biotypes Of *Vibrio cholerae*", *Infection and Immunity,* vol. 32, No. 3, Jun. 1981, pp. 1132–1138.

Thomson, J. et al., "Mutagenesis By Insertion Of Drug Resistance Transposon Tn7 Into A Vibrio Species", *J. Bacteriology,* vol. 148, Oct. 1981, pp. 374–378.

Baudry, B. et al., "Cloning Of A Gene (zot) Encoding A New Toxin Produced By *Vibrio cholerae*", *Infection & Immunity,* vol. 60, No. 2, Feb. 1992, pp. 428–434.

Levine, M. et al., "Volunteer Studies In Development of Vaccines Against Cholera . . . ", *Acute Enteric Infections In Children,* Elsevier/North–Holland Biomedical Press, 1981, pp. 443–459.

Gennaro, M. et al., "The Expression Of Biologically Active Cholera Toxin In *Escherichia coli*", *Nucleic Acids Research,* vol. 10, No. 16, 1982, pp. 4283–4290.

Mekalanos, J. et al., "Isolation Of Enterotoxin Structural Gene Deletion Mutations In *Vibrio cholerae* . . . ", *Proc. Natl. Acad. Sci.* (USA), vol. 79, Jan. 1982, pp. 151–155.

Levine, M. et al., "Immunity Of Cholera In Man: Relative Role Of Antibacterial Versus Antitoxic Immunity", *Transactions Royal Soc. Of Tropical Medicine & Hygiene,* vol. 73, 1979, pp. 3–9.

Svennerholm, A. et al., "Intestinal Antibody Responses After Immunization With Cholera B Subunit", *The Lancet,* Feb. 6, 1982, pp. 305–308.

Boesman–Finkelstein, M. et al., "Protection In Rabbits Induced By The Texas Star–SR Attenuated $A^{-B+}$ Mutant Candidate Live Oral Cholera Vaccine", *Infection and Immunity,* vol. 36, No. 1, Apr. 1982, pp. 221–226.

Pearson, G. et al., "Molecular Cloning Of *Vibrio cholerae* Enterotoxin Genes In *Escherichia coli* K–12", *Proc. Natl. Acad. Sci.* (USA), vol. 79, May 1982, pp. 2976–2980.

Lee, C. et al., "Use Of Cloned mtl Genes of *Escherichia coli* To Introduce mtl Deletion Mutations Into the Chromosome", *J. Bacteriology,* vol. 153, No. 2, Feb. 1983, pp. 685–592.

Mekalanos, J., "Duplication and Amplification Of Toxin Genes In *Vibrio cholerae*", *Cell,* vol. 35, Nov. 1983, pp. 253–263.

Lockman, H. et al., "Nucleotide Sequence Analysis Of The A2 and B Subunits Of *Vibrio cholerae* Enterotoxin", *J. Of Biological Chemistry,* vol. 258, No. 22, Nov. 1983, pp. 13722–13726.

Levine, M. et al., "New Knowledge On Pathogenesis Of Bacterial Enteric Infections As Applied To Vaccine Development", *Microbiological Reviews,* vol. 47, No. 4, Dec. 1983, pp. 510–550.

Mekalanos, J. et al., "Cholera Toxin Genes: Nucleotide Sequence, Deletion Analysis And Vaccine Development", *Nature,* vol. 306, Dec. 8, 1983, pp. 551–557.

Svennerholm, A. et al., "Local And Systemic Antibody Responses And Immunological Memory In Humans . . . ", *Bulletin of World Health Org.,* vol. 62 (6), 1984, pp. 909–918.

Barrineau, P. et al., "The DNA Sequence Of The Mercury Resistance Operon of the IncFII Plasmid NR1", *J. Of Molecular and Applied Genetics,* vol. 2, No. 6, 1984, pp. 253–261.

Sporecke, I. et al., "Genetic Mapping Of *Vibrio cholerae* Enterotoxin Structural Genes", *J. Bacteriology,* vol. 157, No. 1, Jan. 1984, pp. 253–261.

Levine, M. et al., Evaluation In Humans Of Attenuated *Vibrio cholerae* El Tor Ogawa Strain Texas Star–SR . . . , *Infection and Immunity,* vol. 43, No. 2, Feb. 1984, pp. 515–522.

Kaper, J. et al., "Recombinant Nontoxinogenic *Vibrio cholerae* Strains As Attenuated Cholera Vaccine Candidates", *Nature,* vol. 308, Apr. 12, 1984, pp. 655–658.

Lockman, H. et al., "*Vibrio cholerae* Enterotoxin Genes: Nucleotide Sequence Analysis of DNA . . . ", *J. Bacteriology,* vol. 159, No. 3, Sep. 1984, pp. 1086–1089.

Kaper, J. et al., "A Recombinant Live Oral Cholera Vaccine", *Bio/Technology,* vol. 2, Apr. 1984, pp. 345–349.

Brown, N. et al., "The Nucleotide Sequence Of the Mercuric Resistance Operons Of Plamd R100 and Transposon TN501 . . . ", *Mol Gen Genet,* vol. 2, 202, 1986, pp. 143–151.

Black, Robert. et al., "Protective Efficacy In Man Of Killed Whole Vibrio Oral Cholera Vaccine . . . ", *Infection & Immun.* , 1987, 23 pages.

Kaper, J. et al., "Recent Advances In Developing A Safe And Effective Live Oral Attenuated *Vibrio cholerae* Vaccine", *Advan.In Research on Cholera & Related Diarrheas,* vol. 6, 1988, pp. 161–167.

Levine, M. et al., "Volunteer Studies Of Deletion Mutants Of *Vibrio cholerae* O1 Prepared By Recombinant Techniques", *Infection & Immunity,* vol. 56, No. 1., Jan. 1988, pp. 161–167.

Rader, A. et al., "Nucleotide Sequences And Comparison Of The Hemolysin Determinants . . . ", *Infection & Immunity,* vol. 56, No. 6, Jun. 1988, pp. 1414–1419.

Levine, M. et al., "Safety, Immunogenicity, And Efficacy Of Recombinant Live Oral Cholera . . . ", *The Lancet,* Aug. 27, 1988, pp. 467–470.

Migasena, S. et al., "Preliminary Assessment Of The Safety And Immunogenicity Of Live Oral Cholera . . . ", *Infection & Immunity,* vol. 57, Nov. 1989, pp. 3261–3264.

Galen, J. et al., "Cloning, Sequencing, and Expression Of The Gene, nanH, For *Vibrio cholerae* . . . ", *Advances In Research On Cholera and Related Diarrheas,* vol. 7, 1990, pp. 143–153.

Brickman, T. et al., "Molecular Cloning And Nucleotide Sequence Analysis Of Cholera Toxin Genes . . . ", *Infection & Immunity,* vol. 58, No. 12, Dec. 1990, pp. 4142–4144.

Cryz, S. Jr. et al., "Randomized Double–Blind Placebo Controlled Trial To Evaluate The Safety . . . ", *Vaccine,* vol. 8, Dec. 1990, pp. 577–580.

Tacket et al., "Safety and Immunogenicity of Live Oral Cholera Vaccine Candidate CVD 110, a ΔctxA Δzot Δace Derivative of El Tor Ogawa *Vibrio cholerae*", *The Journal of Infectious Diseases,* vol. 168, pp. 1536–1540 (1993).

Michalski et al., "CVD110, an Attenuated *Vibrio cholerae* 01 El Tor Live Oral Vaccine Strain", *Infection and Immunity,* vol. 61, No. 10, pp. 4462–4468 (1993).

Galen et al., "Role of *Vibrio cholerae* Neuraminidase in the Function of Cholera Toxin", *Infection and Immunity,* vol. 60, No. 2, pp. 406–415, Feb. 1992.

| SAMPLE | N | MEAN | S.D. | P |
|---|---|---|---|---|
| 395 | 30 | 244.2 | 107.9 | 0.002 |
| MEDIUM | 14 | 373.7 | 129.0 | |
| CVD101 | 32 | 230.2 | 75.5 | 0.004 |
| MEDIUM | 30 | 305.8 | 96.3 | |
| 395N1 | 31 | 305.8 | 80.1 | 0.322 |
| MEDIUM | 31 | 289.1 | 83.8 | |

FIG. 14

```
  1  ATACAGCGGCTTTCTGTTCTTTTTAGGGTTAGACCAAGGCGCTGGCTATCGTGCTTCAGGC

M  S  I  F  I  H  H  G
     TTTGATGACCCGTTTCGCCCTGCGAGCGTTAAACCTATGAGTATCTTTATTCATCACGGC 120

A  P  G  S  Y  K  T  S  G  A  L  N  L  R  L  L  P  A  I  K
 121  GCGCCAGGCTCTTATAAAACGTCCGGGGCATTATGGCTTCGTCTGCTGCCGGCGATTAAG

S  G  R  H  I  I  T  N  V  R  G  L  N  L  E  R  I  A  K  Y
      TCAGGGCCGTCACATCATCACGAATGTGCGAGGGCTTAAACCTTGAACGCATAGCTAAGTAC 240

L  K  M  D  V  S  D  I  S  I  E  F  I  D  T  D  H  P  D  G
 241  TTAAAAATGGACGTCTCAGACATCAGTATCGAGTTTATTGATACAGACCATCCAGACGGT

R  L  T  M  A  R  F  W  H  W  A  R  K  D  A  F  L  F  I  D
      CGGCTTAACGATGGCGCGTTTTTGGCACTGGGCACGGAAAGGACGCGTTTCTCTTTATTGAT 360

E  C  G  R  I  N  P  P  R  L  T  A  T  N  L  K  A  L  D  T
 361  GAATGTGGTCGCATCAATCTGCCGCGACTTGCCGAGACTAACCTGAAGGCTCTCGACACG

P  P  D  L  V  A  E  D  R  P  E  S  P  E  V  A  F  D  M  H
      CCGCCGGATTTGGTCGCAGAGGATAGGCCTGAGAGCTTTGAGGTCGCTTTTGACATGCAT 480

R  H  H  G  W  D  I  C  L  T  P  N  I  A  K  V  H  N  M
 481  CGTCACCACGGCTGGGATATCTGCCTAACCACGCCTAACATTGCCAAAGTGCACAACATG

I  R  E  A  A  E  I  G  Y  R  H  F  N  R  A  T  V  G  L  G
      ATAAGAGAGGCGGCGGAGATAGGCTATCGCCACTTTAACCGCGCCACGGTGGGGCTAGGG 600

A  K  F  L  T  L  I  H  D  A  A  N  S  G  Q  M  D  S  H  A
 601  GCAAAGTTTACCCTGACCACCACCCAGATGCAGCCAACTCTGGACAGATGGATTCGCACGCG

L  T  R  Q  V  K  K  I  P  S  P  I  F  K  M  Y  A  S  T
      CTGACACGCCAAGTCAAAAAATTCCAAGTCCGATTTTTAAGATGTACGCAAGCACCACC 720
```

FIG. 17A

```
       T  G  K  A  R  D  T  M  A  G  T  A  L  W  K  D  R  K  I  L
 721   ACAGGGCAAAGCACGGCGACACGGATGGCCGGAACGGCTCTGTGGAAAGACAGAAAGATCCTT

F  L  F  G  M  V  F  L  M  F  S  Y  S  F  Y  G  L  H  D  N
 841   TTCTTGTTCGGCATGGTTTTTTTGATGTTCTCTTATTCGTTTTACGGCTTACACGACAAT   840

P  I  F  T  G  G  N  D  A  T  I  E  S  E  Q  S  H  P  Q  S
 841   CCAATTTTTACAGGGGGAAATGATGCAACTATCGAGTCAGAGCAATCCGAGCCTCAGTCA

K  A  T  A  G  N  A  V  G  S  K  A  A  P  A  S  F  G  F      960
 961   AAGGCTACTGCTGGGAATGCTGTCGGGAGCAAGGCGGCTGCTCCTGCTTCTTTTGGTTTT

C  I  G  R  L  C  V  Q  D  G  F  V  T  V  G  D  E  R  Y  R
1081   TGTATTGGTCGGCTTTGTGTCCAAGATGGTTTTGTCACTGTTGGTGATGAGCGTTATCGC

L  V  D  N  L  D  I  P  Y  R  G  L  W  A  T  G  H  I  I  Y  1080
1081   CTCGTAGACAATTTGGACATTCCTTATCGTGGTCTATGGGCGACAGGTCATCACATTTAC

K  D  T  L  T  V  F  F  E  T  E  S  G  S  V  P  T  E  L  F
1201   AAGGATACGCTTACAGTGTTTTTTGAAACCGAGAGTGGCAGCGTCCCAACAGAGCTGTTT   1200

A  S  S  Y  R  Y  V  L  P  P  D  F  N  H  F  V  V  F
1201   GCATCGAGCTACCGCTACGTGCTACCGGATTTCAATCACTTTGTGGTGTTC

D  T  F  A  A  Q  A  L  W  E  V  K  R  G  L  P  I  K  T
1201   GATACCTTTGCAGCGCAAGCGCTGTGGGTAGAAGTGAAACGGGGTTTACGGATAAAAACA   1320

E  N  D  K  K  G  L  N  S  I  F  *
1201   GAAAATGATAAAAAAGGACTAAATAGTATATTTTGATTTTTGATTTTTGATTTTTGATTT

1321   TTGATTTTTGATTTTTGATTTTCAAATAATACAAATTTATTTACTTATTTAATT
       GTTTTGATCAATTATTTTCTGTTAAACAAGGGAGCATTATATGGTA   1428
```

FIG. 17B

```
  1  GATATCCACTCACGCATTAAGTGGGCTCGTCGTCAGGTCGGTAAGACGTTGTTTGATATT
                A
 61  TCAAAGCATTTTGGTGGTGATTTGGAAAGGGTGTTTGGGCGTTGATTTCTAAGGAAATT   120
121  CACGACGATTCACTCAACCTTCCAGATTCTTATATGAAGTTAATTGATGAAATTATGGGT  180
181  GATTAATATGAAATCTCGTTTTGTTTTTTGGTGCCTCTCATTCTGAAGGGGTG---AG    240
                                                        AGT
241  TAAGACTGGTGCTCCTTATCCCAGTGCTTTTTGTTGGTAAGCCGATTCGCCAGTG       300
              A  T
301  GAAAAACGATAAAGGCCAATGTTTGACGTTTGGCTTGCAGCATCAGGAAGTGAAATTTGT  360
361  ATCCAGTGACGCGATGACCAGAAAACTCGAACAGACCGCCTTTCCGGTTCTTGTCACGTT  420
421  TGACAATGAGCCAGAGACCCAGAAGACCCATCGCGTAACCTCGTGATTGATTATCAAGTGGT 480
                                       A  C
481  GTGTTCCTTGTTTGACAACGTGCCGGGCGCAAGCCATTGGATAAACCTCAACCCATTAAA  540
                                A
541  TCTTGATGGACTTAACCCATTATGTCTGGAGGCGCTCTATTTCGCGGGTGGTCAAGG     600
              A
```

FIG. 22A

```
601  CCGTTCTCGTTCTGTTCTTTACATCCTTTGGGATTGGGCGCGGTTGCCAGTCTCATTTTAT   660
                                                              T
661  CCACGGTAAAGGAGAAGCTACACATGTTAGCTCACTGAAAAACAAACTTAATACCTTTAAA  720
721  AGCACCCTTTCACTCGGGGTTTTCTTGCTGTGTTTTCCGCATTTGCTAACCAAGCACTCGCG  780
         G
781  GCTGCTGATACGGGTTTGGTCGCGGAAGTCACCAAAACACTGGGCACCAGTAAAGATACG   840
                A                                          C
841  GTGATTGCGCTTGGGCCGCTTATCATGGGCGTGGTGGGAGCAATTGTTCTGATTGTTACC   900
                                          G
901  GTGATTGGCTTAATTCGTAAGGCTAAAATAGTGCTTGAGTTGTGGCTGGGTCTCTTTGGCT  960
961  CAGCGGTCATCATTATCGGCTTTGTGTCGGGCTTATATATTTGGTTTAAGGGAGGAGGGCGA 1020
                M   R   Y   F   L   F   L   T   L   F   L   S   P
1021 GCGTTCGCCCCTTTTTTATGCGCTATTTCTACTGTTTTGACATTGCTCTTTCTTTCTTCTCC 1080
      S   V   T   A   S   S   I   N   C   D   P   N   T   T   S   H   Q   L   L
1081 ATCGGTAACAGCTTCCTCCATCAATTGTGATCCTAATACTACGTCACACCAGTTACT     1140
         G
                                                               G
      F   G   F   G   S   P   I   V   Q   S   V   L   F   D   G   C   M   L   D   I
1141 TTTCGGTTTTGGCTCTCCCATTGTGCAATCGGTGTTATTTGATGGCTGCATGCTTGATAT   1200
```

FIG. 22B

```
              E  K  D  D  Y  G  F  V  W  S  C  L  S  N  E  N  G  D  Y  C
1201  TGAAAAAGATGACTATGGTTTTGTTTGGTCTCTGTCTCTCAAATGAAAATGGGGACTATTG  1260

K  G  L  Y  K  P  R  F  T  Q  G  V  S  P  N  W  P  M  C  D
1261  CAAGGGGCTCTACAAACCCCGTTTTACACAAGGGGTGTCCCCGAACTGGCCGATGTGCGA   1320
                                       A

L  S  G  A  S  A  E  R  C  I  Y  P  Y  C  P  E  G  E  E  C
1321  CTTGTCCGGAGCATCTGCAGAGCGCTGCATTTATCCTTATTGCCCTGAGGGGGAAGAGTG   1380
                        T

V  P  L  P  P  S  P  P  S  D  S  P  V  D  G  L  S  S  S  F
1381  CGTTCCCTTACCACCTTCACCGCCCAGTGATTCCCCAGTGGATGGGCTGAGCAGCTCGTT   1440

K  S  A  F  N  Q  V  Y  K  N  Q  S  E  M  A  S  T  L  N  H
1441  TAAGTCTGCGTTCAATCAGGTCTATAAAAACCAATCAGAGATGGCTTCGACTCTCAATCA   1500

V  S  G  Q  V  S  H  S  Q  D  M  V  Q  L  N  T  K  F  H  A
1501  TGTCAGTGGTCAGGTGTCCCACTCTCAAGATATGGTTCAGCTCAATACGAAGTTTCACGC   1560

D  R  V  L  E  K  V  N  A  I  N  N  R  L  N  G  Q  I  N  Y
1561  GGACCGTGTTCTTGAAAAAGTGAACGCAATCAATAACCGATTGAATGGGCAGATAAACTA   1620
                                             T           GG    A   GG G

L  E  E  V  R  I  D  V  W  D  T  Q  R  E  V  R  K  A  K  D
1621  TCTTGAAGAAGTTCGCATCGATGTATGGGATACACAAAGGGAAGTCAGAAAAGCCAAGGA   1680
                        G    AC       T   T   G           A
```

FIG. 22C

```
       E  L  S  S  R  V  G  S  V  A  H  D  V  Y  Q  S  K  N  A  V
1681  TGAACTCTCTTCACGTGTTGGTTCTGTTGCACGATGTTTACCAAAGTAAGAATGCTGT   1740
                  G  T AC     T       CGG      T       GCTTT  T   CG   CT AA

L  R  A  I  D  E  L  K  D  S  L  G  G  V  V  P  P  N  P
1741  GCTTCGGGGCGATTGATGAGCTTAAAGATTCACTCGGTGGGTGTCGTTCCGCCTAACCC   1800
         C                       A                                 AC

D  Q  P  N  P  T  P  P  D  S  S  P  N  Y  T  G  A  L  N
1801  AGACCAACCCAATCCCACGCCACCTGATAGCAGCCCCAATTATACAGGGGCGCTTAA    1860

T  I  S  K  K  L  N  T  L  E  T  I  S  Q  Q  L  D  T  M  N
1861  TACCATCTCTAAAAAGCTCAATACCTTAGAGACGATTTCACAGCAACTCGACACCATGAA   1920

T  A  L  S  G  R  C  S  N  P  A  R  C  Q  F  P  I  R  E  A
1921  CACGGCGCTATCAGGGCGCTGTAGTAACCCTGCTCGTGTCAGTTTCCGATACGGCGAGGC   1980
                                                          AA              A

E  T  E  L  E  T  A  Q  Q  N  L  K  Q  M  I  N  D  K  I  T
1981  CGAGACCGAGTTAGAAACGGCTCAGCAGAATTTAAAGCAGATGATCAACGATAAAATCAC   2040
                                                                    G

Q  S  A  L  H  Q  F  K  G  S  A  A  V  P  S  F  C  S  Y  V
2041  CCAGTCGGCTTTGCATCAGTTCAAAGGCTCGGCGGCCGTGCCTTCGTTTTGCTCCTATGT   2100

E  E  F  G  Y  N  L  C  F  D  F  S  L  F  S  E  N  L  H  I
2101  CGAGGAGTTTGGTTACAACCTCTGTTTTGACTTCTCCCTCTTTTCTGAAAACCTGCACAT   2160
                         C
```

FIG. 22D

```
         I   R   M   I   V   L   A   M   A   Y   I   L   A   A   M   L   I   L   F   R
2161  CATCCGCATGATAGTGCTCGCGATGGCGTACATTCTGGCCGCCATGCTCATTTGTTTAG       2220

M   L   M   M   D   P   L   Y   D   W   L   I   D   G   F   T   W   L   V
2221  GTGATGCTTATGATGGACCCCTTATGACTGGCTAATTGATGGCTTTACGTGGCTTGTG       2280
                                A

I   K   L   G   I   M   W   N   I   E   S   K   I   F   V   I   Q   F   F   W   E
2281  ATCAAGCTCGGTATTATGTGGATTGAGAGCAAGATTTTTGTCATCCAATTCTTCTGGGAG      2340
                                                            T

M   S   Q   K   V   I   D   M   F   T   I   Y   P   L   I   Q   Q   A   I   D
2341  ATGTCCCAGAAAGTGATTGATATGTTTACCATCTATCCGCTTATCCAACAGGCTATCGAT      2400

M   L   S   P   Q   Y   S   G   F   L   F   F   L   G   L   D   Q   A   L   A
2401  ATGCTGTCTCCTCAATACAGCGGCTTTCTGTTCTTTTTAGGGTTAGACCAAGCGCTGGCT      2460
                      C

I   V   L   Q   A   L   M   T   R   F   A   L   R   A   L   N   L
2461  ATCGTGCTTCAGGCTTTGATGACCCGTTTCGCCCTGCGAGCGTTAAACCTATGAGTATCT      2520
                                        T

2521  TTATTCATCACGGCGGCCCAGGCTCTTATAAAACGTCCGGGCATTATGGCTTCGTCTGC       2580
                                                            A

2581  TGCCGGCGATTAAGTCAGGCCGTCACATCATCACGAATGTGCGAGGCTTAAACCTTGAAC      2640

2641  GCATAGCTAAGTACTTAAAAAATGGACGTCTCAGACATCAGTATCGAGTTTATTGATACAG    2700
         G                                   T   G
```

FIG. 22E

```
2701  ACCATCCAGACGGTCGCTTAACGATGGCGCGTTTTTGGCACTGGGCGAGAAAGGACGCGT  2760
                  T
2761  TTCTCTTTATTGATGAATGTGGTCGCATCTGGCCCGAGACTGACGGCCACCAATTTAA    2820
                           C                                  T
2821  AGGCGCTCGACACGCCGCCGGATTTGGTCGCAGAGGATAGGCCTGAGAGCTTTGAGGTGG  2880
2881  CTTTTGACATGCATCGTCACCACGGCTGGGATATC                           2915
```

FIG. 22F

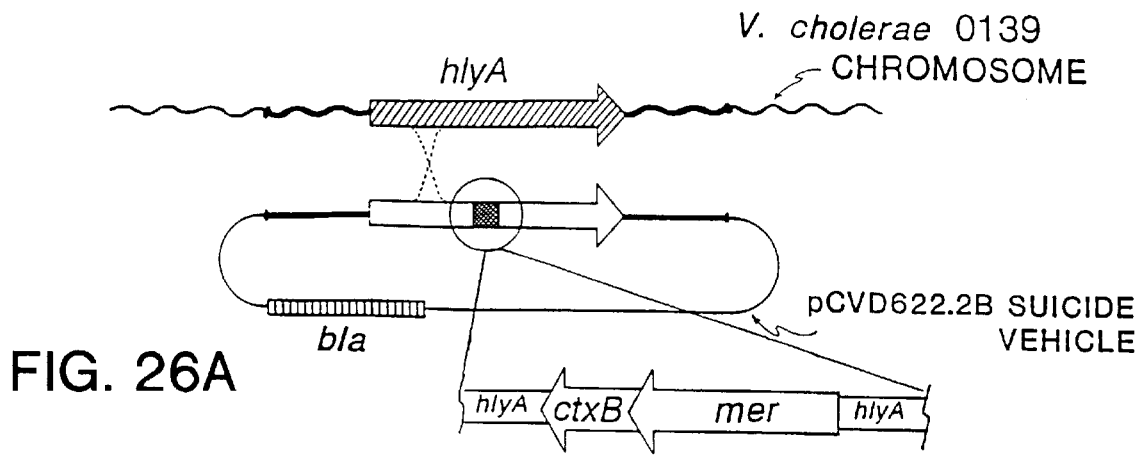
FIG. 26A
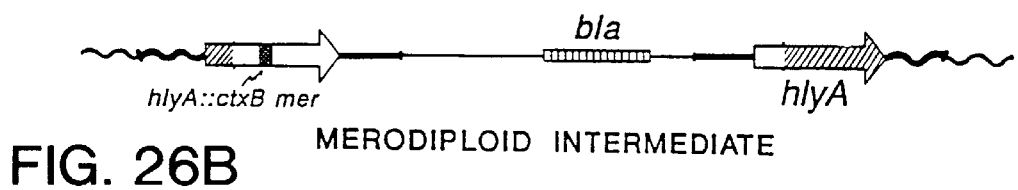
FIG. 26B  MERODIPLOID INTERMEDIATE
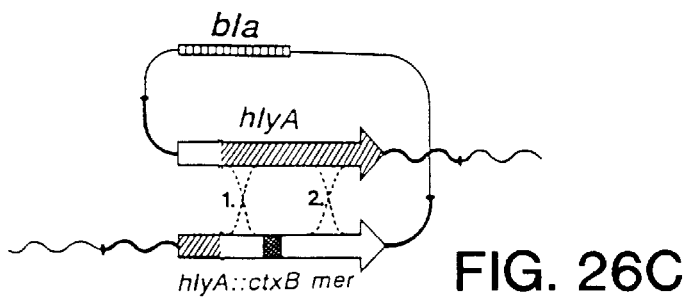
FIG. 26C
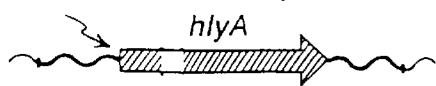
1837.2
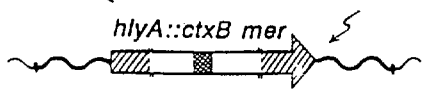
CVD112
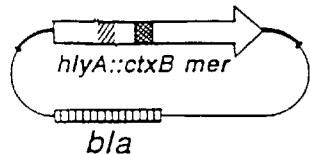 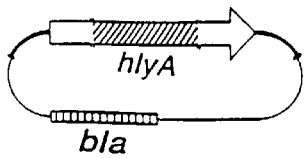
FIG. 26D VIBRIO CHOLERAE 01 (CVD111) AND NON-01 (CVD112 AND CVD112RM) SEROGROUP VACCINE STRAINS, METHODS OF MAKING SAME AND PRODUCTS THEREOF This application is a continuation-in-part of U.S. patent applications Ser. Nos. 08/133,438 and 08,133/439, both of which were filed on Oct. 8, 1993, and are now abandoned the contents of which are incorporated herein by reference. Both U.S. patent applications Ser. Nos. 08/133,438 and 08/133, 439 are continuation-in-parts of U.S. patent application Ser. Nos. 07/931,943, filed Aug. 12th, 1992, which issued as U.S. Pat. No. 5,470,729 on Nov. 29, 1995, which is a continuation-in-part of applicants' U.S. patent application Ser. No. 07/821,872, filed Jan. 16, 1992, now abandoned which is a continuation of U.S. patent application Ser. No. 07/533,315, filed Jun. 5th, 1990, now abandoned which is incorporated herein by reference. U.S. patent application Ser. No. 07/533,315 is a continuation-in-part of applicants' U.S. patent application Ser. No. 06/581,406 filed Feb. 17th, 1984 which issued as U.S. Pat. No. 5,135,862, on Aug. 4, 1992, which is a continuation-in-part of U.S. patent application Ser. No. 06/472,276, filed Mar. 4th, 1983, now abandoned, each of which are incorporated herein by reference. U.S. patent application Ser. No. 07/533,315 is also a continuation-in-part of applicant's U.S. patent application Ser. No. 07/363,383, filed Jun. 5th, 1989 and issued as U.S. Pat. No. 4,935,364 on Jun. 19, 1990, which is a continuation of U.S. patent application Ser. No. 06/867,633, filed May 27th, 1986, now abandoned, which is a continuation of U.S. patent application Ser. No. 06/472,276, filed Mar. 4th, 1983 now abandoned, each of which are incorporated herein by reference. The research detailed in this application was supported by the National Institute of Health and in part by the Medical Biotechnology Center of the Maryland Biotechnology Institute.

BACKGROUND OF THE INVENTION

*Vibrio cholerae* (*V. cholerae*) is a non-invasive enteropathogen of the small bowel that does not penetrate the mucosal surface. Local SIga mediated immunity at the mucosal surface is therefore implicated as a protective mechanism. Pathogenic *V. cholerae* 01 elaborate a protein enterotoxin (also know as cholera enterotoxin, or choleragen, or cholera toxin) which is responsible for induction of copious secretion by the intestine resulting in watery diarrhea, the clinical consequence of cholera infection. The genes responsible for cholera enterotoxin are the ctx genes (also known as the tox genes). Cholera diarrhea can be extraordinarily severe and result in loss of so much body water and salts that dehydration, acidosis, shock, and death ensue without prompt therapy. There is known in the region of the *V. cholerae* chromosome containing the ctx genes that multiples copies of a 2700 base pair sequence called RS1 (for repetitive sequence) can be found. Mekalanos, *Cell* 35, 253–263 (1983).

Applicants have also discovered that a second enterotoxin is produced by *V. cholerae* which has been named zonula occludens toxin, reported in Fasano et al, Vibrio cholerae Produces a Second enterotoxin Which Affects Intestinal Tight Junctions, Proc. Nat. Acad. Sci. (USA) 88, 5242–5246 (1991).

The cholera vaccines that have been developed can be broadly divided into two categories; those aiming to stimulate antitoxic immunity and those intending to induce antibacterial immunity. Experiments with animal models support a protective role for either or both antitoxic and antibacterial immunity. It has been suggested that when both types of immunity work in unison, there is a synergistic effect. [Holmgren, J. et al. *J. Infect. Dis.* 136 Suppl., S105–S1122 (1977); Peterson, J. W. *Infect. Immun.* 26, 594 (1979); Resnick, I. G. et al. *Infect. Immun.* 13, 375 (1980); Svennerholm, A.-M. et al. *Infect. Immun.* 13, 735 (1976)]. However, it appears that protective immunity in humans can be conferred without such synergistic effect, that is by either antitoxic immunity or antibacterial immunity [Eubanks, E. R. et al. *Infect. Immun.* 15, 533 (1977); Fujita, K. et al. *J. Infect. Dis.* 125, 647 (1972); Holmgren, J., *J. Infect. Dis.*, supra; Lange, S. et al. *Acta Path. Microbiol. Scand Sect. C* 86, 145 (1978); Peterson, J. W., supra (1979); Pierce, N. F. et al. *Infect Immun.* 37, 687 (1982); Pierce, N. F. et al. *Infect. Immun.* 21, 185 (1978); Pierce, N. F. et al. *J. Infect. Dis.* 135, 888 (1977); Resnick, I. G. et al., supra; Svennerholm, A.-M. et al, supra].

KILLED WHOLE CELL VACCINES

1. Parenteral Whole Cell Vaccines

For almost a century, killed whole *V. cholerae* have been employed as parenteral vaccines; these vaccines are still commercially available. Experience with the parenteral whole cell vaccines has been reviewed in Joo, I. "Cholera Vaccines." In Cholera. (Barua D. and Burrows W., eds.), Saunders, Philadelphia, pp. 333–355 (1974) and in Feeley, J. D. et al. In *Cholera and Related Diarrheas.* 43rd Nobel Symp., Stockholm 1978. (O. Oucherlong, J. Holmgren, eds.) Karger, Basel, pp. 204–210 (1980). Such vaccines stimulate high titers of serum vibriocidal antibodies. They also stimulate increases in intestinal Siga antibody to *V. cholerae* somatic 0 antigen when given to Pakistanis but not to Swedes [Svennerholm, A.-M. et al. Infect. Immun. 30., 427 (1980); Svennerholm, A.-M. et al. *Scan. J. Immun.* 6, 1345 (1977)]. It has been suggested that the Pakistani vaccine recipients respond in this way because they are already immunologically primed from prior antigenic contact, while persons living in a non-endemic area (e.g., Sweden) are not. In field trials parenteral killed whole cell vaccines have been shown to confer significant protection against the homologous *V. cholerae* serotype, but usually for a period of less than one year [Joo, I. supra; Feeley, J. C. supra; Svennerholm, A.-M. et al. supra, (1980); Svennerholm, A.-M. et al. supra, (1977); Mosley, W. H. et al. *Bull. Wld. Hlth. Org.* 49, 13 (1973); Philippines Cholera Committee, *Bull. Wld. Hlth. Org.* 49, 381 (1973)]. There is some evidence to suggest that parenteral whole cell Inaba vaccine provides good, short term protection against Ogawa, as well as against Inaba cholera, while Ogawa vaccine is effective only against Ogawa.

By use of adjuvants, it has been possible to maintain a vaccine efficacy of approximately 70% for up to one-and-one-half years with parenteral vaccine (see, e.g., Saroso, J. S. et al. *Bull. Wld. Hlth. Org.* 56, 619 (1978)). However, the adverse reactions encountered at the site of inoculation with adjuvanted vaccines (which include sterile abscesses) are sufficiently frequent and severe to preclude routine use of such adjuvanted vaccines.

2. Oral Whole Cell Vaccines

Killed whole vibrios administered orally stimulate the appearance of local intestinal anti-vibrio antibody. [Freter, R. *J. Infect Dis.* 111, 37 (1972); Freter R. et al. *J. Immunol.* 91 724 (1963); Ganguly, R. et al. *Bull. Wld. Hlth. Org.* 52, 323 (1975)]. Other investigators have shown substantial vaccine efficacy, but a large proportion of the vaccines developed diarrhea after subsequent challenge with pathogenic vibrios [Cash, R. A. et al. *J. Infect. Dis.* 130, 325 (1974)].

TOXOIDS

Immunizing agents intended to prevent cholera by means of stimulating antitoxic immunity include:
1) Formaldehyde-treated cholera toxoid
2) Glutaraldehyde-treated cholera toxoid;
3) Purified B subunit; and
4) Procholeragenoid (with or without formaldehyde treatment).

1. Formaldehyde-Treated Cholera Toxoid

Treatment of purified cholera toxin in vitro with formaldehyde eradicates its toxicity, resulting in a toxoid that exhibits little toxic biological activity but stimulates antitoxic antibodies following parenteral immunization of animals. However, when the first toxoid of this type was administered to either monkeys or man as a parenteral vaccine, the toxoid reverted to partial toxicity causing unacceptable local adverse reactions at the site of inoculation [Northrup, R. S. et al. *J. Infect. Dis.* 125, 471 (1972)]. An aluminum-adjuvanted formalinized cholera toxoid has been administered parenterally to Bangladeshi volunteers, including lactating mothers, but no field trials with this vaccine have been undertaken [Merson, M. H. et al. *Lancet* I, 931 (1980)]. Formalinized cholera toxoid prepared in the presence of glycine has also been tried by the parenteral route, but the vaccine showed no evidence of efficacy [Ohtomo, N. In *Proceedings of the 12th Joint Conference on Cholera*, U.S.-Japan Cooperative Medical Science Program, Sapporo (Fukumi H., Zinnaka Y., eds.) pp. 286–296 (1976); Noriki, H. In *Proceedings of the 12th Joint Conference on Cholera*, U.S.-Japan Cooperative Medical Science Program, Sapporo (Fukumi H., Zinnaka Y., eds.) pp. 302–310 (1976)].

2. Glutaraldehyde-Treated Cholera Toxoid

Methods have been developed for the large-scale preparation of a glutaraldehyde-treated cholera toxoid that is essentially free of contaminating somatic antigen [Rappaport, E. S. et al. *Infect. Immun.* 14, 687 (1976)]. It was hoped that this antigen could be used to assess in a "pure" manner the protective role of antitoxic immunity alone. A large-scale field trial of this toxoid given as a parenteral vaccine was carried out in Bangladesh in 1974 [Curlin, G. et al. In *Proceeding of the 11th Joint Conference on Cholera*, U.S.-Japan Cooperative Medical Science Program. pp. 314–329, New Orleans, (1975)]. The toxoid stimulated high titers of circulating antitoxins in Bangladeshi recipients. Two waves of cholera, El Tor Inaba followed by El Tor Ogawa, struck the field area allowing a fair evaluation of vaccine efficacy. A protective effect could be demonstrated in only one age group and was restricted to the period of the Inaba epidemic, so that glutaraldehyde-treated cholera toxoid given alone as a parenteral vaccine provided little protection and was substantially inferior to similar field trials in the same population with parenteral killed whole cell vaccines.

The use of glutaraldehyde-treated cholera toxoid as an oral vaccine has been investigated on the assumption that toxoid given by this route might be more efficient by stimulating intestinal antitoxin antibodies[Levine, M. M. et al. *Trans. Roy. Soc. Trop. Med. Hyg.* 73, 3, (1979)]. Two groups of volunteers were immunized with three 2.0 mg, or three 8.0 mg doses of toxoid given directly into the small intestinal lumen (via intestinal tube) at monthly intervals. The vaccinees and unimmunized controls then participated in experimental cholera challenge studies. In neither challenge study was the attack rate or severity of diarrhea significantly diminished in the vaccines when compared with controls. The lack of efficacy of oral glutaraldehyde-treated cholera toxoid may be due to the fact that the capacity of B subunits to bind to GM1 ganglioside is greatly diminished as a consequence of toxoiding with glutaraldehyde.

3. Purified B Subunit

Cholera enterotoxin is composed of two subunits designated A and B, encoded by the ctxAB operon. The A subunit induces the enzymatic changes which lead to fluid secretion, while the non-toxic B subunit is the immunogenic moiety that binds to the receptor for toxin (GM1 ganglioside) on intestinal epithelial cells [Holmgren, J. *Nature* 292, 413 (1981)]. It has been shown that purified B subunit given either orally or parenterally to Bangladeshis stimulates the appearance of Siga antitoxin in intestinal fluid, a result attributable to immunological priming in a cholera-endemic area [Svennerholm, A.-M. et al. *Lancet* I, 305 (1982)].

The major advantages of B subunit oral vaccine to stimulate antitoxic immunity include its complete safety (there is not potential for reversion to toxin as exists with toxoids) and retention of its capacity to adhere to toxin receptors on enterocytes. Animal studies suggest, however, that the purified B subunit is less potent than native holotoxin in stimulating antitoxin antibodies [Pierce, N. F. supra, (1982)].

It will be understood that the purified B subunit can be used, if at all, in conjunction with e.g. oral killed vibrios as a combination oral vaccine intended to stimulate both antibacterial and antitoxic antibodies.

4. Procholeragenoid

Procholeragenoid is the large molecular weight toxoid (ca. 1,000,000 MW) that results when cholera enterotoxin is heated at 65° C. for at least five minutes [Finkelstein, R. A. et al. *J. Immunol.* 107, 1043 (1971)]. It is immunogenic while retaining less that 5% of the biological toxic activity of the parent toxin. Heating for longer times (e.g., 25 minutes) produces less biological toxicity [Germanier, R. et al. *Infect. Immun.* 13, 1692 (1976)], and subsequent treatment with formaldehyde completely abolishes residual biological toxicity. The resultant formaldehyde-treated procholeragenoid is at least as potent as the parent toxin in stimulating serum antitoxin following immunization of rabbits. Swiss volunteers developed brisk serum antitoxin responses following parenteral immunization with 10, 30, or 100 mcg doses of formaldehyde-treated procholeragenoid [Germanier, R. et al. *J. Infect. Dis.* 135. 512 (1977)]. No notable adverse reactions were observed.

As an oral antigen procholeragenoid is more immunogenic when given in the form without formaldehyde-treatment. In dogs, untreated procholeragenoid is tolerated as well as an oral vaccine; oral doses (with $NaHCO_3$ carrier) up to 500 mcg do not case diarrhea. Five 500 mcg doses spaced over 42 days stimulate significant protection in dogs against oral challenge with pathogenic *V. cholerae*. Doses of 50 mcg and 200 mcg with $NaHCO_3$ have been given to groups of six and four adult volunteers, respectively, without eliciting adverse reactions.

It will be understood that pro-choleragenoid can be used in conjunction with e.g., live vaccines, killed vibrios or other relevant antigens capable of stimulating antibacterial immunity so that the antitoxic immunity induced by procholeragenoid is enhanced.

COMBINATION VACCINES

The major attraction of non-living, oral cholera vaccine is its safety. An oral vaccine consisting of a combination of antigens, intending to stimulate both antibacterial and antitoxic immunity, would be most likely to succeed for the following reasons: Toxoid vaccines that stimulate purely antitoxic immunity have not been shown to be efficacious in protecting man against cholera, although they may protect animal models. In addition, oral or parenteral killed whole cell vaccines that stimulate no antitoxic immunity provide significant protection against cholera in man, albeit for a short period of time. Furthermore, combinations of antigens (such as crude cholera toxin, or toxin plus lipopolysaccharide) that stimulate both antitoxic and antibacterial immunity, give synergistic protection.

Two studies so far have been carried out in many with combination vaccines. In the first, nine volunteers who ingested glutaraldehyde-treated cholera toxoid (2 mg weekly for four weeks) plus killed El Tor Inaba vibrios ($10^{10}$ vibrios twice weekly for four weeks) were challenged, along with six unimmunized controls, after one month with $10^6$ pathogenic El Tor Inaba vibrios. Diarrhea occurred in only two of nine vaccines, versus four of six controls (vaccine efficacy 67%) and illness was clearly attenuated in the two ill vaccinees. More pertinent, perhaps, is the observation that *V. cholerae* could be directly cultured from stools of only two of nine vaccinees, versus six of six controls. This demonstrates that immunologic mechanisms impeded the proliferation of vibrios.

In another study, three doses of B subunit/killed whole cell combination vaccine was given to adult volunteers who participated in a vaccine efficacy challenge. The combination vaccine was given on days 0, 14, and 28. Each of the three doses of vaccine contained 0.5 mg of purified B subunit and $2 \times 10^{11}$ killed *V. cholerae* ($5 \times 10^{10}$ classical Inaba, $5 \times 10^{10}$ classical Ogawa, and $1 \times 10^{11}$ El Tor Inaba).

A group of eleven volunteers immunized with this combination vaccine were challenged one month after their last dose with $10^6$ pathogenic *V. cholerae* El Tor Inaba, along with seven control volunteers. Diarrhea occurred in seven of seven controls, but in only four of eleven vaccinees (p=0.01). The illness in the four vaccinees was definitely milder.

Thus, results of studies with oral toxoid/killed whole cell vaccine combinations demonstrate a measurable degree of efficacy. The protective vaccine efficacy, however, is only moderate (55–65%) and multiple doses are required to induce the protection.

ATTENUATED *V. CHOLERAE* VACCINES

Both classical and El Tor clinical cholera infections stimulate a high degree of protective immunity for at least three years in North American volunteers [Cash, R. A. et al., supra (1974); Levine, M. M. et al. supra (1979); Levine, M. M. et al. "Volunteers studies in development of vaccines against cholera and enterotoxigenic *Escherichia coli*: a review," in *Acute Enteric Infections in Children: New Prospects for Treatment and Prevention*. (T. Holm, J. Holmgren, M. Merson, and R. Mollby, eds.) Elsevier, Amsterdam, pp. 443–459 (1981); and Levine, M. M. et al. *J. Infect. Dis.* 143, 818 (1981)]. Based on these observations in volunteers, perhaps the most promising approach toward immunologic control of cholera may be with attenuated non-toxigenic *V. cholerae* strains employed as oral vaccines.

1. Naturally-Occurring *V. cholerae* O1 Strains

Non-toxigenic *V. cholerae* O1 serogroup strains isolated from environmental sources in India and Brazil have been evaluated in volunteers as potential vaccine candidates with disappointing results. They either failed to colonize the intestine of man, or did so minimally; vibriocidal antibody responses were meager, and they failed to provide protection in experimental challenge studies [Cash, R. A. et al. *Infect.* *Immun.* 10, 762 (1974); Levine M. M. et al. *J. Infect. Dis.* 145, 296 (1982)]. Many of these strains appear to lack the toxin gene, as measured by hybridization with a radioactive DNA probe [Kaper, J. B. et al. *Infect. Immun.* 32, 661 (1981)].

2. Mutagenized Attenuated Strains

Classical Inaba 569B has been mutagenized with nitrosoguanosine (NTG) and hypotoxinogenic mutant isolated [Finkelstien, R. A. et al. *J. Infect. Dis.* 129, 117 (1974); Holmes, R. K. et al. *J. Clin. Invest.* 55, 551 (1975). This mutant strain, M13, was fed to volunteers. Diarrhea did not occur but the strain colonized poorly. Challenge studies demonstrated that some protective efficacy was conferred by immunization with multiple doses [Woodward, E. et al. *Develop. Biol. Stand.* 33, 108, (1976)].

El Tor Ogawa 3083 has also been mutagenized [Honda, T. et al. *Proc. Nat. Acad. Sci.* 76, 2052 (1979)]. Brute force selection and analysis of thousands of colonies yielded one isolate that continued to produce the immunogenic B subunit while failing to produce detectable A subunit or holotoxin. The one isolate, Texas Star-SR, fulfilled these criteria. Texas Star-SR produces normal or increased amount of B subunit but is negative in assays for holotoxin activity or A subunit activity.

Texas Star-SR has been extensively evaluated in volunteers (see, e.g., Levine M. M. et al. *Acute Enteric*, supra (1981)). Groups of five volunteers received two $10^9$ organism doses one week apart and eighteen more volunteers ingested two $2\times10^{10}$ organism doses one week apart. Some degree of diarrhea was seen in sixteen of the sixty-eight vaccinees (24%). In only one individual did the total stool volume exceed 1.0 liter (1464 ml). Typically, the vaccine-induced diarrhea consisted of two or three small, loose stools totalling less than 400 ml in volume. Vaccine organisms were recovered from co-procultures of approximately one-half of the vaccine recipients. Where jejunal fluid was cultured (recipients of doses of $10^8$ or more vaccine organisms), cultures were positive in thirty-five of forty-six vaccines (76%). Hundreds of Texas Star clones recovered from co-procultures and jejunal fluid cultures were examined for cholera holotoxin by the sensitive Y-1 adrenal cell assay; none were positive.

Significant rises in serum antitoxin were detected in only 29% of the vaccinees; however, 93% manifested significant rises in serum vibriocidal antibody and the titers were substantially close to those encountered following infection with pathogenic *V. cholerae*. In experimental challenge studies in volunteers, Texas Star-SR was found to confer significant protection against challenge with both EL Tor Ogawa And El Tor Inaba vibrios. One or two doses of Texas Star-SR attenuated oral vaccine confers good protection against El Tor cholera.

It is clear that the use of attenuated strains has intrinsic advantages since such strains mimic infection-derived immunity to cholera. However, the Texas Star-SR strains suffers from certain drawbacks. To begin with, mutagenesis (e.g., with nitrosoguanosine) induces multiple mutations, not all of which are necessarily recognized. Furthermore, the precise genetic lesion that is presumed to be responsible for the attenuation of Texas Star-SR is not known. In addition, as with any pathogen mutated with nitrosoguanosine, Texas Star-SR may revert to virulence.

3. Naturally-Occurring *V. cholerae* non-O1 Strains

*V. cholerae* of the O1 serotype is generally responsible for epidemic cholera. The non-O1 serogroup has been associated mainly with sporadic cases of gastroenteritis and extraintestinal infections, but has not previously had epidemic potential. Recently, however, several strains of *V. cholerae* isolated from a typical cholera-like outbreaks have been obtained. [Ramamurthy et al., *The Lancet*, vol. 341, 703–704 (1993), the entire contents of which are incorporated herein by reference.] Serological characterization of a large number of strains isolated in this recent outbreak showed that they failed to agglutinate with O1 antiserum nor with any of tested monoclonal antibodies raised against factor A, B or C of O1 serogroup *V. cholerae*. As a result, these vibrios have been identified as non-O1.

Furthermore, with the exception of one non-O1 strain tested as above, all other non-O1 strains tested in a particular new outbreak could not be typed in the panel of 138 antigens developed for *V. cholerae* non-O1 serogroup at the Japanese National Institutes of Health, indicating that the strain associated with this new outbreak belong to a previously unrecognized, or recently emergent, non-O1 serotype capable of causing epidemic cholera.

Upon DNA hybridization analysis, all of the strains from this outbreak hybridized with both ctx- and zot-specific probes, but none hybridized with a DNA probe specific for the heat-stable enterotoxin of *V. cholerae* non-O1 (NAG-ST). Additionally, production of cholera toxin was apparently detected by an enzyme-linked immunosorbent assay. The amount of enterotoxin produced by these newly isolate strains has been reported to be similar to that produced in clinical strains of *V. cholerae* O1. Most of these strains have also been reported to be resistant to, for example, streptomycin and furazolidone, but sensitive to other commonly used antibiotics including tetracycline. Resistance to ampicillin, or its derivatives, was not reported.

In another recent outbreak, although the overall number of cholera cases did not increase, a large majority of the *V. cholerae* isolates from cholergic diarrhoeal patients screened were non-O1, and as in the previous isolates, could not be typed by standard typing tests.

In another reported case of a non-O1 associated, potentially epidemic cholera outbreak has been reported which primarily has been affecting adults [Albert et al., *The Lancet*, vol. 341, 704 (1993), the entire contents of which are incorporated herein by reference]. Of the rectal swabs obtained in this report, about 67 percent yielded *V. cholerae* non-O1 upon standard testing, and none were reported to test as *V. cholerae* O1.

The *V. cholerae* responsible for this outbreak has been reported to resemble *V. cholerae* O1 both biochemically and in colony morphology, but was reported to not agglutinate *V. cholerae* antisera. The *V. cholerae* strains tested were non-reactive with a monoclonal antibody specific for the A factor of *V. cholerae* O1.

In this second recently reported outbreak, all non-O1 strains tested were reported as positive for the production of cholera toxin in the sensitive Y-1 adrenal cell assay, and were reported to be neutralized by rabbit polyclonal antiserum to cholera toxin. Polymerase chain reaction analysis using O1 cholera toxin-specific primers was also reported to amplify cholera toxin sequences. Selected isolates were also analyzed by the rabbit intestinal illeal loop assay and were reported to perfuse watery diarrhea in the reverse illeal loop tie similar to that due to *V. cholerae* O1.

The *V. cholerae* strain of this second outbreak were reported to be sensitive to certain antibiotics, including tetracycline, but were resistant to other vibriostatic compounds. Such a result contrasts to the susceptibility of currently prevalent strains in the area, the majority of which isolates are resistant to tetracycline.

Due to these outbreaks of *V. cholerae* non-O1 outbreaks, it would be highly desirable to produce vaccines specific for these organisms. In addition, it would also be highly desirable to produce combination vaccines that are effective against both O1 and non-O1 organisms, particularly for use in those region where virulent strains of both *V. cholerae* serogroups may be encountered.

SUMMARY OF THE INVENTION

Applicants of the present invention have made, by novel methods, and isolated mutants of a virulent strain of *Vibrio cholerae* of the O1 and non-O1 serotype, said mutants being suitable for use as a vaccine for protection against the symptoms of cholera upon challenge by virulent *V. cholerae* strains. The starting strain for the making the one mutant of the present invention is *V. cholerae* strain 1837, which is a non-O1 strain of the O139 serogroup. The mutants contain deletions in the *V. cholerae* enterotoxin core region, which deletions were made using restriction endonucleases of a newly identified, characterized and cloned core region of the ctx locus of the starting strain, although other suitable methods of deletion known in the art could also be used.

In order to induce immunogenicity, sequences encoding the cholera toxin B subunit were re-introduced in the vaccine strain. Also introduced into the mutant strains were sequences which encode resistance to heavy metals, for example mercury, and which allow for the identification of the presence of the vaccine strain without the use of potentially therapeutically useful antibiotic markers.

The *V. cholerae* non-O1 vaccine strains of the present invention have thus been specifically altered through the use of recombinant DNA techniques to render the strains avirulent without affecting other components necessary for immunity.

One avirulent non-O1 *V. cholerae* of the invention is *V. cholerae* CVD112 (cep$^-$, zot$^-$, ace$^-$, orfU$^-$, ctxA$^-$, ctxB, mer, hylA$^-$, attRS1$^-$, RS1$^-$). Another avirulent *V. cholerae* non-O1 of the invention is *V. cholerae* CVD112RM (cep$^-$, zot$^-$, ace$^-$, orfU$^-$, ctxA$^-$, ctxB, mer, hylA$^-$, recA$^-$ attRS1$^-$, RS1$^-$).

A characterization of a virulent *V. cholerae* non-O1 ctx locus was undertaken, leading to the new finding that the strain isolated contained two core regions and four repetitive sequences (RS1 sequences). A plasmid is constructed in which there is a deletion in all, or substantially all, of the cholera toxin core region, but retaining extensive lengths of flanking DNA repetitive sequence of the *V. cholerae* chromosome at the ctx locus (i.e., the ctx genetic element). Conjugal gene transfer of this plasmid into a virulent *V. cholerae* non-O1, followed by homologous recombination and a second recombination event yielded a *V. cholerae* non-O1 with only a single core sequence and a single RS1 repetitive element. The remaining core sequence and RS1 element were subsequently removed using newly cloned, and then deleted, O139 chromosomal DNA. Sequences encoding the cholera toxin B subunit and sequences encoding a resistance to heavy metals were subsequently re-introduced into the mutant *V. cholerae* chromosome by homologous recombination.

The non-O1, nontoxigenic deletion mutants of the invention are capable of colonizing the small intestine and stimulating local, protective immunity directed against the bacterial cell. After the transient colonization episode, the vaccine is protective against subsequent infection with virulent toxigenic *V. cholerae* non-O1 strains.

The invention also provides for methods of making avirulent *V. cholerae* non-O1 strains, and vaccines derived from these strains, including combination vaccines.

The genes for *V. cholerae* O1 serogroup cholera toxin have been cloned [Pearson, G. D. N. et al. *Prod. Nat. Acad. Sci.* 79, 2976 (1982); Kaper, J. B. et al.*Amer. Soc. Micribiol. Abstr. Annu. Meeting.* Atlanta, Ga., 36 (1982); Kaper, J. B. et al. *Symposium on Enteric Infections in Man and in Animals: Standardization of Immunological Procedures*, Dublin, Ireland, Abstract No. 2.5 (1982)]. Toxin structural gene deletion mutants of *V. cholerae* have been isolated, but only by infection with mutagenic vibriophages capable of integration at random sites along to chromosome [Mekalanos, J. J. et al. *Proc. Nat. Acad. Sci.* 79, 151, (1982)]. Recombination in *Vibrio cholerae* has been reported, but it has not been used to isolate deletions in the ctx genes for vaccination purposes [Parker, C. et al. *J. Bact.* 112, 707 (1972); Johnson, S. R. et al. *Molec. Gen. Genet.* 170, 93 (1979); Sublett, R. D. et al. *Infect. Immun.* 32 1132 (1981) and Thomson J. A. et al. *J. Bact.* 148, 374 (1981)].

Avirulent *Vibrio cholerae* strain of the O139 serotype (*V. cholerae* 1837), mutated to have a region of chromosomal DNA deleted to confer avirulence and to retain capacity to colonize the intestine of a host animal, while still conferring immunogenicity is described herein. The DNA fragment deleted includes all, or substantially all of the cholera toxin core region. One isolated deletion mutant encompasses all elements associated with the ctx locus, and therefore has no core or repetitive sequences (RS1) elements. Sequences encoding the cholera toxin B subunit and sequences encoding a resistance to heavy metals were re-introduced into this deletion mutant. An additional mutant in the recA gene is also described. Inactivation of the recA gene product in this strain removes a potential mechanism for homologous recombination in this vaccine strain.

A first avirulent non-O1 *V. cholerae* deletion mutant of the cholera toxin core and RS1 sequences of non-O1 *Vibrio cholerae* is described, as is a method of making this *V. cholerae* comprising the steps of (a) constructing a first plasmid comprising DNA of the *Vibrio cholerae* cholera toxin core region and flanking sequences of sufficient length to promote detectable in vivo recombination, ligated to a gene encoding a first selectable marker of foreign origin which confers resistance to a selective agent, wherein said first plasmid is incapable of replicating extrachromosomally in *V. cholerae;*

(b) mating a virulent strain of *Vibrio cholerae* of a non-O1 serogroup with a first microorganism carrying the first plasmid;

(c) selecting for and isolating *Vibrio cholerae* expressing the first selectable marker;

(d) growing the *V. cholerae* isolated in step (c) in the absence of said selective agent;

(e) screening the *V. cholerae* of step (d) for the loss of expression of said first selectable marker;

(f) constructing a second plasmid comprising *Vibrio cholerae* non-O1 chromosomal sequences which flank the cholera toxin locus, deleted of DNA of the cholera toxin core and RS1 sequences, ligated to a second selectable marker of foreign origin which confers resistance to a second selective agent;

(g) mating the selected product of step (e) with a second microorganism carrying said second plasmid; and (h) selecting for *Vibrio cholerae* which express the second selectable marker;

(i) growing the selected product of step (h) in the absence of the second selective agent;

(j) screening the *V. cholerae* of step (i) for the loss of said second selectable marker; and (k) isolating the screened product of step (j).

The product of the first method of the invention is a non-O1 *V. cholerae* deleted of all cholera toxin core sequences and the RS1 elements associated with the ctx locus.

A second avirulent, non-O1 *V. cholerae* according to the invention, which has a deletion of the cholera toxin core and RS1 sequences but expresses re-inserted sequences of the cholera toxin B subunit, or a part thereof sufficient to confer immunogenicity, and sequences encoding a product which confers resistance to heavy metals is also described, as is a method of making this second non-O1 vaccine strain. This second method of the invention comprises the steps of (a) providing a first plasmid comprising DNA of the *Vibrio cholerae* cholera toxin core region and flanking sequences of sufficient length to promote detectable in vivo recombination, ligated to a gene encoding a first selectable marker of foreign origin which confers resistance to a selective agent, wherein said first plasmid is incapable of replicating extrachromosomally in *V. cholerae;*

(b) mating a virulent strain of *Vibrio cholerae* of a non-O1 serogroup with a first microorganism carrying the first plasmid;

(c) selecting for and isolating *Vibrio cholerae* expressing the first selectable marker;

(d) growing the *V. cholerae* isolated in step (c) in the absence of said selective agent;

(e) screening the *V. cholerae* of step (d) for the loss of expression of said first selectable marker;

(f) providing a second plasmid comprising *Vibrio cholerae* non-O1 chromosomal sequences which flank the cholera toxin locus, deleted of DNA of the cholera toxin core and RS1 sequences, ligated to a second selectable marker of foreign origin which confers resistance to a second selective agent;

(g) mating the screened product of step (e) with a second microorganism carrying said second plasmid; and (h) selecting for *Vibrio cholerae* which express the second selectable marker;

(i) growing the selected product of step (h) in the absence of the second selective agent;

(j) screening the *V. cholerae* of step (i) for the loss of said second selectable marker;

(k) isolating the screened product of step (j);

(l) providing a third plasmid comprising *V. cholerae* chromosomal sequences of sufficient length to promote detectable in vivo recombination flanking sequences of the cholera toxin B subunit sufficient to confer immunogenicity, and sequences encoding a product which confers resistance to heavy metals, and ligated to a third selectable marker of foreign origin, wherein said third plasmid is incapable of replicating extrachromosomally in *V. cholerae;*

(m) mating the screened product of step (k) with a third microorganism carrying said third plasmid;

(n) selecting for *Vibrio cholerae* which express the third selectable marker; and (o) isolating the selected product of step (n).

The non-O1 *V. cholerae* of the second method of the invention is deleted of all cholera toxin core and RS1 sequences at the chromosomal ctx locus, but expresses sequences of the cholera toxin B subunit sufficient to confer immunogenicity and sequences which confer resistance to heavy metals.

A third avirulent, non-O1 *V. cholerae* of the invention has a deletion of the cholera toxin core and RS1 sequences of non-O1 *Vibrio cholerae* but expresses re-inserted sequences of the cholera toxin B subunit sufficient to confer immunogenicity, and sequences encoding a product which confers resistance to heavy metals is also described. This third non-O1 *V. cholerae* mutant of the invention further is a recombination minus strain additionally having a deletion wherein the product of the recA locus is inactivated or absent.

This third method of the invention comprises the steps of:

(a) providing a first plasmid comprising DNA of the *Vibrio cholerae* cholera toxin core region and flanking sequences of sufficient length to promote detectable in vivo recombination, ligated to a gene encoding a first selectable marker of foreign origin which confers resistance to a selective agent, wherein said first plasmid is incapable of replicating extrachromosomally in *V. cholerae*;

(b) mating a virulent strain of *Vibrio cholerae* of a non-O1 serogroup with a first microorganism carrying the first plasmid;

(c) selecting for and isolating *Vibrio cholerae* expressing the first selectable marker;

(d) growing the *V. cholerae* isolated in step (c) in the absence of said selective agent;

(e) screening the *V. cholerae* of step (d) for the loss of expression of said first selectable marker;

(f) providing a second plasmid comprising *Vibrio cholerae* non-O1 chromosomal sequences which flank the cholera toxin locus, deleted of DNA of the cholera toxin core and RS1 sequences, ligated to a second selectable marker of foreign origin which confers resistance to a second selective agent;

(g) mating the screened product of step (e) with a second microorganism carrying said second plasmid; and (h) selecting for *Vibrio cholerae* which express the second selectable marker;

(i) growing the selected product of step (h) in the absence of the second selective agent;

(j) screening the *V. cholerae* of step (i) for the loss of said second selectable marker;

(k) isolating the screened product of step (j);

(l) providing a third plasmid comprising *V. cholerae* chromosomal sequences of sufficient length to promote detectable in vivo recombination flanking sequences of the cholera toxin B subunit sufficient to confer immunogenicity, and sequences encoding a product which confers resistance to heavy metals, and ligated to a third selectable marker of foreign origin, wherein said third plasmid is incapable of replicating extrachromosomally in *V. cholerae*;

(m) mating the screened product of step (k) with a third microorganism carrying said third plasmid;

(n) selecting for *Vibrio cholerae* which express the third selectable marker;

(o) isolating the selected product of step (l);

(p) providing a fourth plasmid comprising flanking sequences sufficient in length to promote detectable recombination at the *V. cholerae* recA locus, flanking recA gene sequences deleted to inactivate the recA gene product, ligated to a fourth selectable marker, wherein said fourth plasmid is incapable of replicating extrachromosomally in *V. cholerae*;

(q) mating the isolated product of step (o) with a fourth microorganism carrying said fourth plasmid;

(r) selecting for *Vibrio cholerae* which express the fourth selectable marker; and (s) isolating the selected product of step (r).

The *Vibrio cholerae* deletion mutants of this invention are useful for vaccination to protect against the symptoms of cholera in response to non-O1 *V. cholerae*, as well as in methods for producing cholera vaccines.

One *Vibrio cholerae* strain of the present invention, designated CVD112, confers substantial protection in humans against the symptoms of cholera upon subsequent exposure to a strain of a similar non-O1 serotype. Other *Vibrio cholerae* strains of the present invention, designated by the third culture, designated CVD112 RM, can confer substantial protection in humans against the symptoms of cholera when challenged with a strain of a similar non-O1 serotype, and also is incapable of recA-mediated homologous recombination. Another *Vibrio cholerae* strain disclosed is designated CVD111. Strain *V. cholerae* CVD111 contains sequences of the cholera toxin B subunit sufficient to confer immunogenicity as well as the useful selectable marker of mercury resistance.

BRIEF DESCRIPTION OF THE DRAWINGS

FIG. 14. Quantitation of ZO complexity in tissues exposed to culture supernatants or broth control.

FIG. 16A–16D. Scheme for construction of CVD109. The zot and ctx genes are adjacent to each other on the *V.* cholerae chromosome and are in a region of the chromosome which contains multiple copies of a 2700 sequence called RS1 (repetitive sequence). RS1 elements are on both sides of zot and ctx genes in virulent *V. cholerae* strain E7946 (El Tor biotype, Ogawa serotype). The zot and ctx genes are shown by a large open or hash-marked arrow. RS1 sequences are shown by a smaller, solid arrow.

FIG. 17 (A and B). DNA sequence of the zot gene for zonula occludens toxin from nucleotides number 1 to 1428 (SEQ ID No.7). Letters above the DNA sequence indicate the predicted amino acid sequence of the ZOT protein (SEQ ID No. 8) encoded by the zot gene.

FIG. 18. Scheme for construction of plasmid pCVD621 and plasmid pCVD622.2B.

FIG. 19A–19D. Scheme for construction of CVD110.

Abbreviations for restriction endonuclease sites in the drawings are as follows:

A=AccI restriction endonuclease site
B=BglII restriction endonuclease site
C=ClaI restriction endonuclease site
E=EcoRI restriction endonuclease site
H=HindIII restriction endonuclease site
P=PstI restriction endonuclease site
S=SalI restriction endonuclease site
X=XbaI restriction endonuclease site
K=KpnI restriction endonuclease site Other abbreviations in the drawings and elsewhere include:

Ap=Ampicillin resistance gene
$Ap^r$ =Ampicillin resistance phenotype
$Ap^s$ =Ampicillin sensitive phenotype
Chrom=Chromosome
Cm=Chloramphenicol resistance gene
CT=Cholera toxin
ctx=gene for cholera toxin
CTA=A subunit of cholera toxin
ctxA=gene for A subunit of cholera toxin
CTB=B subunit of cholera toxin
ctxB=gene for B subunit of cholera toxin
hylA=gene for hemolysin
kb=Kilobases
mer=gene for mercury resistance
p=plasmid
Su=Sulfonamide
$Su^r$ =Sulfonamide resistance phenotype
Tc=tetracycline
$Tc^s$=tetracycline sensitive phenotype
Tp=Trimethoprin
zot=gene for zonula occludens toxin
ace=gene for cholera toxin locus accessory protein
cep=potential coding sequence for putative, as yet unsubstantiated, core encoded pilin FIG. 20. Map showing the relative positions of the ctx, zot and ace genes, OrfU and the RS1 flanking sequences. (RS1 is shown by large arrows). The two boxes with the vertical stripes correspond to the two open reading frames in which ACE activity was initially localized. It is now thought that ACE activity is localized to the open reading frame adjacent to the zot gene. The fragment contained in the clone pCVD630 is shown.

FIG. 21. Using chamber activity of *V. cholera* strains CVD110 and CVD110 containing pCVD630. Panel on the left FIG. 21A shows changes induced in short circuit current (ISC) and panel on right FIG. 21B shows changes in potential difference (PD).

FIG. 22A–f). DNA sequence of the 2.9 kb EcoRV fragment containing ACE activity (sequence GATATC at beginning and end of sequence is the EcoRV site). The complete DNA sequence for classical strain 395 is shown (SEQ ID No.: 1). Below the 395 sequence is shown the sequence for this region from El Tor strain E7946 (SEQ ID No.: 4)—only those bases of E7946 which differ from those in 395 are shown. Where the sequence is identical for the two strains, only the 395 sequence is shown. (Dashed lines at bases 236–239 show that E7946 has a 3 base insert (AGT) which is not present in 395). Above the primary DNA sequence line is shown the amino acid sequence (in single letter code) predicted from the 395 sequence (SEQ ID Nos. 15 and 16). The two ORFs are translated; classical 395 OrfU spans bases 1034 to 2218 (SEQ ID No.: 3); classical 395 ace spans bases 2221 to 2508 (SEQ ID No.: 2); El Tor OrfU spans bases 1037 to 2221 (SEQ ID No.: 6); and, E1 Tor ace spans bases 2224 to 2511 (SEQ ID No.: 5).

FIG. 23. A representation of the arrangement of the cholera toxin chromosomal locus of *V. cholerae* non-O1 strain 1837.

FIG. 24. Representation of the arrangement of the cholera toxin locus of *V. cholerae* strain 1837 (first line), strain 1837.1 (second line), strain 1837.2 (third line) and strain CVD112 (fourth line).

FIG. 25. Representation of plasmids pLC13, pLC14, pLC15 and pLC16.

FIG. 26. Scheme for the insertion of cholera toxin B subunit encoding sequences and mercury resistance encoding sequences into the *V. cholerae* O139 strain 1837.2 chromosome at the hylA locus.

FIG. 27. Representation of the recombination event that occurs at the *V. cholerae* recA locus in the generation of strain CVD112RM.

FIGS. 28A, 28B, 28C, and 28D. Wheat germ agglutinin—horseradish peroxidase (WGA-HRP) permeability assay on rabbit ileal tissues exposed to culture supernatants of various *V. cholerae* strains. a, medium control; b, *V. cholerae* 395; c, *V. cholerae* 395N1; d, *V. cholerae* CVD101.

FIGS. 29A and 29B. Freeze-fracture studies of rabbit ileal tissue exposed to culture supernatants of *V. cholerae* a, An intact ZO with numerous intersections (arrowheads) between junctional strands M, microvilli. b, An affected ZO from ileal tissue exposed to *V. cholerae* 395; the reticulum appears simplified due to greatly decreased incidence of strand intersections.

DETAILED DESCRIPTION OF THE INVENTION

The present invention comprises *V. cholerae* strains, their method of production and their methods of use. The strains of *Vibrio cholerae* of the invention are useful as vaccine strains and are specifically altered through recombinant DNA technology to render them avirulent, without substantially affecting other components necessary for immunity. This attenuation was accomplished by restriction endonuclease digestion of plasmids carrying appropriate *V. cholera* sequences, to specifically delete the genes coding for cholera toxin, or portion thereof. Conjugal gene transfer of these plasmids carrying deleted cholera toxin genes into virulent host *V. cholera*, followed by selection for in vivo recombinants, resulted in strains without the toxin genes or portion thereof. It will be understood that the methods of the present invention are applicable to the isolation of other deletion mutants of virulent *V. cholerae*, or to the isolation of strains having all or part of such deleted sequences reintroduced into the *V. cholerae* cell.

The starting material for the vaccines were the toxigenic *Vibrio cholerae* O1 N16961. Strain N16961 has been demonstrated to produce in both typical diarrheal disease and strong, protective immunity to subsequent infection [Levine, M. M. et al., *Acute enteric*, supra, 1981]. The region of the bacterial chromosome which was found to be responsible for production of cholera toxin was cloned into the plasmid cloning vehicle pBR325, after screening HindIII digest of *V. cholerae* DNA with an *E. coli* heat-labile enterotoxin gene probe [Kaper et al. *Amer. Soc.*, supra; Kaper et al. *Symposium*, supra]. A *V. cholerae* HindIII chromosomal fragment was found to contain all genes necessary for toxin production. Next, this chromosomal region was analyzed and mapped for the exact portions containing the toxin genes [Kaper, J. B. et al. *Lancet II*, 1162 (1981)]. Restriction enzymes were employed to cut out the DNA fragments containing these genes and a DNA fragment encoding a selectable marker (e.g., resistance to ampicillin) was inserted by ligation. The ampicillin resistance gene and the flanking vibrio DNA were then cloned in a derivative of pRK290, which can be used to transfer DNA from *E. coli* to *V. cholerae*. The resulting plasmid, pJBK55, was transferred from *E. coli* K-12 to *V. cholerae* N16961 by conjugation.

Figure 1:
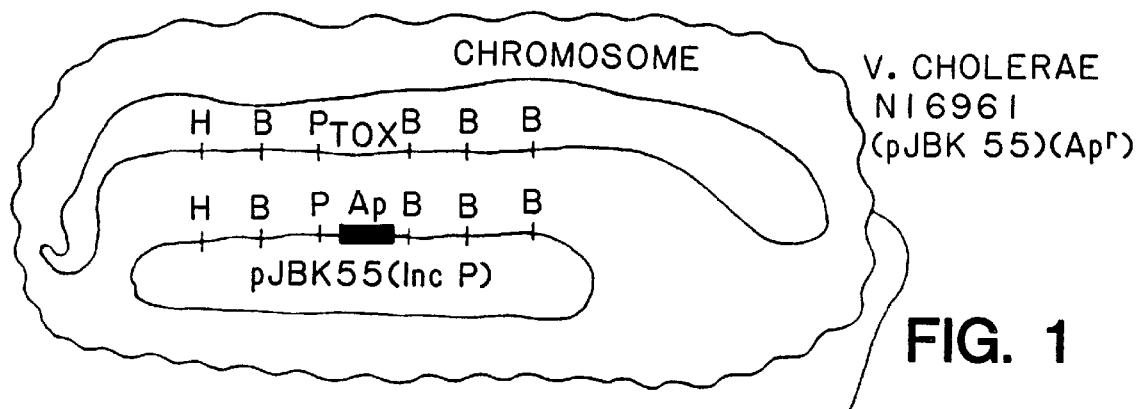
FIG. 1. *V. cholerae* N16961 (pJBK55) (Ap$^r$)
Figure 2:
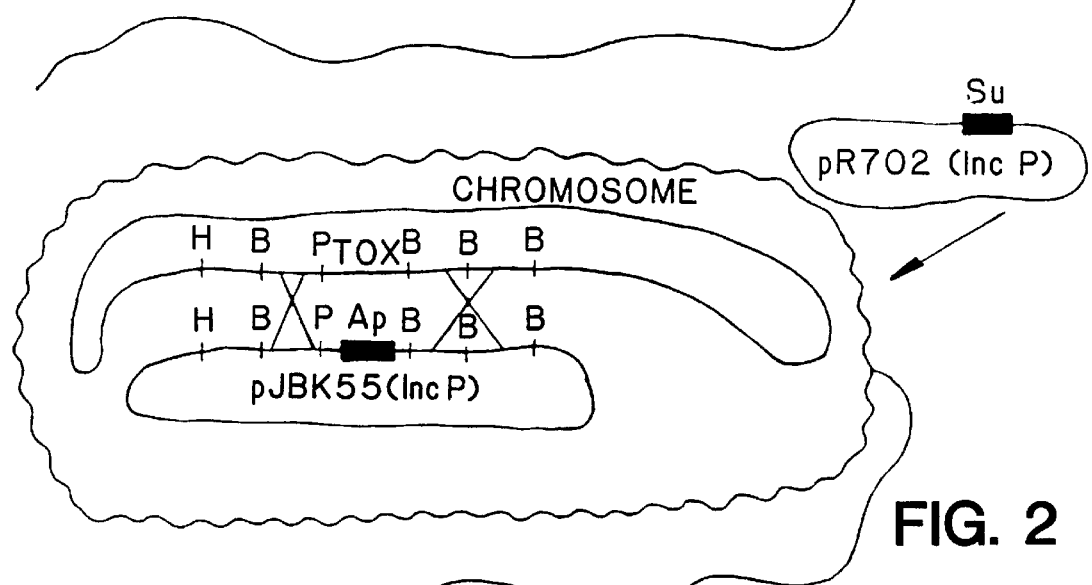
FIG. 2. Processes of crossing-over and conjugal gene transfer to construct *V. cholerae* JBK56.
Figure 3:
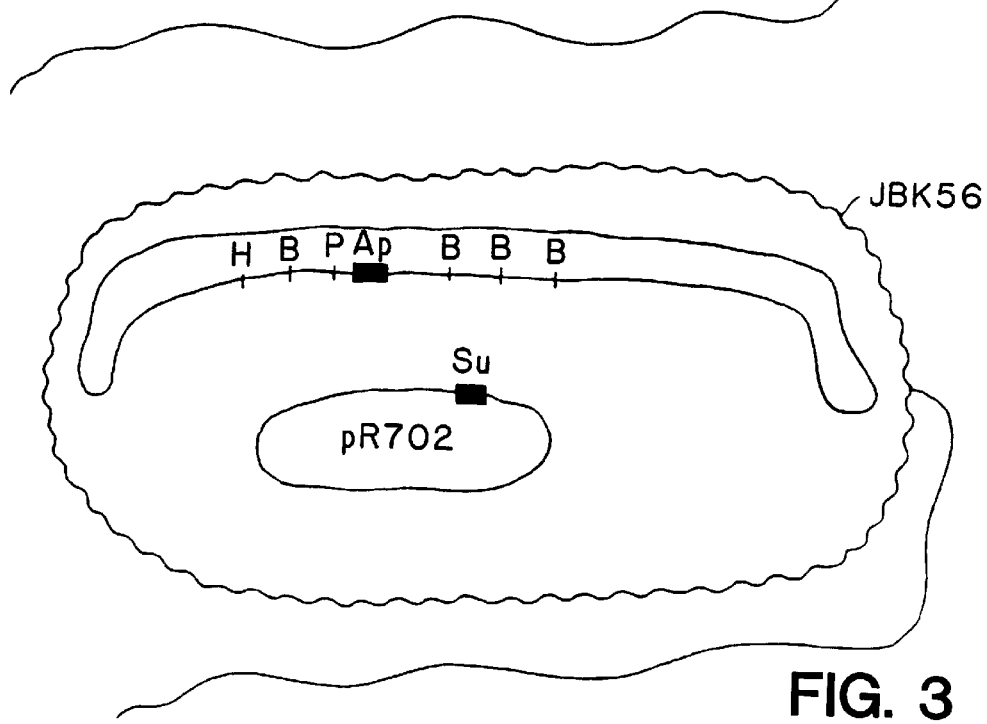
FIG. 3. *V. cholerae* JBK56.
Figure 5:
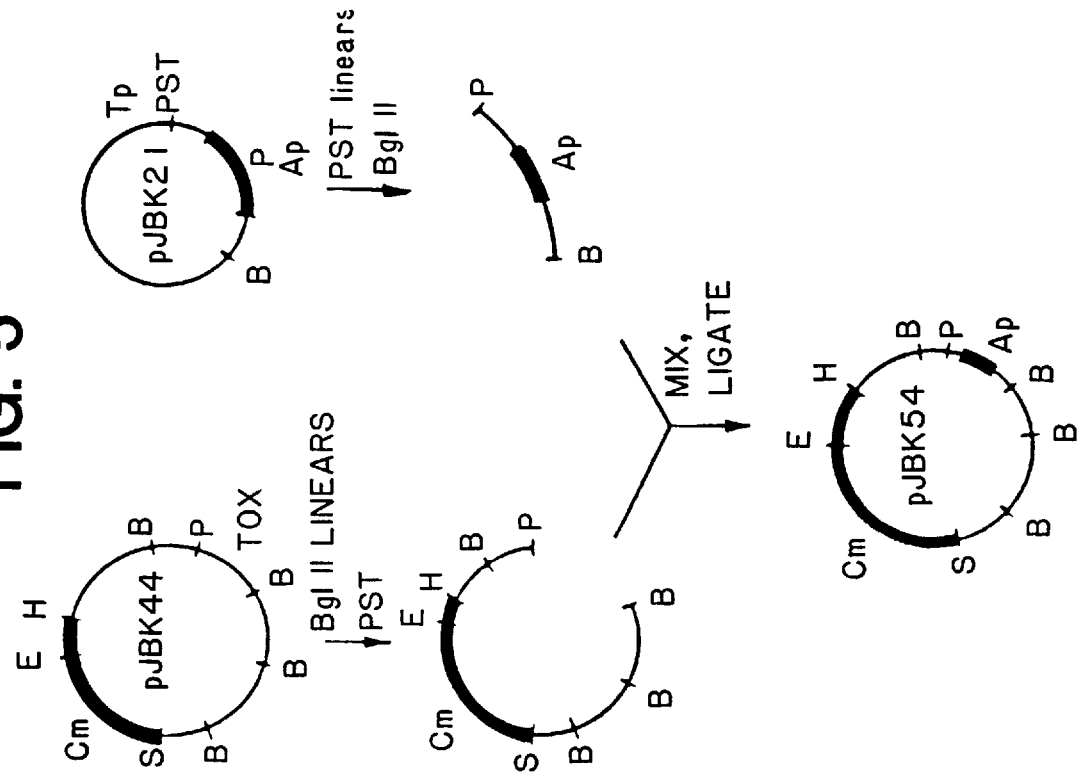
FIG. 5. Scheme for construction of pJBK54.
Figure 4:
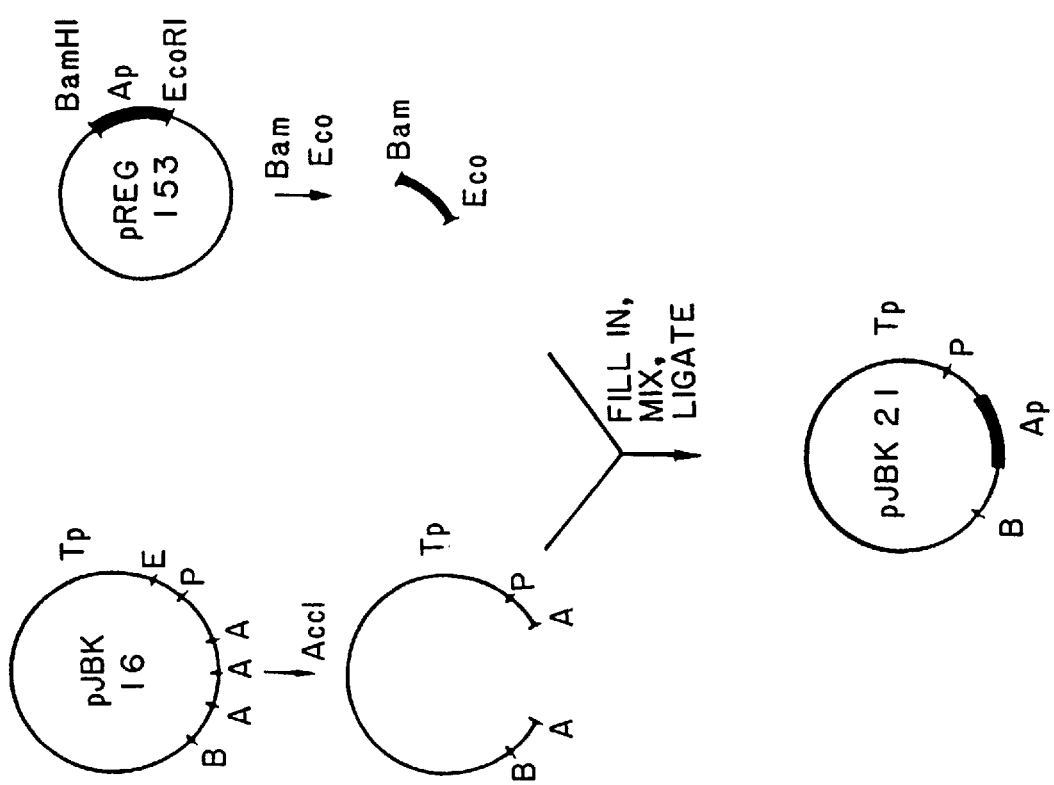
FIG. 4. Scheme for construction of JBK21.
Figure 7:
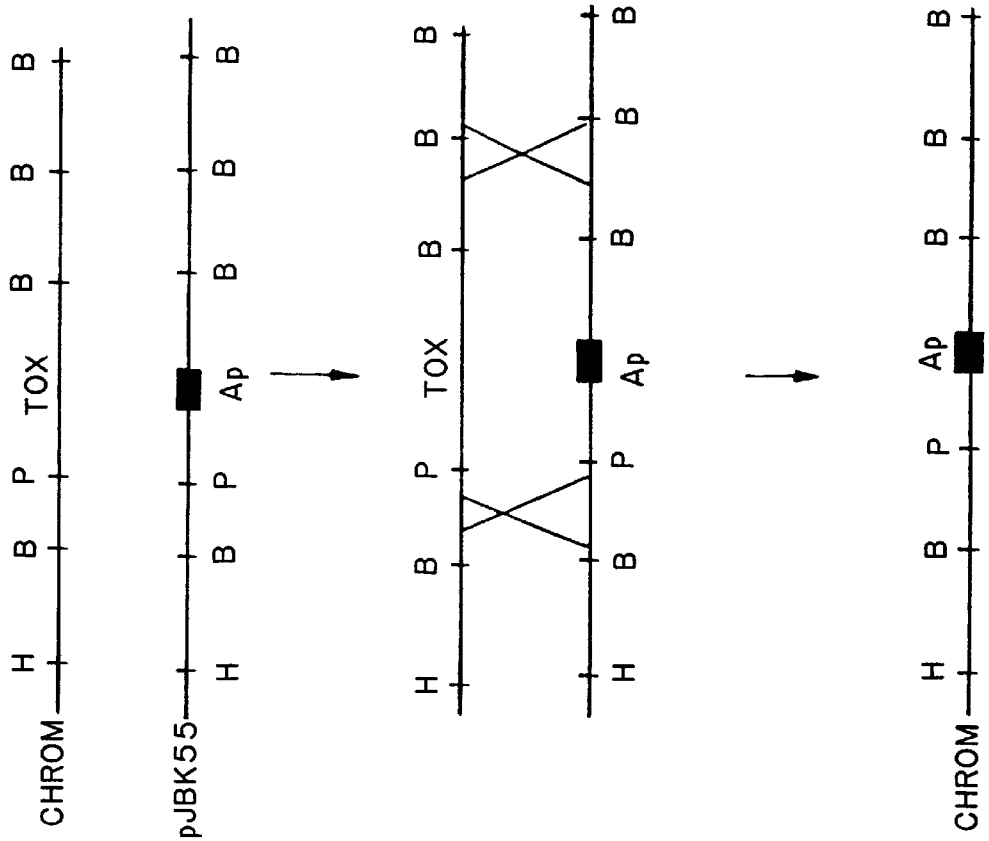
FIG. 7. Recombination in vivo by cross over and elimination of ctx gene.
Figure 6:
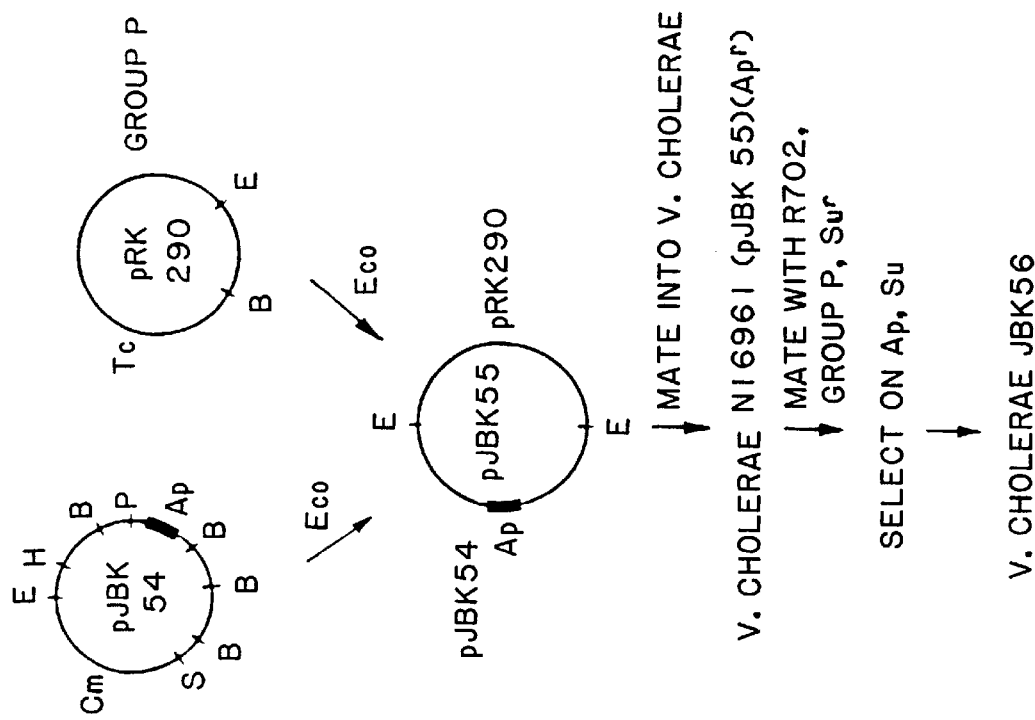
FIG. 6. Scheme for construction of *V. cholerae* JBK56.
Figure 8:
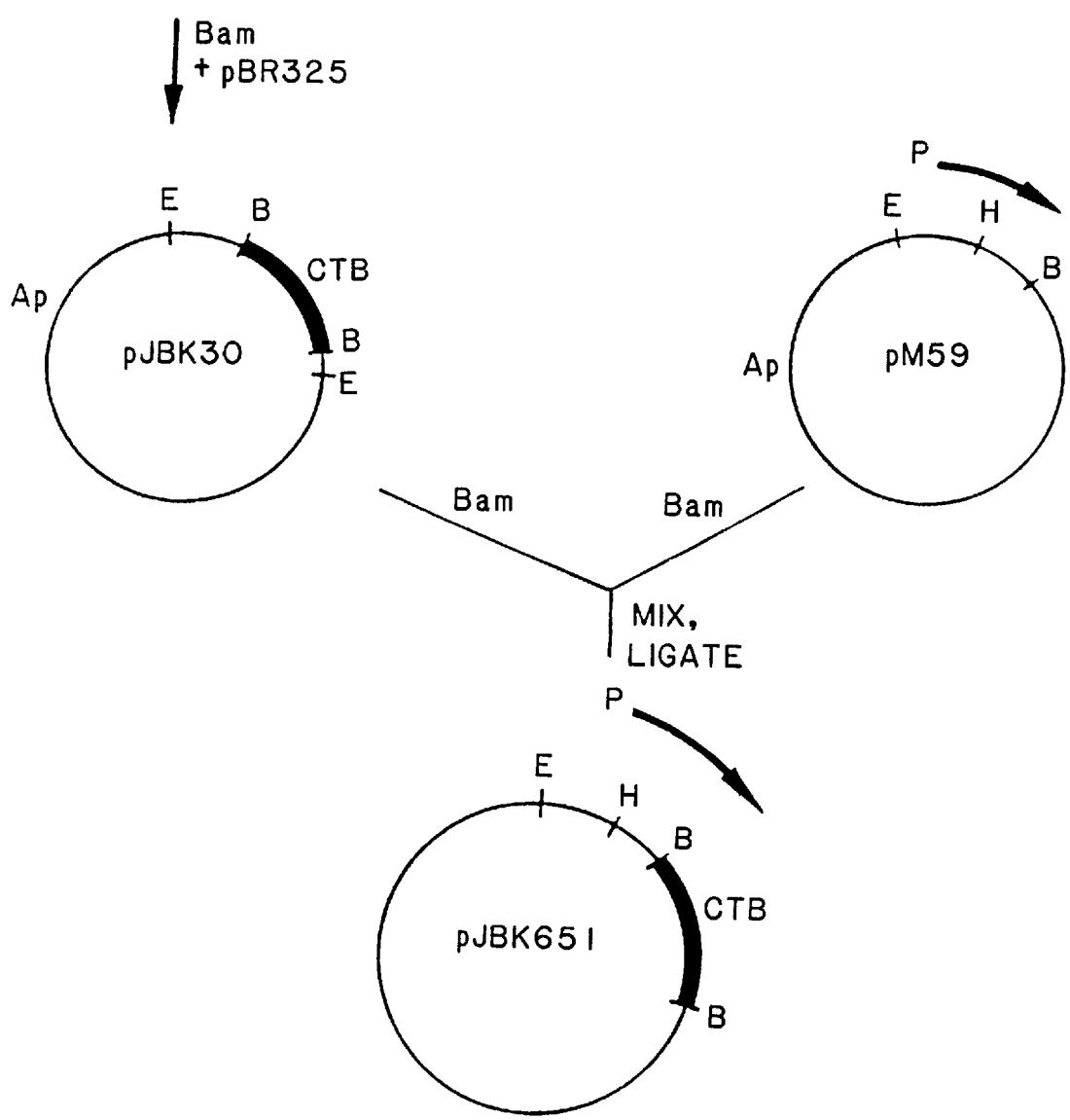
FIG. 8. Scheme for construction of pJBK51.

The resulting strain, *V. cholerae* N16961 (pJBK55) (Ap$^r$) contained a region in its chromosome having intact toxin genes and, in an extrachromosomal state, a plasmid containing this same region with the toxin genes deleted and a gene for ampicillin substituted. (See FIG. 1.) At a low frequency, perhaps one in $10^6$ to one in $10^8$, the identical regions flanking the chromosomal toxin genes and the extrachromosomal (plasmid) ampicillin resistance gene will exchanged or "crossed over" or undergo in vivo recombination so that the region of DNA containing the resistance gene displaces the toxin gene on the chromosome (FIG. 2). This rare event is selected by testing a mixture of mutated and non-mutated cells for individual cells which are able to serve as host for an incoming incompatible plasmid [Ruvkun, G. B. et al. *Nature* 289, 85 (1981)]. Plasmids are divided into groups designated A through W, the members of which cannot stably coexist with each other. For example, a plasmid of incompatibility group P cannot be stably maintained in the same cell as another P group (Inc P) plasmid. Thus, Inc P plasmids, such as R702, which specify resistance to sulfonamide, cannot be maintained in a cell which has another Inc P. plasmid such as PRK 290, pJBK45, or pJBK55. Therefore, R702 can be maintained in a strain in which the ampicillin resistance has recombined into the chromosome but not one in which an Inc P Plasmid (e.g. pJBK55) is replicating extrachromosomally. By mating an *E. coli* strain containing Inc P R702 (sulfonamide resistant) and *V. cholerae* pJBK55 (ampicillin resistant) and selecting for *V. cholerae* which are resistant to both ampicillin and sulfonamide, colonies are isolated in which the sulfonamide resistance is mediated extrachromosomally by p702 and the ampicillin resistance is mediated chromosomally through substitution of the ampicillin resistance gene for the toxin gene (FIG. 3). One such strain, designated *V. cholerae* JBK56 was isolated and when tested for toxin production was found to be nontoxinogenic.

The final version of the vaccine strain, JBK70, was produced by substituting resistance to ampicillin, a therapeutically useful antibiotic, with resistance to mercury. This substitution was accomplished by cloning a gene for mercury resistance directly into the ampicillin resistant gene of pJBK55, thereby inactivating ampicillin resistance and conferring mercury resistance. The resulting plasmid, pJBK66 was also incompatible with R702 and was transferred to *V. cholerae* JBK56. A mutant in which the mercury resistance was recombined into the chromosome was selected using the Inc P plasmid R702 and selecting for *V. cholerae* which were ampicillin sensitive, mercury resistant, and sulfonamide resistant. A spontaneous derivative was later selected which was cured of pR702. The final mutant, JBK70, was nontoxinogenic and resistant to mercury only.

The vaccine strain *V. cholerae* JBK70 is one of the Inaba serotype. The other major serotype of *V. cholerae* is the Ogawa serotype. It is expected that a vaccine prepared from one serotype will protect against the other serotype (34). In the event that this is not the case, a live vaccine strain can be prepared from an Ogawa serotype and protection in volunteers [Levine, M. M. et al. *Acute enteric*, supra (1981) ]. The exact mutation created in strain *V. cholerae* Inaba JBK56 was recreated in strain E7946 by directly transferring the region of the chromosome containing the ampicillin resistance in place of the toxin gene in JBK56 into E7946 through genetic recombination mediated by P, the sex factor of *V. cholerae* [Parker, C. et al., supra]. The P factor, which is distinct from Inc P plasmid, was transferred into JBK56 and was then mated with a rifampin resistant mutant of E7946. By selection of a mutant which was resistant to both ampicillin and rifampin, a vaccine strain was isolated which was of the Ogawa serotype with the toxin genes completely deleted.

If antibacterial immunity is insufficient for protection, then an antitoxic component can be added by adding back the genes for production of cholera toxin B but not A subunit. This has been accomplished by cloning the B subunit gene into the cloning vector pMS9. The resulting plasmid, pJBK51, produces high levels of B subunit and was reintroduced into the nontoxic vaccine strain *V. cholerae* JBK70 to make an attenuated vaccine strain JBK70 (pJBK51) which fails to produce the A subunit.

The vaccine strains of the present invention are derived inter alia from *V. cholerae* N16961 having the serotype Inaba. It will be understood that other strains or other biotypes and serotypes can be used to substitute for N16961 to produce vaccine strains having specific deletions in the ctx gene or genes, or in other locations along the *V. cholerae* chromosome. Since the object of isolating such vaccine strains is to mimic the infection process without associated pathological phenomena, site-directed mutagenesis of virulent strains, as described in this application, produces substantial possibilities in the prophylactic vaccination against cholera.

For example, applicants have produced another *V. cholerae* vaccine strain CVD101, characterized by a deletion of most of the A subunit gene in 2 copies of the ctx genes. Construction of CVD101 followed in general the principles outlined supra, e.g. the construction of JBK70, except that the resulting CVD101 had no resistance gene that needed curing. The final step in isolating the second and find in vivo recombinant included a scheme for selecting sensitivity to an antibiotic e.g. tetracycline sensitivity, whereas the parent strain had inserted at the location of the A gene of CT a tetracycline resistance gene. It will be understood that such antibiotic sensitivity is another example of a selectable marker.

Production of vaccine strains can be performed by a variety of methods, including the following: *Vibrio cholerae* is subcultured from stock cultures into brain/-heart infusion agar (BHIA) and grown at 37° C. overnight. Identity is tested with group-and type-specific antisera and twenty to thirty colonies are suspended in BHI broth. Preincubated BHIA plates are inoculated with BHI suspension. After incubation for five to six hours, each plate is harvested with 5 ml of sterile saline buffered to pH 7.2±0.1. Harvested organisms are centrifuged in the cold at 750 g for ten minutes, resuspended and washed twice in four-times the original volume. The suspension is standardized spectrophotometrically and diluted to approximate the number of organisms required for vaccination (ca $10^6$, which varies depending on the results of volunteer studies). Replicate, pour-plate quantitative cultures are made of the inocula before and after challenge to confirm inoculum size. The final inoculum is examined with Gram's stain and agglutinated with homologous antiserum prior to feeding.

The *Vibrio cholerae* strains of the present invention can be administered by the oral route. Two grams of $NaHCO_3$ are dissolved in five ounces of distilled water. Volunteers drink four ounces of the $NaHCO_3$/water; one minute later the volunteers ingest the vibrios suspended in the remaining one ounce of $NaHCO_3$/water. Volunteers are NPO ninety minutes pre- and post-inoculation.

With regard to safety, the major concern is that the vaccine strain does not revert to toxigenicity (i.e., produce intact cholera toxin) which could cause disease. The two major assays for testing toxin are the Y-1 adrenal cell assay [Sack, D. A. et al. *Infect. Immun.* 11, 334 (1975)] and the enzyme-linked immunosorbent assay (ELISA) [Sack, D. A. et al. *J. Clin. Micro.* 11, 35 (1980)]. The vaccine strain (JBK70) has been repeatedly tested in these two assays and found to be negative each time. Far more important, however, are the genetic assays performed for the presence of toxin genes. The DNA for cholera toxin genes can be radioactively labeled and used as a specific probe to identify other cholera toxin genes in the strain, according to the method of Southern, E. M. *J. Mol. Bio.* 98, 503 (1975). When tested by this method, the vaccine strain described in the invention possesses no detectable genetic material that can enclose cholera toxin. The vaccine has also been tested in an infant mouse model, according to Baselski, V. et al. *Infect. Immun* 15, 704 (1977). After repeated (ten in all) serial passages, no fluid accumulation (i.e., evidence of disease has been found. As expected, JBK70 was found to colonize the infant mouse intestine.

In order to avoid undesirable side effects of the vaccine strains, such as diarrhea and nausea, cramping, and other symptoms, the vaccine strains may further comprise a second restriction endonuclease fragment of DNA coding for zonula occludens toxin (ZOT) deleted.

A culture of *Vibrio cholerae* comprises a *Vibrio cholerae* strain having a first restriction endonuclease fragment of DNA deleted to confer avirulence and retain capacity to colonize the intestine of a host animal and having a second restriction endonuclease fragment of DNA coding for zonula occludens toxin (ZOT) deleted to reduce residual diarrhea in the host animal. The first DNA fragment deleted may code for the *V. cholerae* toxin or portions thereof such as the $A_1$ subunit. One isolated deletion mutant encompasses a deletion in the ctx gene, as defined by AccI restriction endonuclease sites, and a deletion in the zot gene. Another isolated deletion mutant encompasses a deletion in the ctx gene, as defined by XbaI and ClaI restriction endonuclease sites, and a deletion in the zot gene, as defined by StuI and AccI restriction endonuclease sites A method of isolating such deletion mutants of *Vibrio cholerae* comprises the steps of (a) constructing a first plasmid comprising *Vibrio cholerae* flanking sequences of one or more deleted restriction endonuclease fragments and a gene for a selectable marker of foreign origin ligated to said flanking sequences to substitute for and to be in place of said deleted fragment, wherein said sequences are of sufficient length to promote detectable in vivo recombination;

(b) mating a virulent strain of *Vibrio cholerae* with a first microorganism carrying the first plasmid;

(c) selecting for *Vibrio cholerae* expressing the first selectable marker;

(d) mating the selected product of step (c) with a second microorganism carrying a second plasmid with a second selectable marker, said second plasmid being incompatible with the first plasmid;

(e) selecting for *Vibrio cholerae* expressing both the first selectable marker and the second selectable marker;

(f) constructing a third plasmid comprising *Vibrio cholerae* flanking sequences of one or more deleted restriction endonuclease fragments homologous to those described in step (a) but differing in the absence of a selectable marker of foreign origin;

(g) mating the selected product of step (e) with a third microorganism carrying a third plasmid described in step (f); and (h) selecting for *Vibrio cholerae* which no longer expresses the first selectable marker.

This method nay be used for ZOT minus only strains or for making a ZOT minus derivative of a strain which is already deleted for cholera toxin genes.

Another culture of *Vibrio cholerae* comprises a *Vibrio cholerae* strain having a region of the chromosomal DNA coding for cholera toxin and zonula occludens toxin (ZOT) deleted. A method of isolating such deletion mutants of *Vibrio cholerae* comprises the steps of (a) constructing a plasmid comprising *Vibrio cholerae* sequences coding for cholera toxin and zonula occludens toxin and a gene for a selectable marker of foreign origin, wherein said plasmid is incapable of replicating extrachromosomally in *Vibrio cholerae;*

(b) mating a microorganism carrying said plasmid with a virulent strain of *Vibrio cholerae* containing said sequences to promote detectable in vivo recombination;

(c) selecting for *Vibrio cholerae* expressing said selectable marker;

(d) growing the selected product of (c) in the absence of the selective agent;

(e) selecting for *Vibrio cholerae* which no longer express the selective marker; and therefore have a region of the chromosomal DNA coding for cholera toxin and zonula occludens toxin deleted. Step (b) may comprise: (b) mating a microorganism carrying said plasmid with a virulent strain of *Vibrio cholerae* containing said sequences inserted between flanking identical copies of a second sequence such as RS1 elements of sufficient length to promote detectable in vivo recombination.

The *Vibrio cholerae* deletion mutants of this invention are useful in vaccination against cholera.

Herein reported is a new toxic factor elaborated by *V. cholerae* which increases the permeability of the small mucosa by affecting the structure of the intercellular tight junctions or zonula occludens (ZO) (the paracellular pathway of ion transport). Production of this factor by *V. cholerae* correlates with diarrheagenicity in volunteers. By disturbing the normal absorptive processes of the small intestine via the paracellular pathway, this factor could be responsible for the residual diarrhea induced by ctx deletion mutants of *V. cholerae* and may contribute to the severe diarrhea that distinguishes cholera from other diarrheal diseases.

Changes in intestinal function induced by three strains of *V. cholerae*, one wild type and two attenuated vaccine strains, were examined. *V. cholerae* strain 395, classical biotype, Ogawa serotype, is a highly virulent strain which has been extensively characterized in volunteer studies conducted at the Center for Vaccine Development. This strain induces diarrhea with a mean stool volume of 5.5 liters (range of 0.3 to 44 1) in greater than 90% of volunteers ingesting $10^6$ organisms [Levine, M. M. et al, *Infect. Immun.* 56, 161–167 (1988)]; [Levine, M. M., *Cholera and Related Diarrheas*, 195–203] (Karger, Basel, 1980). Cholera diarrhea is principally due to the enzymatic effects of the A subunit of CT on intestinal mucosa. The CT A subunit, encoded by ctx, stimulates adenylate cyclase and results in net secretion of fluid into the intestinal lumen. Gill, D. M. Adv. *Cyclic Nucleotide res.* 8, 85–118 (1977). *V. cholerae* vaccine strain CVD101 is a ctx deletion mutant of 395 in which 94% of the sequences encoding the $A_1$ peptide of CT have been removed. Surprisingly, although CVD101 no longer produces active CT, this strain caused mild to moderate diarrhea (mean stool volume of 0.9 l with a range of 0.3 to 2.1 l) in 54% of volunteers ingesting this organism. A second derivative of 395, vaccine strain 395N1, constructed by Mekalanos, et al., *Nature* 306, 551–557 (1983), lacks ca. 77% of the sequences encoding the $A_1$ peptide by applicants' calculation. In contrast to CVD101, 395N1 induced very mild diarrhea (0.3 l stool volume) in only 1 of 21 volunteers (P=0.002 compared to 13 of 24 volunteers with diarrhea after ingestion of CVD101). [Herrington, D. A. et al. *J. Exp. Med.* 168, 1487–1492 (1982)]. Since these strains were similar in their ability to colonize the intestine, applicants hypothesize that CVD101 produces a secretogenic factor which is expressed weakly or not at all by 395N1 and that this factor is responsible for the diarrhea seen in volunteers ingesting CVD101.

Figure 13B:
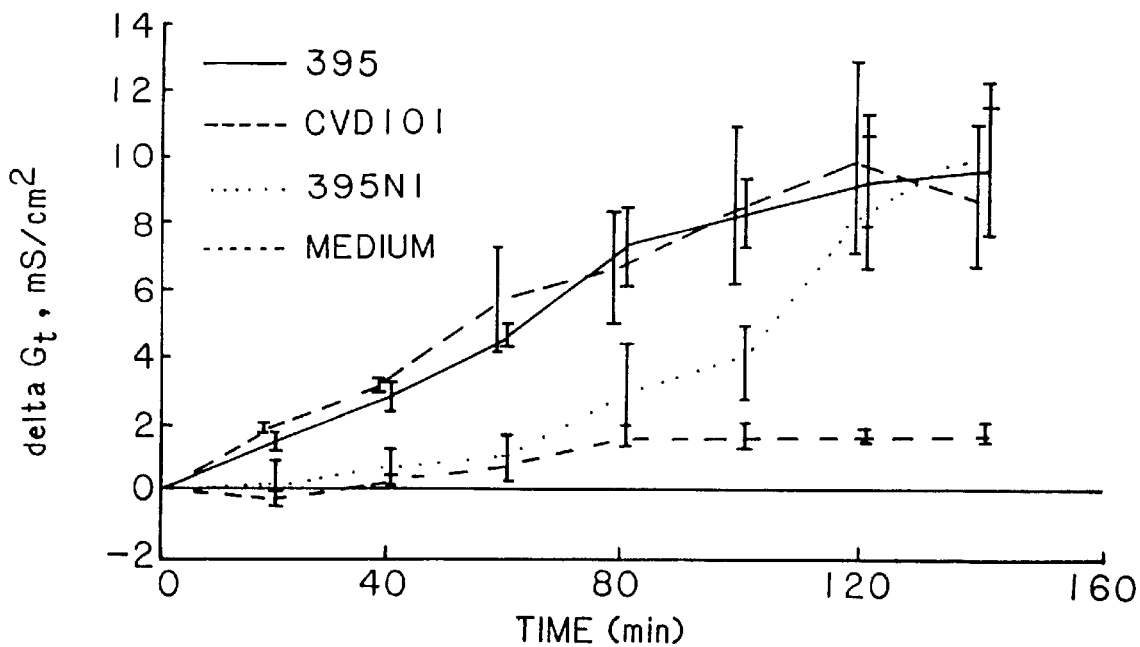
FIGS. 13A and 13B. Effect of *V. cholerae* culture supernatant on ileal short circuit current (Isc) and tissue ionic conductance (Gt). Values are means for 6 animals at each time-point; brackets are 1 standard error a, Effect of *V. cholerae* 395 supernatants on Isc (solid lines) and Gt (dashed lines). b, Effect of *V. cholerae* 395 (solid Line), CVD101 (long dashed line) and 395N1 (dotted line) supernatants on Gt. Medium control (short dashed line) consisted of un-inoculated culture medium.
Figure 13A:
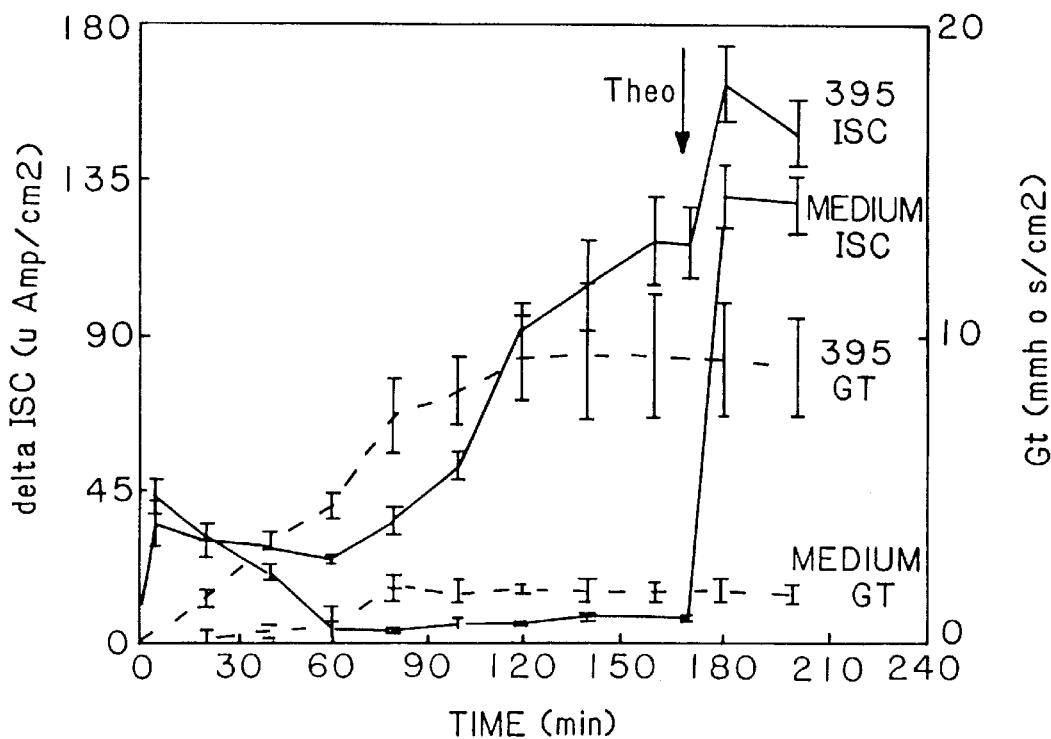

These strains were studied using rabbit intestinal tissue mounted in Ussing chambers, a classic technique for studying the transport process across intestinal tissue. Supernatants of *V. cholerae* cultures were added to the chambers and potential difference (PD) and short circuit current (Isc) were measured. PD is the difference in voltage measured on the mucosal side vs. the serosal side of the tissue and Isc is the amount of current needed to nullify the PD. From these measurements, tissue conductance (Gt) was calculated using Ohm's law: Isc=PD×Gt. Applicants first studied the effect of supernatants of the wild type strain 395 on these parameters using uninoculated culture media added to matched ileal tissue from the same animal as a negative control. FIG. 13A shows the Isc and Gt variations obtained. The initial peaks in Isc and PD that occurred in both negative controls and test samples were most likely due to the cotransport of Na and nutrients present in the media. In the negative control, Isc and PD returned to baseline values after approximately one hour and subsequently Isc, PD and Gt remained unchanged for the rest of the experiment. In contrast, tissues exposed to strain 395 supernatant exhibited a significant increase in Gt, reaching a maximum value after 2 hrs of incubation. In such samples, the Isc never returned to the baseline, but a steady state period for Isc was noted between 40 and 60 minutes. Since Isc is equivalent to PD×Gt and the observed PD after 60 min. was similar to the initial value (data not shown), the significant increase in Isc in 395-treated tissues at that time point can only be due to an increase in Gt (see FIG. 13A time 60 Min.) (12). After 60 min., Isc began to rise again along with PD in 395-treated tissues. This second phase probably reflects the effect of cholera toxin on ion fluxes since purified CT increases Isc in rabbit ileal tissue only after a lag time of at least 40 minutes. These data suggest that there are two factors expressed by *V. cholerae* 395 that can alter ion transport in Ussing chambers. One factor, cholera toxin, induces an increase in Isc and PD beginning ca. 60 minutes after addition of culture supernatant while a second factor induces an immediate increase in tissue conductance which is observable within 20 minutes after addition of culture supernatant.

Gt variation induced by culture supernatants of the attenuated *V. cholerae* strains CVD101 and 395N1 was next studied. CVD101 induced an immediate increase in Gt which was indistinguishable from that seen with 395 (FIG. 13B). In contrast, 395N1 induced no immediate increase in Gt; Gt variation in 395N1-treated tissues was similar to the negative broth control and significantly lower than that seen with 395 and CVD101 for almost 100 min of incubation. After this period, Gt modification in tissues exposed to 395, CVD101 and 395N1 were similar. These results suggest that 395N1 produces lower amounts or a less active form of the factor responsible for this increase in Gt.

Variation in transepithelial conductance reflects modification of tissue permeability through the intercellular space, since plasma membrane resistances are relatively high. Since ZO represents the major barrier in this paracellular pathway and variation in Gt is the most sensitive measure of ZO function, morphological modifications of ZO induced by *V. cholerae* 395, CVD101 and 395N1 supernatants were examined. If a low-molecular weight electron-dense marker such as wheat germ agglutinin—horseradish peroxidase (WGA-HRP) is added to the mucosal side of an epithelial sheet, it will usually not pass beyond to ZO [Alberts, B. et al., *Molecular Biology of the Cell* 2nd ed (1989)]. WGA-HRP was added to the mucosal side of intestinal tissue treated with culture supernatants of 395, CVD101 , 395N1 or uninoculated broth control for 60 minutes. Tissues treated with uninoculated culture medium were not permeable to WGA-HRP, while 395 and CVD101 -treated tissues showed the entry of the stain into the paracellular space. Tissues exposed to 395N1 supernatants were unaffected, inasmuch as the intercellular space remained tight enough to exclude the passage of WGA-HRP (FIG. 14). These results were confirmed and extended using freeze-fracture electron microscopy wherein the number of strands lying in parallel at the ZO correlates with transepithelial electrical conductance. Tissues exposed to culture supernatants showed a mixture of unaltered ZO and altered ZO with decreased strand complexity. Strands lying perpendicular to the long axis of the ZO appeared to be preferentially lost, resulting in a decreased number of strand intersections. The complexity of the ZO exposed to each strain supernatant was quantified by measuring the density of strand intersections. As seen in FIG. 14, tissues treated with culture supernatants of 395 or CVD101 showed a significant decrease in the number of strands and in the complexity of the reticulum of the ZO when compared to tissues treated with uninoculated broth or supernatants of 395N1.

The alterations of ZO morphology induced by 395 and CVD101 parallel the increased tissue conductance induced by these strains. The function of intestinal ZO is to regulate the paracellular pathway and restrict or prevent the diffusion of water-soluble molecules through the intercellular space back into the lumen. This diffusion is driven by concentration gradients created by the transepithelial transport processes. As a consequence of alteration of the paracellular pathway, intestinal mucosa becomes more permeable and water, Na and Cl leak into the lumen, resulting in diarrhea. The alteration of the paracellular pathway induced by *V. cholerae* 395 and CVD101 is specific for the small intestine; substitution of rabbit cecal tissue for ileal tissue resulted in no variation in Gt induced by 395 supernatant (data not shown). This is the first report of a bacterial factor which is capable of loosening tight junctions in intact intestinal tissue and may represent a new mechanism of bacterial diarrhea. Clostridium difficile toxin A, influenza, and vesicular stomatitis (VSV) viruses have been shown to loosen tight junctions in tissue culture monolayers but such activity in intact tissue or correlation with diarrhea have not been reported.

Figure 15:
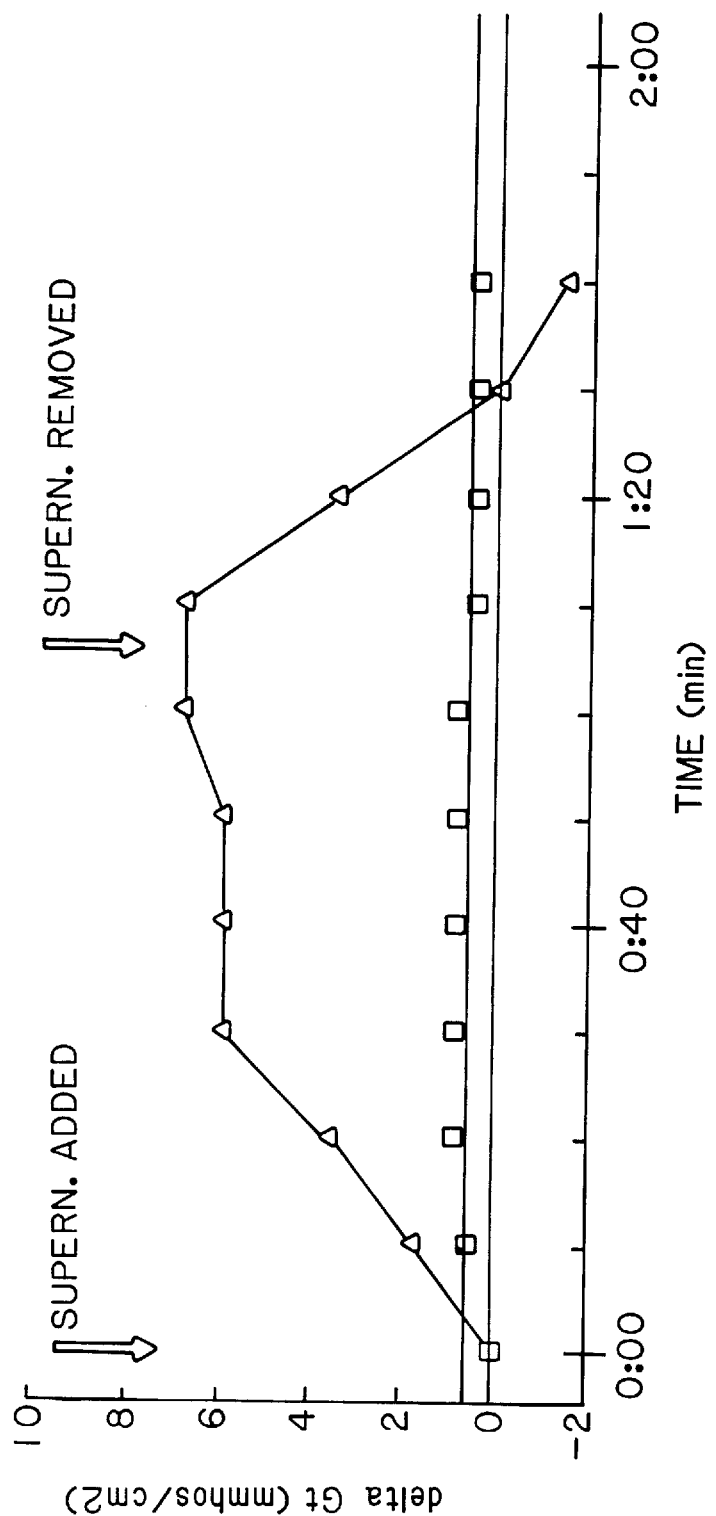
FIG. 15. Reversibility of Gt variations induced by *V. cholerae* 395 supernatant. Culture supernatants of *V. cholerae* (triangles) and uninoculated medium (squares) were added and removed at the time indicated by arrows.

Thus, *V. cholerae* 395 and CVD101 produce a factor which may be responsible for diarrhea seen in volunteers ingesting ctx deletion mutants of *V. cholerae*. The diarrhea induced by these ctx mutants is equivalent to that seen with many strains of enterotoxigenic *E. coli*. This secretogenic factor, which applicants have termed ZOT for zonula occludens toxin, induces an early increase in Isc and tissue conductance which is not related to the effects of CT on ion fluxes. This increase in Gt is associated with loosening of the tight junctions, an effect which was quickly reversed upon removal of the supernatant (FIG. 15). The quick reversal of this effect is in contrast to the long-lasting effect of CT. These results do not account for previously unexplained observations of Fields, et al., *J. Clin. Invest.* 51, 796–804 (1972) who noted an immediate increase in Isc induced by crude, but not purified CT preparations, and may account for Nishibuchi et al., *Infect. Immun.* 40, 1083–1091 (1983) who noted an early fluid accumulation (FA) unrelated to the delayed CT-induced FA in suckling mice fed *V. cholerae*. The ability of CT-negative *V. cholerae* to induce diarrhea in volunteers correlates with production of ZOT by two attenuated strains derived from the same parent strain; CVD101 (diarrheagenic) produces ZOT while 395N1 (non-diarrheagenic) produces little or no ZOT activity.

Another culture of *Vibrio cholerae* comprises a *Vibrio cholerae* strain having a region of chromosomal DNA coding for cholera toxin and zonula occludens toxin deleted, and having inserted a mercury resistance gene and DNA coding for B subunit of *Vibrio cholerae* toxin. A method of isolating such deletion mutants is also described comprising the steps of:

(a) constructing a plasmid comprising *Vibrio cholerae* sequences coding for cholera toxin and zonula occludens toxin and a gene for a selectable marker of foreign origin, wherein said plasmid is incapable of replicating extrachromosomally in *Vibrio cholerae*;

(b) mating a microorganism carrying said plasmid with a virulent strain of *Vibrio cholerae* containing said sequences coding for cholera toxin and zonula occludens toxin inserted between flanking identical copies of a second sequence of sufficient length to promote detectable in vivo recombination;

(c) selecting for *Vibrio cholerae* expressing said selectable marker;

(d) growing the selected product of (c) in the absence of the selective agent;

(e) selecting for *Vibrio cholerae* which no longer express the selective marker, and therefore have a region of the chromosomal DNA coding for cholera toxin and zonula occludens toxin deleted;

(f) constructing a second plasmid comprising a mercury resistance gene and DNA coding for B subunit of *Vibrio cholerae* toxin and a gene for a second selectable marker of foreign origin wherein said plasmid is incapable of replicating extrachromosomally in *Vibrio cholerae*, and wherein sequences of sufficient length to promote detectable in vivo recombination flank said mercury resistance gene and DNA coding for B subunit of *Vibrio cholerae* toxin;

(g) mating a microorganism carrying said second plasmid with said *Vibrio cholerae* recited in step (e) containing sequences homologous to said sequences of sufficient length to promote detectable in vivo recombination;

(h) selecting for *Vibrio cholerae* expressing said second selectable marker;

(i) growing the selected product of step (h) in the absence of the second selective agent;

(j) selecting for *Vibrio cholerae* which no longer express the second selective marker; and (k) screening said *Vibrio cholerae* recited in step (j) for *Vibrio cholerae* that have a mercury resistance gene and DNA coding for B subunit of *Vibrio cholerae* toxin and have a region of chromosomal DNA coding for cholera toxin and zonula occludens toxin deleted.

This method for isolating deletion mutants of *Vibrio cholerae* having a region of chromosomal DNA coding for cholera toxin and zonula occludens toxin deleted, and having inserted a mercury resistance gene and DNA coding for B subunit of *Vibrio cholerae* may use in step (f) flanking sequences of sufficient length comprising a gene that can be disrupted without affecting colonization and immunity of *Vibrio cholerae*. An example is the hemolysin gene. *V. cholerae* CVD110 and CVD111 were constructed according to this method, and have a region of chromosomal DNA coding for A and B subunits of cholera toxin and zonula occludens toxin deleted, and have a mercury resistance gene and DNA coding for B subunit of *Vibrio cholerae* toxin inserted at the site of hemolysin gene. Other examples of sequences of sufficient length comprise the his gene (Hone, *Microbial Pathogenesis* 5, pp. 407–478 (1989)) and the nanH gene (Vimr, *J. Bacter.*, 170, pp. 1495–1504 (1988)).

The invention also relates to strains, vaccines and method of making these strains and vaccines which comprise *V. cholerae* of a non-O1 serogroup. One of these strains, CVD112, has a deletion entire cholera toxin core region, which comprises cep, ace, zot, orfU, and ctxAB as well as deletion of the RS1 elements and attRS1 sites [Pearson et al., *Proc. Natl. Acad. Sci. (USA)*, 90, pp. 3750–3754, 1993] with the ctx chromosomal locus. In addition, these strains have sequences encoding a sufficient part of the cholera toxin B subunit to confer immunogenicity re-inserted into the vibrio chromosome. Addition inserted into the chromosome are sequences which confer resistance to heavy metals, such as mercury.

Another *V. cholerae* non-O1 strain of the invention, namely CVD112 RM has the identifying characteristics of the above-mentioned non-O1 strain, and additionally has a deletion in the *Vibrio cholerae* recA locus such that the resultant strain is deficient in homologous recombination.

In the examples that follow, any of the techniques, reactions, and separation procedures are already well known in the art. All enzymes, unless otherwise stated, are available from one or more commercial sources, such as New England BioLabs—Beverly, Mass.; Collaborative Research—

Waltham, Mass,; Miles Laboratories—Elkhart, Ind.; Boehringer Biochemicals Inc.—Indianapolis, Ind.; and Bethesda Research Laboratory—Rockville, Md., to mention a representative few. Buffers and reaction conditions for restriction enzyme digestion are used according to recommendations supplied by the manufacturer for each enzyme, unless indicated otherwise. Partial digestions with restriction enzymes are carried out using a reduced enzyme concentration which must be predetermined from preliminary experiments for each enzyme batch. Standard methodology for other enzyme reactions, gel electrophoresis separations, and *E. coli* transformation may be found in *Methods in Enzymology* Volume 68, Ray Wu, editor, Academic Press (1979). Another standard reference is Maniatis, T. et al. *Molecular Cloning*, Cold Spring Harbor (1982). Bacteria were grown according to procedures generally described in Miller, *Experiments in Molecular Genetics*, Cold Spring Harbor Laboratory (1972) *Vibrio cholerae* were propagated according to procedures generally described in Lennett, E. A. et al., eds., *Manual of Clinical Microbiology* 3rd Edition, American Society of Microbioloy, Washington (1980). *E. coil* and *V. cholerae* were mated according to procedures generally described in Johnson, Steven R. et al. *J. Bact.* 137, 531 (1979); and Yokata, T. et al. *J. Bact.* 109, 440 (1972).

The strains of this invention have been deposited at the American Type Culture Collection, located in Rockville, Md., prior to execution of the present application. The strains deposited are *V. cholerae* JBK56, *V. cholerae* JBK70, *V. cholerae* N1696, *V. cholerae* JVK70 (pJBK51), *V. cholerae* Ogawa 395, CVD101, CVD109, *V. cholerae* E7946, and *E. coli* SM10 lambda pir pCVD51, *V. cholerae* CVD110, and *E. coli* SY327 lambda pir (pCVD622.2B), which have ATCC accession numbers 39,317, 39,318, 39,315, 39,316, 39,541, 39,540, 55,057, (deposited Jun. 4th, 1990), 55,056 (deposited Jun. 4th, 1990), 68,335 (deposited Jun. 5th, 1990), 55188 (deposited Jun. 3rd, 1991), and 68630 (deposited Jun. 3rd, 1991, respectively.

EXAMPLE 1

Construction of a Plasmid Having a Selectable Marker Gene Inserted to Replace the Toxin Genes The plasmid JBK16 contains a 4 kb PstI-BglII fragment of the chromosome containing the toxin genes. The toxin genes are flanked by AccI sites and contain an internal AccI site. JBK16 was digested to completion with AccI and the AccI fragments containing the toxin genes were separated from the rest of the plasmid. The remaining overlapping or "sticky" AccI ends were made blunt-ended by "filling in" with the Klenow fragment of *E. coli* polymerase (i.e., the single-stranded DNA remaining after AccI digestion were made double-stranded with flush ends). A gene encoding ampicillin resistance was purified from the plasmid pREG153 (pREG153 is a derivative of pREG151 [Weiss, A. et al. *J. Bact.* 152, 549–552] altered by substitution of ampicillin resistance for trimethoprin resistance and addition of cos sequences) and the "sticky" ends "filled in" as above. This fragment was then ligated to the vibrio DNA so that the Ap resistance genes were in exactly the same place as the now-deleted toxin genes, flanked by the same vibrio sequences. The resulting plasmid was designed pJBK21 (FIG. 4) containing the deletion toxin region and the Ap resistance gene.

EXAMPLE 2

Addition of Flanking Homologenous Sequences Followed by Conjugal Gene Transfer into *V. Cholerae*

To insure the specific insertion into the chromosome of the deletion in pJBK21, approximately 7,000 bp of additional DNA was added to each end of the PstI-BglII fragment from pJBK21. (The probability of the homologous recombination event occurring increases with increasing length of flanking homologous sequences.) To achieve this, an approximately 18 kb fragment was cloned from the chromosome of N16961. This clone was designated pJBK44 and contains the 4 kb PstI-BglII tox gene fragment flanked by approximately 7 kb of DNA on each side (see FIG. 5). The plasmid pJBK21 was partially digested with PstI so that only one of the Pst sites would be cut (an additional Pst site was added within the ampicillin resistance gene) followed by digestion with BglII to isolate the 4 kb PstI-BglII fragment containing the deletion toxin region and the Ap resistance region. The plasmid pJBK44 containing the ca. 18 kb Vibrio fragment was partially digested with BglII so that only one of the 4 BglII sites present would be cut. This partial digestion was followed by complete digestion with PstI and the resulting fragments separated by electrophoresis through 0.3% agarose. The separated fragments were then purified and analyzed and one fragment was found which contained all of the sequences of pJBK44 except for the 4 kb. PstI-BglII tox gene fragment (see FIG. 5.). This fragment representing the flanking DNA was then mixed ligated to the PstI-BglII fragment from pJBK21 containing the ampicillin resistance. The resulting plasmid, pJBK54, contained approximately 17 kb of Vibrio chromosomal DNA with an ampicillin resistance gene substituted for the deleted toxin genes.

The modified chromosomal region was then cloned into a plasmid which can be readily mobilized in *V. cholerae*. The plasmid pRK290 [Ditta, G. et al. *Proc. Nat. Acad. Sci.* 77, 7347 (1980)] belongs to the plasmid incompatibility group P and possesses a single EcoRI site into which pJBK54 was cloned (FIG. 6). The resulting plasmid pJBK55 was then mated into *V. cholerae* N16961 using the conjugative plasmid pRK2013, yielding *V. cholerae* N16961 (pJBK55) ($Ap^r$).

EXAMPLE 3

Recombination in vivo

The mutant toxin genes, after conjugal gene transfer as described in Example 2, now existed extrachromosomally in *V. cholerae* strain N16961 (see FIG. 1). At a very low frequency (perhaps $10^{-6}$ to $10^{-8}$) the homologous flanking sequences base pair and cross over into the chromosome (see FIG. 7). This rare event will result in the substitution of the deleted toxin region on the plasmid for the ctx genes on the chromosome. To select for this rare event, the plasmid incompatibility phenomenon was exploited [Ruvkin, G. B., supra]. Plasmids can be divided into incompatibility groups, designated A through W, on the basis of their ability to be stably maintained together in the same cell. If two plasmids cannot be stably maintained together in the same cell, they are incompatible and belong to the same incompatibility group presumably because they utilize the same replication mechanism in the cell. By selectively using an antibiotic resistance present on one plasmid but not on the other, it is possible to select which of two incompatible plasmids will be maintained The plasmid pJBK55, because of its pRK290 origin, belongs to the (Inc) group P. The plasmid R702 also belongs to the Inc P group and encodes resistance to kanamycin, tetracycline, sulfonamide, and streptomycin, but not ampicillin. By mating pR702 ($Su^R$) into N16961 (pJBK55) ($Ap^R$) and selecting on media containing both ampicillin and sulfonamide, selection was made for cells in which the ampicillin resistance had been incorporated into the chromosome and sulfonamide resistance remains on the plasmid R702, since pR702 and pJBK55 are incompatible (see FIG. 2). The resultant strain JBK56 (FIG. 3) was ampicillin resistant, and toxin negative when tested in Y-1 adrenal cells and by $Gm_1$ ELISA. Furthermore, when chromosomal DNA was hybridized to DNA probes containing clone cholera toxin (CT) genes, JBK56 was negative, suggesting that the toxin genes were completely deleted.

Figure 9:
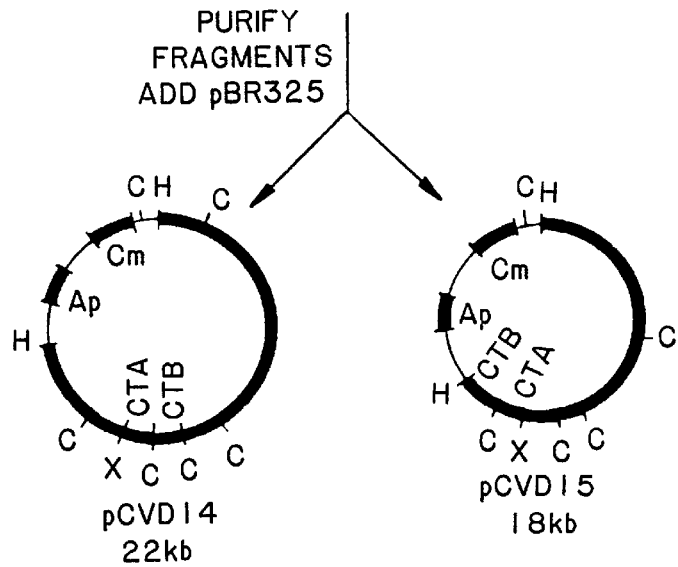
FIG. 9. Scheme for construction of pCVD14 and pCVD15.

The antibiotic resistance encoded on R702 was eliminated by selecting a spontaneously cured derivative lacking the plasmid (this occurred at a frequency of about 1 in 2,000).

EXAMPLE 4

Elimination of the Selectable Marker of Example 1

To eliminate the ampicillin resistance, a derivative of pJBK55 was constructed in which genes encoding resistance to mercury (Hgr) from R100 were cloned into the PstI site of the Ap gene, thereby insertionally inactivating the ampicillin resistance. This derivative was then mated into *V. cholerae* JBK56, followed by pR702 and selection made as above for $Hg^r$, $Ap^s$ *V. cholerae*. The final strain, *V. cholerae* JBK70, is sensitive to all antibiotics tested, resistant to mercury, and phenotypically toxin negative. Its chromosomal DNA did not detectably hybridize to DNA probes containing CT genes. Short of sequencing the DNA for the entire chromosome, JBK70 appears to be unaltered from the parent strain N16961 except for the deletion of the toxin genes and insertion of mercury resistance and inactive ampicillin resistance genes. Such a strain cannot revert to toxigenicity because the toxin genes are not merely mutated but are completely deleted.

EXAMPLE 5

Conjugal Gene Transfer to Confer Antitoxic Immunity

If both antibacterial immunity and antitoxic immunity are desired for synergy, a derivative of JBK70 can be made to produce the B subunit of cholera toxin only. To accomplish this end, a toxin derivative was made that produces B only and lacks the genes for A (FIG. 8). A HpaII fragment from pJBK16 containing the B structural gene was cloned into a phage cloning vector, M13mp7 placing a BamHI and an EcoRI site on either side of the gene (FIG. 8). The fragment, now flanked by BamHI sites was cloned into pMS 9 which contains the very strong trp promoter. The placing of the B genes under the transcriptional control of a strong promoter insures high production of B antigen. Of the clones examined, approximately 50% produced no antigen. This finding reflects the two possible orientations for the cloned insert—one forward, one backward. One derivative, pJBK51, which produced B subunit was mated into *Vibrio cholerae* JBK70 and found to produce even more B antigen then the parent strain N16961, yielding JBK70 (pJBK51). Other B-only mutants have been created using different promoters, including the $P_L$ promoter and these can be evaluated in appropriate models for any significant in vivo expression differences.

EXAMPLE 6

Colonization of Infant Mouse Intestine with JBK70 without Reversion to Toxigenicity Suckling mice (2.0–3.5 g.) were removed from their mothers and starved for 3 to 8 hours. Four of them were then inoculated on day 1 per os to stomach using a 22 g animal feeding needle. The inoculum was about $10^8$ CFU (colony-forming units)/mouse of JBK70 in a volume of between 0.05 ml and 0.1 ml. The inoculum was prepared in BHI broth essentially as described in Baselski, V. et al, supra. The inoculum contained about 0.01% Evans blue dye. The presence of this dye in the stomach, seen through the abdominal wall, indicated proper delivery of the inoculum. Addition of Evans blue dye was discontinued after day 1, to avoid inhibition of JBK70.

Subsequent inoculations involved mouse-to-mouse (MXM), or alternatively, mouse-to-plate-to-mouse (MXPXM), but required different procedures to prepare the inoculum compared to the Baselski protocol for the inoculation on day 1.

To prepare MXM inoculum, the gut was dissected from stomach to anus under sterile precautions. The gut was weighed, placed in a glass homogenizer tube, and about 0.5 ml BHI broth added. The mixture was homogenized briefly with a Teflon pestle until tissue was liquified. The resulting suspension was used to inoculate about $10^8$ CFU into each infant mouse. It was checked for purity by streaking on MEA (meat extract agar) plates. No Evans blue dye was added.

To prepare MXPXM inoculum, a sterile loop was used to transfer cells from an MEA plate to BHI broth. About $10^{11}$ CFU/ml were added to about 1 ml of BHI so that a dense suspension was formed. The mixture was vortexed to homogeneity, and 0.05–0.1 ml. (about $10^{10}$ CFU) inoculated per os into each infant mouse. No Evans blue dye was added.

For all inoculations, mice were held in beakers at room temperature of 73°–76° F. Beakers were placed in a plastic box which was loosely covered in order to maintain the mice at slightly above ambient temperature, about 78° F.

As the results in Table I indicated, there were sufficient cells in the intestine to inoculate the next animal, as checked by streaking on MEA plates. The *Vibrio cholerae* JBK70 therefore colonized the gut of infant mice. Furthermore, the fluid accumulation levels did not increase since there were no substantial increases in the FA ration (an FA ratio greater than or equal to 0.065 is a positive fluid accumulation). Evidence of reversion to toxigenicity would have indicated otherwise.

EXAMPLE 7

Construction of *V. cholerae* strain CVD101 having a Restriction Fragment Deletion within the Gene coding for the A Subunit Another classical strain chosen for attenuation was *Vibrio cholerae* Ogawa 395 (alternatively designated "395") which, like N16961, has been extensively studied in volunteers and confers solid immunity [Levine, M. M. "Immunity to cholera as evaluated in volunteers," in *Cholera and Related Diarrheas: 43rd Nobel Symposium*, Stockholm 1978. (O. Ouchterlong & J. Holmgren, eds.) Basel: S. Karger, pp. 195–2–3 (1980); Levine, M. M et al. *Acute Enteric*, supra (1981)]. The procedure employed in the attenuation of 395 was not substantially different from that employed for N16961. (as described in Examples 1–5).

The first step involved the cloning and mapping of the two toxin gene copies of 395. Southern blot analysis revealed two HindIII fragments of about 16 and about 12 kb in length, both of which hybridized with cloned cholera toxin genes. These fragments were purified by agarose gel electrophoresis and cloned into alkaline phosphates treated HindIII digested pBR325 (FIG. 9). The resulting recombinant plasmids containing the toxin genes were designated pCVD14 and pCVD15.

Figure 10:
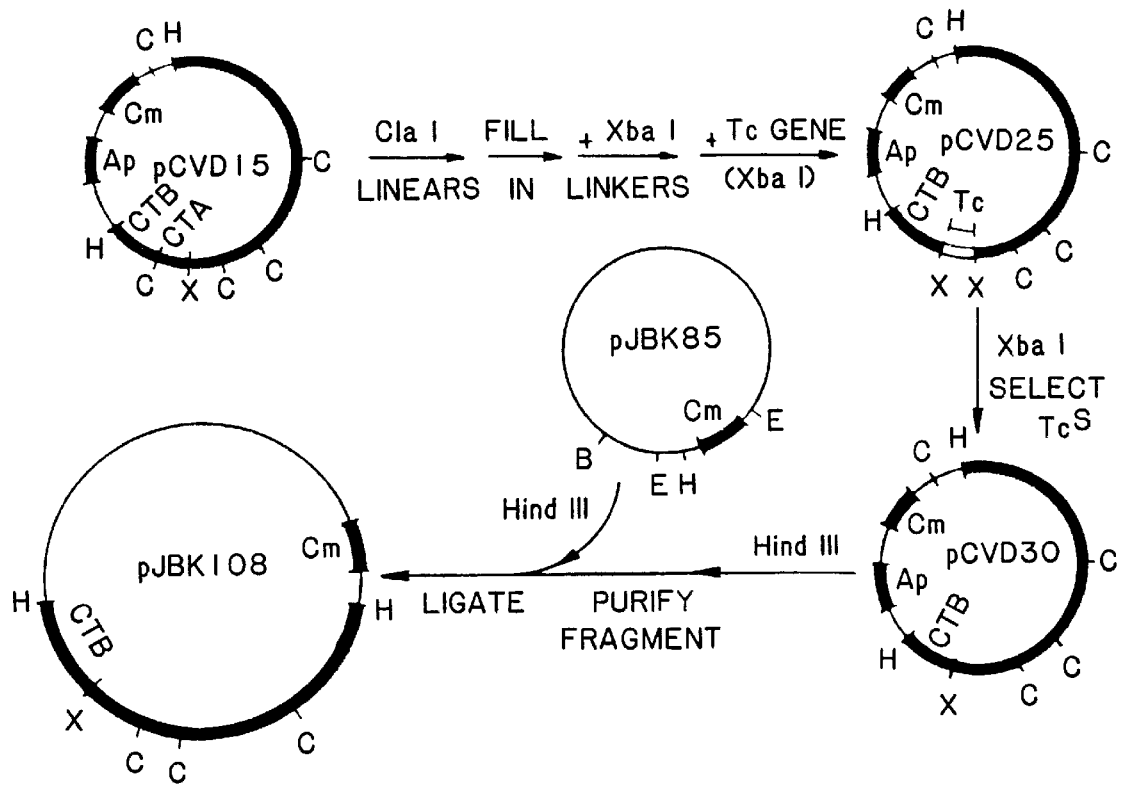
FIG. 10. Scheme for construction of pJBK108.

Plasmids pCVD14 and pCVD15 were then mapped with restriction endonucleases. A XbaI-ClaI fragment of about 550 bp was found, containing the entire base sequence of the $A_1$ subunit with the exception of codons for the first 10 amino acid residues of $A_1$. This XbaI-ClaI fragment was deleted in vitro from both pCVD14 and pCVD15 in a series of steps as shown in FIG. 10 for pCVD15. First, partial digestion with ClaI yielded a population of linear molecules in which only one of five ClaI sites was cut. Next, the ends of the linear molecules were made blunt-ended by filling in with DNA polymerase. XbaI linkers were ligated onto the blunt-ended ClaI sites yielding a collection of molecules to which a XbaI enzyme was added to trim the linker, and a tetracycline resistance gene on a XbaI fragment was added and ligated. After transformation into *E. coli* K-12 and selection on tetracycline, the plasmid content of a number of transformants was examined. A variety of deletion mutations were found in which one or more XbaI-ClaI fragments were deleted. One deletion mutant was chosen which lacked only the 550 bp XbaI-ClaI fragment containing the $A_1$ gene. This deletion mutant, designated pCVD25 was purified, digested with XbaI and religated to delete the tetracycline resistance gene. The resulting clone, pCVD30, was negative for holotoxin as measured in Y-1 adrenal assay [Sack, D. A. et al. supra (1975)], but positive for production of B subunit, as measured by ELISA [Sack, D. A. et al. supra (1980)], and lacked the genes for $A_1$, as shown by DNA hybridization using labeled $A_1$ probe. The HindIII fragment of pCVD30 containing the toxin deletion mutation was then cloned into pJBK85, a Tc sensitive, Cm resistant derivative of pJBK108. The resulting plasmid was designated pJBK108.

Figure 11:
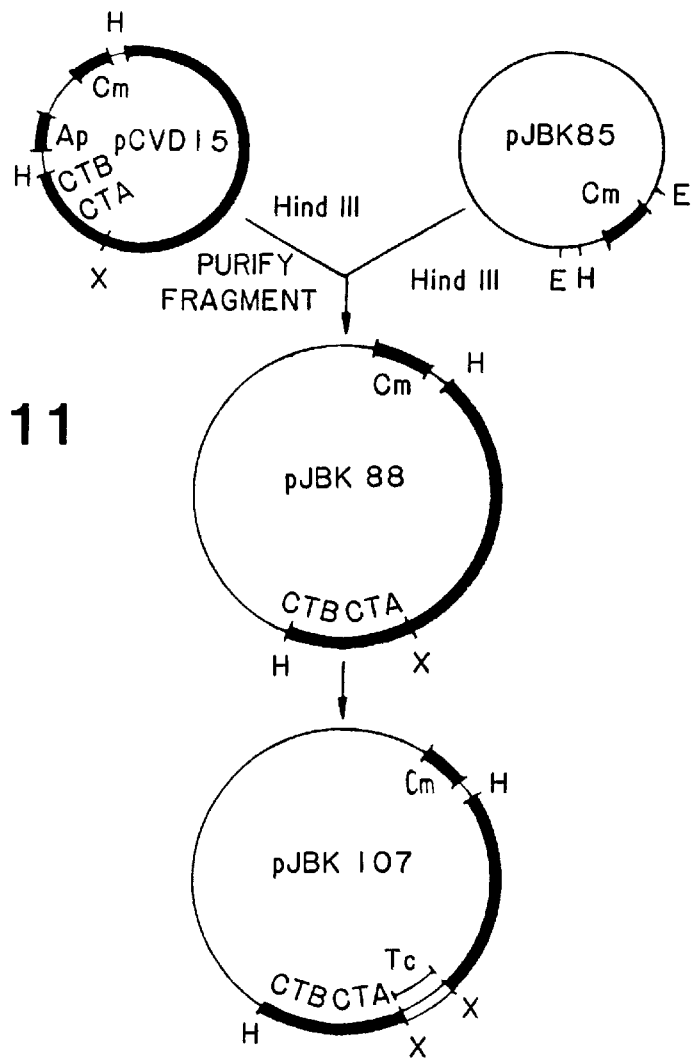
FIG. 11. Scheme for construction of pJBK107.

The lack of selectable marker in the toxin deletion mutation in PJBK108 necessitated a modification of the method previously used to attenuate El Tor N16961. To accomplish the deletion of the $A_1$ genes from 395, the HindIII fragment from pCVD15 was cloned into PJBK85, resulting in pJBK88 (FIG. 11). The tetracycline resistance gene on a XbaI fragment was then cloned into the XbaI site within the $A_1$ gene of PJBK88, yielding pJBK107. This tetracycline resistance gene was then recombined into the chromosome of 395 as previously done for *V. cholerae* pJBK56. PJBK107 ($Tc^r$, $Cm^r$) was mobilized into 395 and a second Inc P plasmid, pR751 ($TP_r$) was introduced. Selection of $Tc^r$, $Tp^r$ $Cm^s$ colonies resulted in *V. cholerae* JBK113, which contained tetracycline resistance genes in both chromosomal toxin gene copies. pJBK108, containing the deletion mutation, was then mobilized into *V. cholerae* JBK113. Homologous recombination of the deletion mutation into the chromosome will result in the loss of the $A_1$ gene sequences, an event which can be detected by loss of tetracycline resistance. Because the recombination even occurs at a very low frequency, an enrichment procedure for tetracycline sensitive cells in a population of tetracycline resistant cells was employed. This enrichment procedure exploited the fact that tetracycline is a bacteriostatic antibiotic whereas ampicillin and D-cyclo-serine are bactericidal. Therefore, a culture of *V. cholerae* JBK113 containing pJBK108 was grown for 3 hr at 37° in L-broth containing 2 micro g/ml tetracycline, 50 micro g/ml ampicillin and 50 micro g/ml D-cycloserine. At the end of 3 hours, most of the tetracycline resistant cells were killed, and tetracycline sensitive cells were detected by plating onto L-agar and replica plating onto L-agar with tetracycline. Tetracycline sensitive colonies were probed for the presence of $A_1$ genes by DNA hybridization. One tetracycline sensitive strain having deletions for both gene copies of the $A_1$ subunit was designated *V. cholerae* CVD101 and tested for production of B subunit by ELISA [Sack, supra]. *V. cholerae* CVD101 was found to produce B subunit antigen at levels substantially equivalent to the toxigenic parent *V. cholerae* 395.

EXAMPLE 8

DNA sequence of the Toxin Genes

Figure 12:
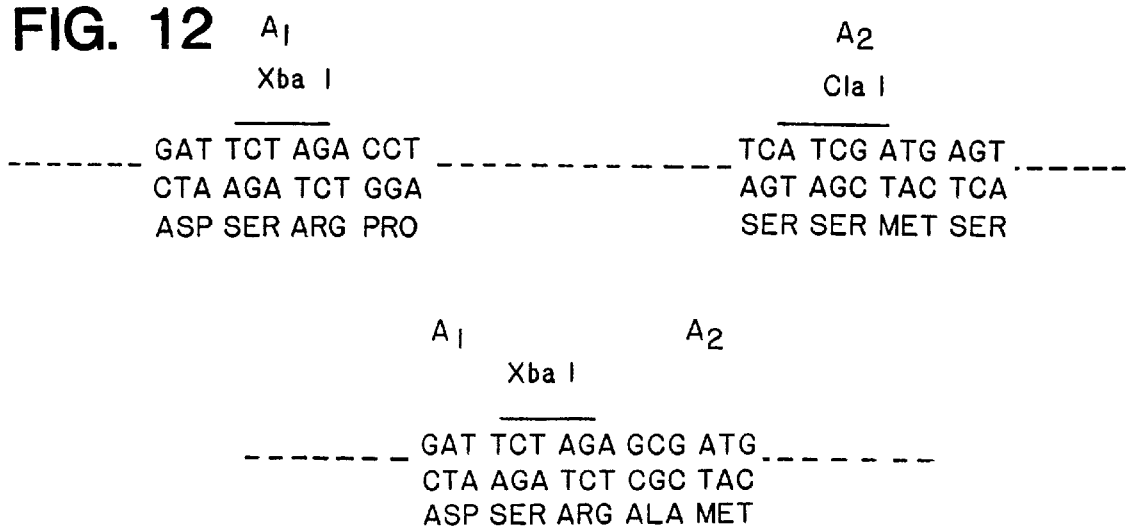
FIG. 12. DNA sequences and corresponding amino acid sequences of (top) the XbaI and ClaI sites, which determine the ends of the deleted XbaI-ClaI 550 bp fragment of the A subunit in Ogawa 395 (SEQ ID Nos. 9–12), and for (bottom) the junction in CVD101 after deletion of this fragment and insertion of a XbaI linker (SEQ ID Nos. 13 and 14).

The entire DNA sequence of the toxin genes of *V. cholerae* Inaba 62746 has been determined, part of which has been reported by Lockman, et al., J. Biol. Chem. 258, 13722 (1983). The restriction endonuclease mapping of pCVD14 and pCVD15 indicates that the sequences found in strain 62746 are also present in the toxin genes of 395. The predicted junction after deletion of the 550 bp XbaI-ClaI fragment, but with addition of a XbaI linker sequence, is shown in FIG. 12. The XbaI site of the cholera toxin sequence span amino acid residues 10 and 11 of the $A_1$ structural gene (not counting the 18 amino acid leader sequence for $A_1$.

EXAMPLE 9

Construction of a *V. Cholerae* Strain Having a Zonal Occludens Toxin Deletion in CVD101

A zot deletion mutant of *V. cholerae* is prepared in the same way as the CVD101 cholera toxin deletion mutant described in Example 7. The zot gene is contained in the recombinant plasmid pBB68. pBB68 consists of an EcoRI-PbrI chromosomal DNA fragment from *V. cholerae* 569B which contains the zot gene and the ctx genes which have a deletion of a 550 bp XbaI-ClaI fragment. A StuI-AccI restriction fragment of 575 base pairs is deleted in vitro from pBB68 by digesting with the restriction enzymes StuI and AccI, and making the ends of the molecules blunt-ended by filling in with DNA polymerase. (This will remove 48% of the 1199 base par zot gene). One half of the sample is ligated to a tetracycline resistance gene (of foreign origin), these giving a selectable marker.

The zot deletion mutant constructed in vitro above is introduced into the chromosome of *V. cholerae* CVD101 as previously described for the construction of the ctx deletion mutant of CVD101. The tetracycline resistant clone derived above is cloned into the Inc P plasmid pJBK85. This plasmid ($Tc^r$, $Cm^r$) is mobilized into CVD101, selecting for $Tc^r$. A second Inc P plasmid, pR751 ($Tp^r$) is introduced. Selection of $Tc^r$, $Tp^r$, $Cm^s$ colonies result in *V. cholerae* strains in which the $Tc^r$ gene has recombined into the zot gene.

The plasmid containing the StuI-AccI deletion mutant without the $Tc^r$ gene is then mobilized into the $Tc^r$ *V. cholerae* strain. Homologous recombination of the deletion mutant into the chromosome results in the loss of the zot gene sequences, an event which can be detected by loss of $Tc^r$. $Tc^s$ colonies are selected and screened for loss of zot sequences by DNA hybridization using the StuI-AccI fragment as a probe.

EXAMPLE 10

Construction of CVD109—a *V. Cholera* Strain deletions of Sequences coding for *V. Cholera* Toxins and for Zonula Occludens Toxin The construction of attenuated *V. cholerae* strain CVD109 (ATCC# 55057) involves in introduction of cloned Vibrio sequences along with sequences encoding a selectable marker into the chromosome of a virulent *V. cholerae* strain. An initial in vivo recombination event of homologous sequences from the recombinant plasmid into the chromosome provides a selectable marker at this site. A second in vivo recombination event between homologous flanking sequences results in excision of proficient genes from the chromosome with the end product being a deletion mutation.

FIG. 16 illustrates the construction of CVD109. The zot and ctx genes are adjacent to each other on the *V. cholerae* chromosome. Multiple copies of a 2700 base pair DNA sequence called RS1 (for repetitive sequence) are on both sides of the zot and ctx genes in virulent *V. cholerae* strain E7946 (El Tor biotype, Ogawa serotype). In FIG. 16A, the zot and ctx sequences are shown by a large open or hash-marked arrow. RS1 sequences are shown by a smaller, solid arrow.

Figure 16A:
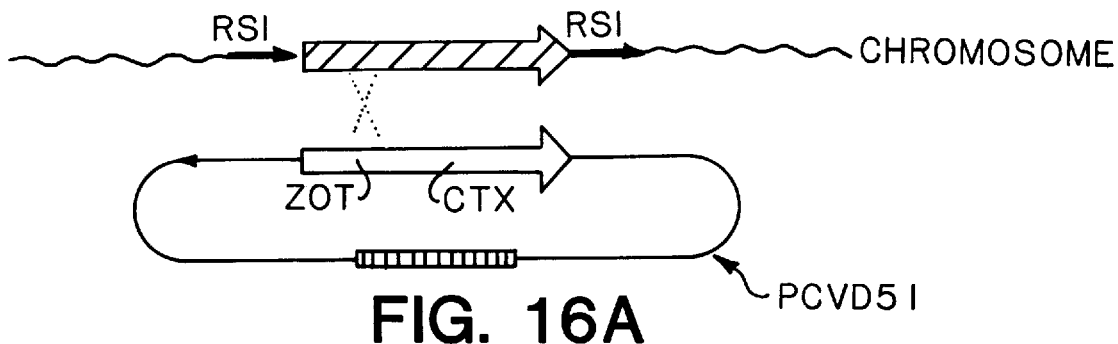
Figure 16B:
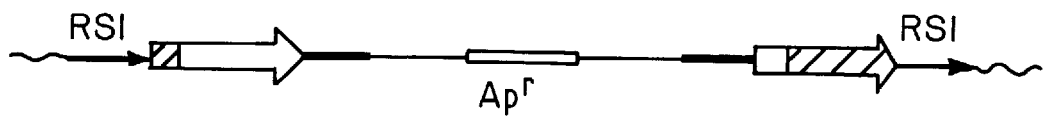

The recombinant plasmid, pCVD51 (FIG. 16A), contains cloned zot/ctx sequences (open arrow) which are homologous to the chromosomal zot/ctx sequences (shown by hash-marked arrow in FIG. 16A) and contains a selectable marker, ampicillin resistance ($Ap^r$). The plasmid vector into which the Vibrio sequences were cloned is pGP704 (Miller and Mekalanos *J. Bact.* 170, 2575–2583 (1988)). This plasmid cannot replicate extrachromosomally in *V. cholerae* but can replicate in permissive *E. coli* strains. pCVD51 was mated from *E. coli* to *V. cholerae* E7946. Since this plasmid cannot replicate extrachromosomally in *V. cholerae*, selection of $Ap^r$ colonies yielded strains in which the entire plasmid, with the $Ap^r$ marker, was homologously recombined into the chromosome at the site of the zot/ctx sequences. (The exact site of recombination, whether in zot or ctx gene, is not known.) The result of this single cross over (not double cross over) event is termed a "cointegrate" structure and is depicted in FIG. 16B.

Figure 16C:
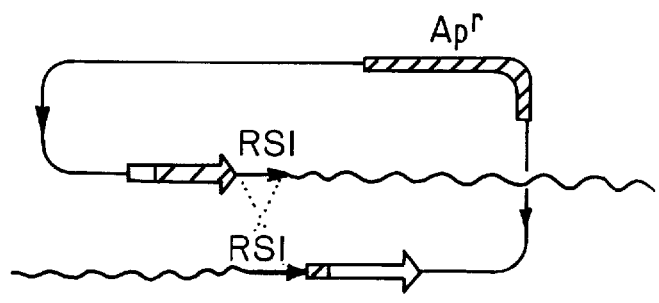

The RS1 sequences flanking the zot/ctx region are of sufficient length to provide detectable in vivo recombination; intra-molecular recombination between the homologous RS1 elements results in the loss of all sequences between them. The $Ap^r$ *V. cholerae* with the integrated plasmid was grown in the absence of ampicillin and the Ap sensitive ($Ap^s$) colonies were selected. Recombination of the RS1 elements flanking ctx and zot resulted in the loss of the intervening zot and ctx sequences along with the plasmid vector containing $Ap^r$ (FIG. 16C).

Figure 16D:
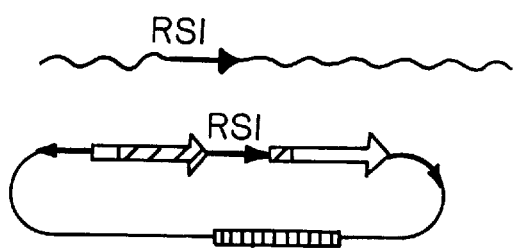

The Aps *V. cholerae* colonies resulting from the above steps were screened by DNA hybridization for zot sequences. The DNA probe consisted of a 575 base pair StuI-AccI restriction fragment derived from the cloned zot gene. Colonies which did not hybridize to this probe were selected and probed for the presence of ctx genes by DNA hybridization using a ctx gene probe. The hybridization results confirmed the loss of both the zot and ctx genes. One representative strain was saved and designed CVD109. FIG. 16D depicts the chromosome of CVD109 which is deleted of zot and ctx sequences but retains one copy of the RS1 element. (The plasmid shown in FIG. 16D is not retained in the final $Ap^s$ strain but is depicted only to illustrate the outcome of the second cross-over event. This transient product is spontaneously lost since the plasmid cannot replicate extrachromosomally in *V. cholerae*.)

EXAMPLE 11

Construction of CVD110—a *V. Cholerae* Strain Having Deletions of Sequences Coding For A and B Subunits of *V. cholerae* Toxin and for Zonula Occludens Toxin, and Having Inserted a Mercury Resistance Gene and DNA Coding for B Subunit of *V. Cholerae* Toxin CVD110 (ATCC# 55188) was constructed directly from *V. cholerae* CVD109, the description of which has already been provided. *V. cholerae* CVD109 lacks both the A and B subunits of cholera toxin (CT) as well as the gene encoding zot and is sensitive to mercury. A gene fragment that contains the CT B subunit gene (ctxB) and a mercury resistance gene was constructed in vitro. This construction was then inserted into the chromosome of CVD109, specifically into the hemolysin gene. Thus, the final vaccine strain, CVD110, produces the B but not the A subunit of cholera toxin, is resistant to mercury and does not produce wild type HlyA protein (hemolysin).

Figure 18:
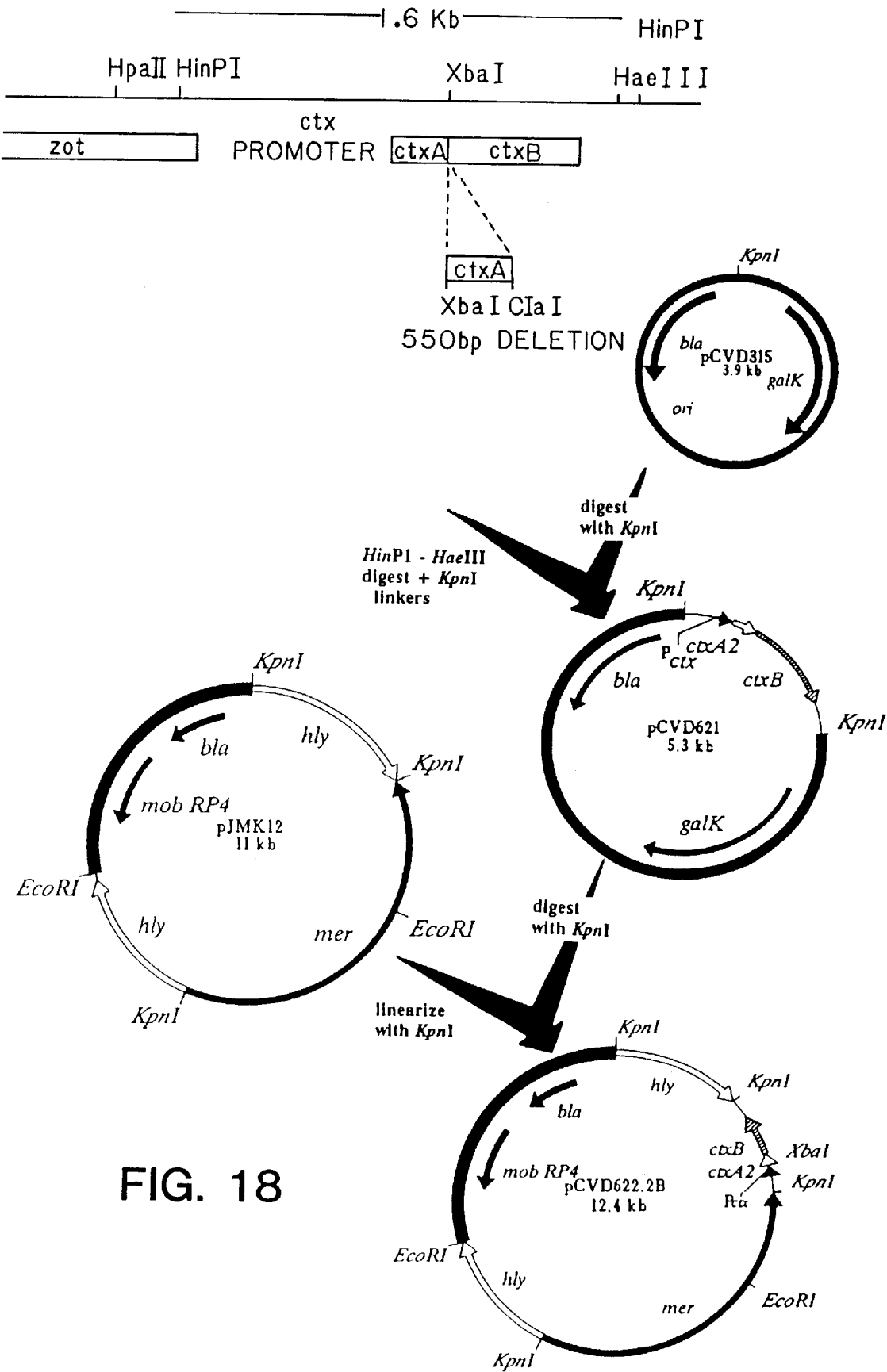

CT B construction: The ctxB and ctx promoter sequences were obtained from plasmid pCVD30, which is described in Example 7. This plasmid pCVD30 contains a deletion of the ctxA gene. A 1.4 kilobase fragment containing the ctxB gene and the ctx promoter but not the zot gene was obtained by digesting pCVD30 with HinP1 and HaeIII enzymes. The fragment was treated with T4 DNA polymerase to render the ends of this fragment blunt-ended and synthetic KpnI linkers were ligated to this fragment. The fragment was then cloned into the vector pCVD315 [Galen, et al. Advances in Research on Cholera and Related Diarrheas, vol. 7 (Sack et al., Eds.) pp. 143–153 (1990)] Vector pCVD315 has no particular significance for this purpose other than the presence of a KpnI site. The resulting plasmid containing the ctxb gene was called pCVD621 (FIG. 18).

Mercury resistance genes: The source of the mercury resistance genes (mer) was the same as that used for *V. cholerae* JBK70. A 4.2 kb NcoI-StuI fragment containing mer was originally derived from pDB7 [Barrineau, et al. J. Molecular & Applied Genetics (1984) vol. 2, pp.601–619]. The fragment was treated with DNA polymerase (Klenow fragment) to render the ends of this fragment blunt-ended and synthetic KpnI linkers- were ligated to this fragment. The fragment was then cloned into plasmid pCVD43.2 (unpublished), which is a derivative of pCVD43 [Kaper, et al. Advances in Research on Cholera and Related Diarrheas, vol. 6 (Ohtomo, et al., Eds.) pp. 161–167 (1988)]. pCVD43 contains the cloned hemolysin genes (hlyA) of *V. cholerae* without a 400 bp HpaI fragment internal to hlyA. The deletion of the 400 bp HpaI fragment renders the gene inactive [Kaper, et al. Advances, etc. vol. 6]. pCVD43.2 is identical to pCVD43 except that a synthetic KpnI linker has been ligated into the single HpaI site of pCVD43. The combined clone of the mer genes inserted into the hylA gene is called pCVD43.3.

Figure 19A:
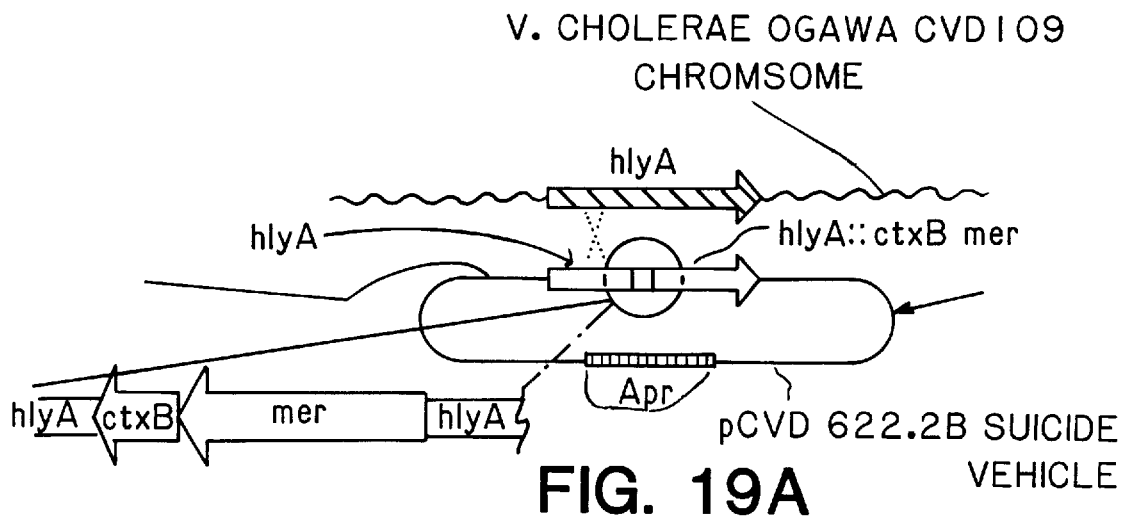
Figure 19B:
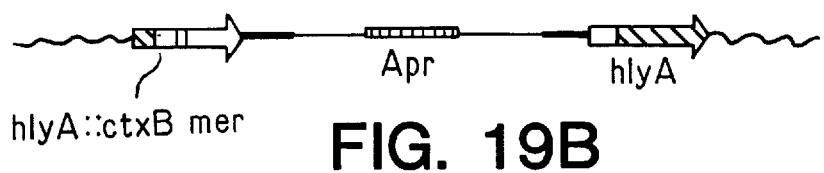

Insertion of ctxB and mer genes into CVD109: To introduce these genes into the chromosome of CVD109, plasmid vector pGP704, which is described in Example 10, was used. An 8.1 kb ClaI-BglII fragment from pCVD43.3 containing mer and hylA was cloned in pGP704 to produce pJMK12 (FIG. 18). pJMK12 was partially digested with KpnI to yield a population of linear molecules in which only one of 3 KpnI sites was cut. The 1.4 kb fragment of pCVD621 (described above) containing the ctxb gene was then ligated to pJMK12 to yield pCVD622.2B. The relative position and orientation of the inserted genes is shown in FIG. 18.

pCVD622.2B was then introduced into *V. cholerae* CVD109 by conjugation from an *E. coli* host strain. As described in Example 10, pGP704 cannot replicate extrachromosomally in *V. cholerae* but can replicate in permissive *E. coli* strains. Since pCVD622.2B cannot replicate extrachromosomally in *V. cholerae*, selection of $Ap^r$ colonies [pGP704 contains a gene encoding ampicillin resistance] yielded strains in which the entire pCVD622.2B plasmid, with the Apr marker, was homologously recombined into the chromosome at the site of the hylA gene. [It could not recombine into the ctx or zot sequences because CVD109 lacks these genes.] The result of this single cross-over (not double cross-over) event is termed a "cointegrate" structure or "Merodiploiod" (these terms are used interchangeably) and is depicted in FIG. 19B.

Figure 19C:
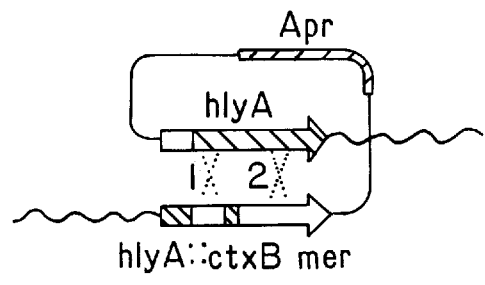
Figure 19D:
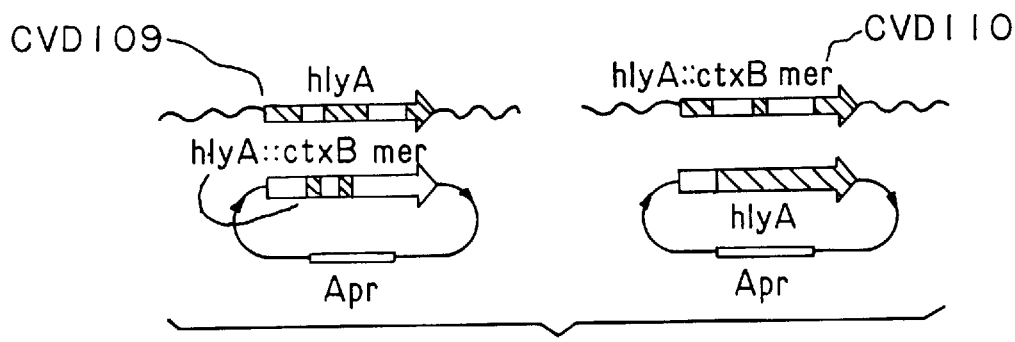

A second cross-over event can occur between the homologous hylA sequences flanking the integrated pCVD-622.2B. This second cross-over event occurs spontaneously and is detected by selection of colonies which have lost the Ap$^r$ phenotype. This second cross-over event can have one of two possible outcomes, depending upon the exact site of recombination. Both possible outcomes result in the loss of the pGP704 plasmid vector sequences and are depicted in FIGS. 19C and 19D. One outcome simply re-generates the original situation, i.e., a strain identical to CVD109 which lacks ctx, zot, and mer. The second outcome results in the lost of pGP704 sequences but the mer and ctx sequences contained within the hlyA sequences are retained. The two possible outcomes are readily distinguished by DNA hybridization using radiolabeled ctx sequences as a probe. To isolate the desired outcome, a culture of CVD109 containing the integrated pCVD622.2B was grown up in L-broth without added antibiotics. This culture was plated on non-selective L-agar plates and the resulting colonies were replicated onto Ap containing L-agar plates. Ap$^s$ colonies were then hybridized to the ctx probe and colonies possessing ctx sequences were isolated. One such colony was designated *V. cholerae* CVD110. This strain was confirmed by DNA hybridization to contain ctx and mer sequences and to also lack pGP704 sequences and the 400 bp HpaI fragment internal to the hlyA gene. *V. cholerae* CVD110 was also confirmed to produce the B subunit of cholera toxin by ELISA [Sack, D. A. et al. supra (1980)].

DNA sequence of inserted genes: The exact DNA sequences of the inserted ctx and mer genes are known from the literature. The exact site of the hlyA gene into which these genes were inserted is also known.

EXAMPLE 12

Description of ACE (Accessory Cholera Enterotoxin)

Figure 20:
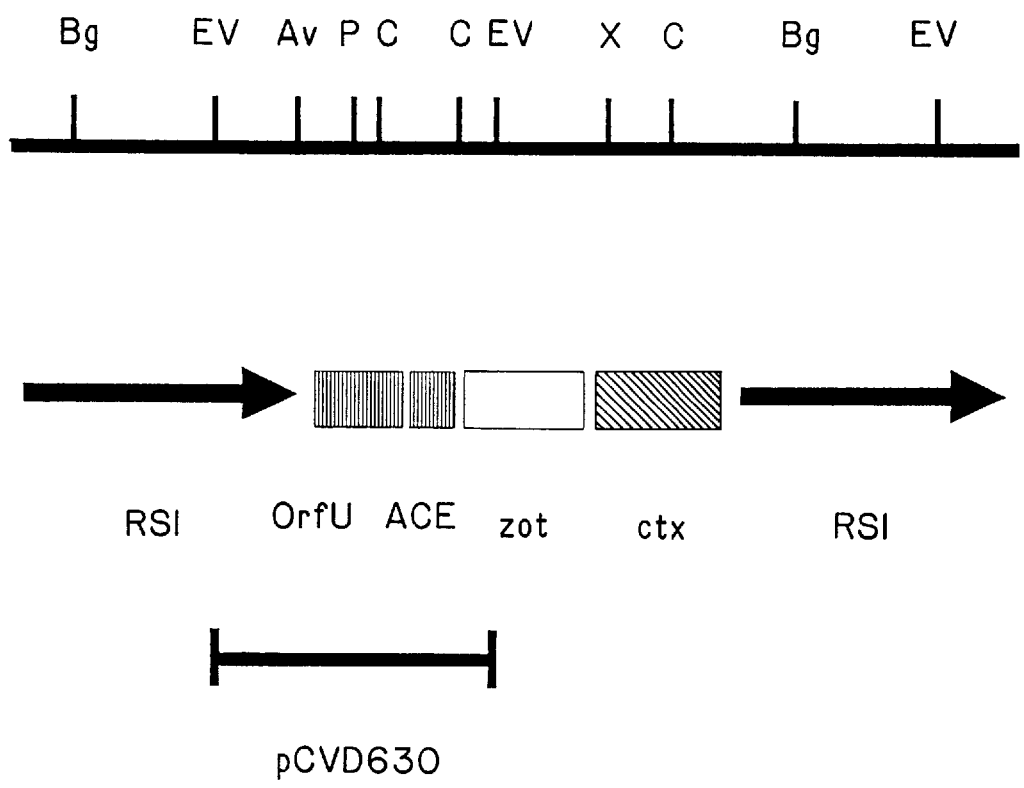

As previously described, (Example 10) the zot and ctx genes are on a 4.3 kb region of DNA which, in many El Tor strains, is flanked by copies of the RS1 sequence. For the vaccine strain CVD110, this entire region is deleted. In addition to the zot and ctx genes, there are DNA sequences encoding a third toxin, ACE. In FIG. 20, the map of this region is shown. A 2.9 kb EcoRV fragment (SEQ ID No.: 1) was cloned into the vector pCVD315 Galen et al. Advances in Research on Cholera and Related Diahrreas, Vol. 7, (Sack et al., Eds.) pp. 143–153 (1990) to produce the clone pCVD630 (shown in FIG. 20).

Figures 21A, 21B:
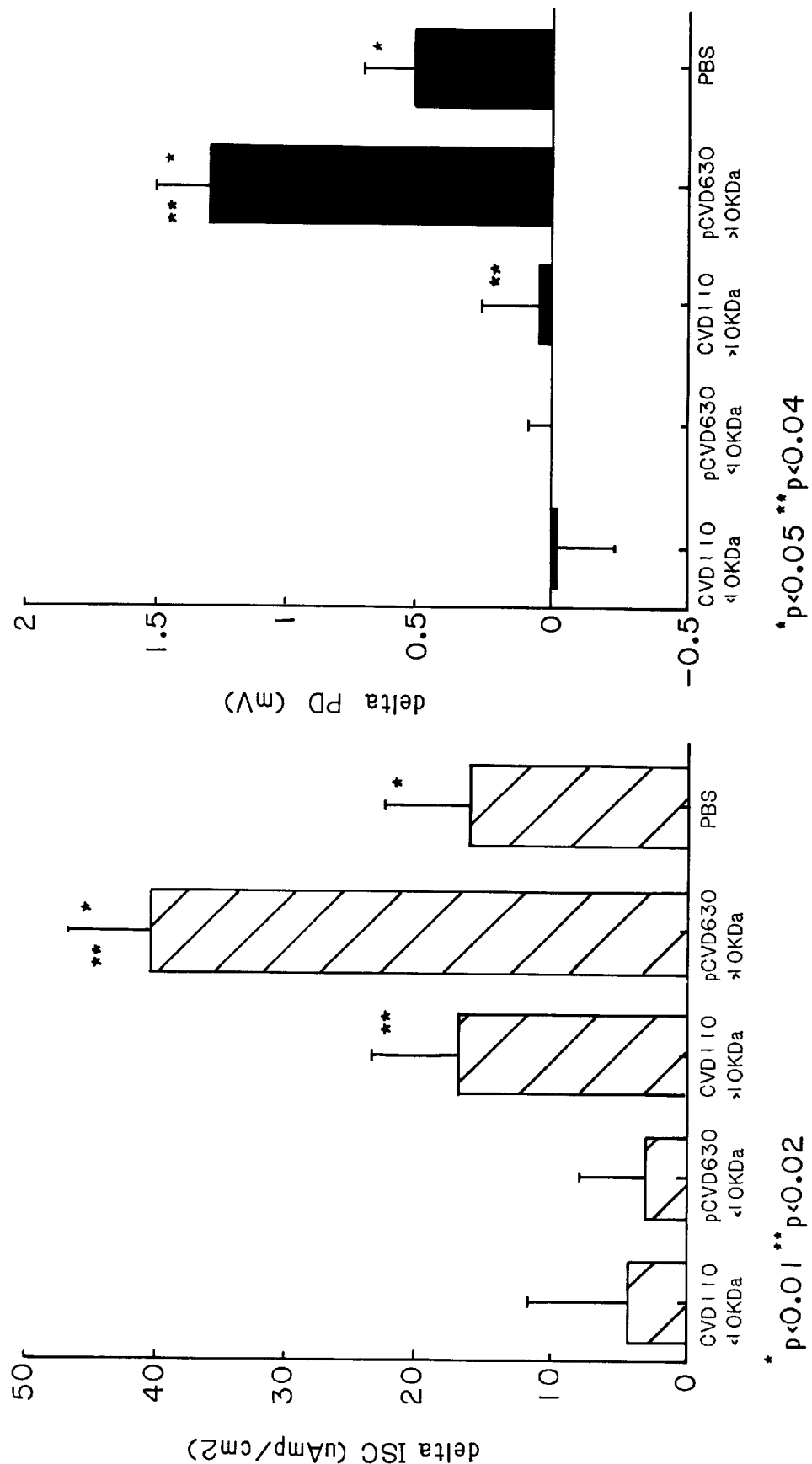

The plasmid pCVD630 was then introduced into *V. cholerae* strain CVD110 and the activity of this strain in Ussing chambers was studied (Ussing chambers as previously described. Culture supernatants of CVD110 and CVD110 containing pCVD630 were tested as previously described. FIG. 21A shows the results of supernatant fractions which contained molecules less than 10 kDa in size and fractions which contained molecules greater than 10 kDa. Essentially no Ussing chamber activity was seen in the <10 kDa fraction. In the >10 kDa fraction, CVD110 produced some changes in short circuit current (Isc) but no more than the negative control, PBS (phosphate buffered saline). However, supernatants of the CVD110 (pCVD630) gave a significant increase in Isc. This difference was statistically different ($p<0.02$) than the result seen with CVD110 alone. As previously described, an increase in Isc can be due to either an increase in potential difference (PD) or tissue conductivity (Gt). The increase in Isc induced by the genes contained on pCVD620 is due an increase in PD, as shown in FIG. 21B.

Thus, the 4.3 kb region flanked by the RS1 elements in El Tor strains contains 3 putative enterotoxins. (This same 4.3 kb region is present in classical strains but RS1 sequences are found on only one side.) All three of these toxins are capable of increasing Isc in Ussing chambers using rabbit ileal tissue, an activity which correlates with diarrheagenicity in humans. Two toxins, cholera toxin and ACE, act by increasing PD while the third, ZOT acts by increasing tissue conductivity. It is desirable that all three activities are eliminated from an attenuated *V. cholerae* vaccine strain to avoid the reactogenicity seen with CVD101 and other attenuated vaccine strains. CVD110 does lack all three activities and as seen in FIG. 21, produces changes in Ussing chamber comparable to changes induced by PBS (i.e. essentially no changes).

The DNA sequence of the 2.9 kb EcoRV fragment (SEQ ID No.: 1) contained in pCVD620 is shown in FIG. 22. There are two open reading frames (ORFs) immediately upstream of the zot gene. The smaller ORF immediately upstream of zot is a 297 bp ORF (ACE) which could potentially encode a protein of 11 kDa and the larger ORF immediately upstream of the 297 bp ORF is a 1185 bp ORF (OrfU) which could potentially encode a protein of 44 kDa. Ace activity is thought to be localized to the 297 bp open reading frame.

EXAMPLE 13

Construction of *V. cholerae* CVD112 —a *V. cholerae* vaccine strain of the O139 serogroup Strains of *V. cholerae* are classified into multiple O groups. Strains of O group 1 cause cholera gravis with the potential for widespread transmission in pandemics. *V. cholerae* of other O groups, so-called non-O1 *V. cholerae*, cause illness, but until recently, did not produce pandemic illness. Recently, tens of thousands of cases of illness due to non-O1 *V. cholerae* have been reported. It is thought that current O1-based vaccine strains may not prove effective in protection against the symptoms of non-O1 serogroups. The new non-O1 strain isolated was given the new serogroup designation O139.

Figure 23:
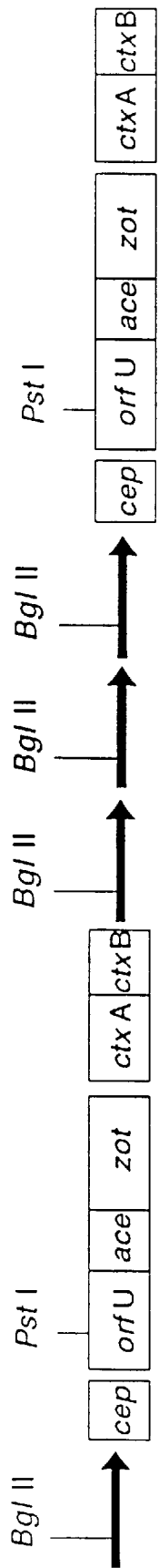

The starting strain for the production of a non-O1 *V. cholerae* vaccine strain is *V. cholerae* 1837. This strain is of the O139 serotype and was isolated from a patient with cholera in Bangladesh. FIG. 23 depicts the chromosomal arrangement of the cholera toxin locus in strain 1837.

Figure 24:
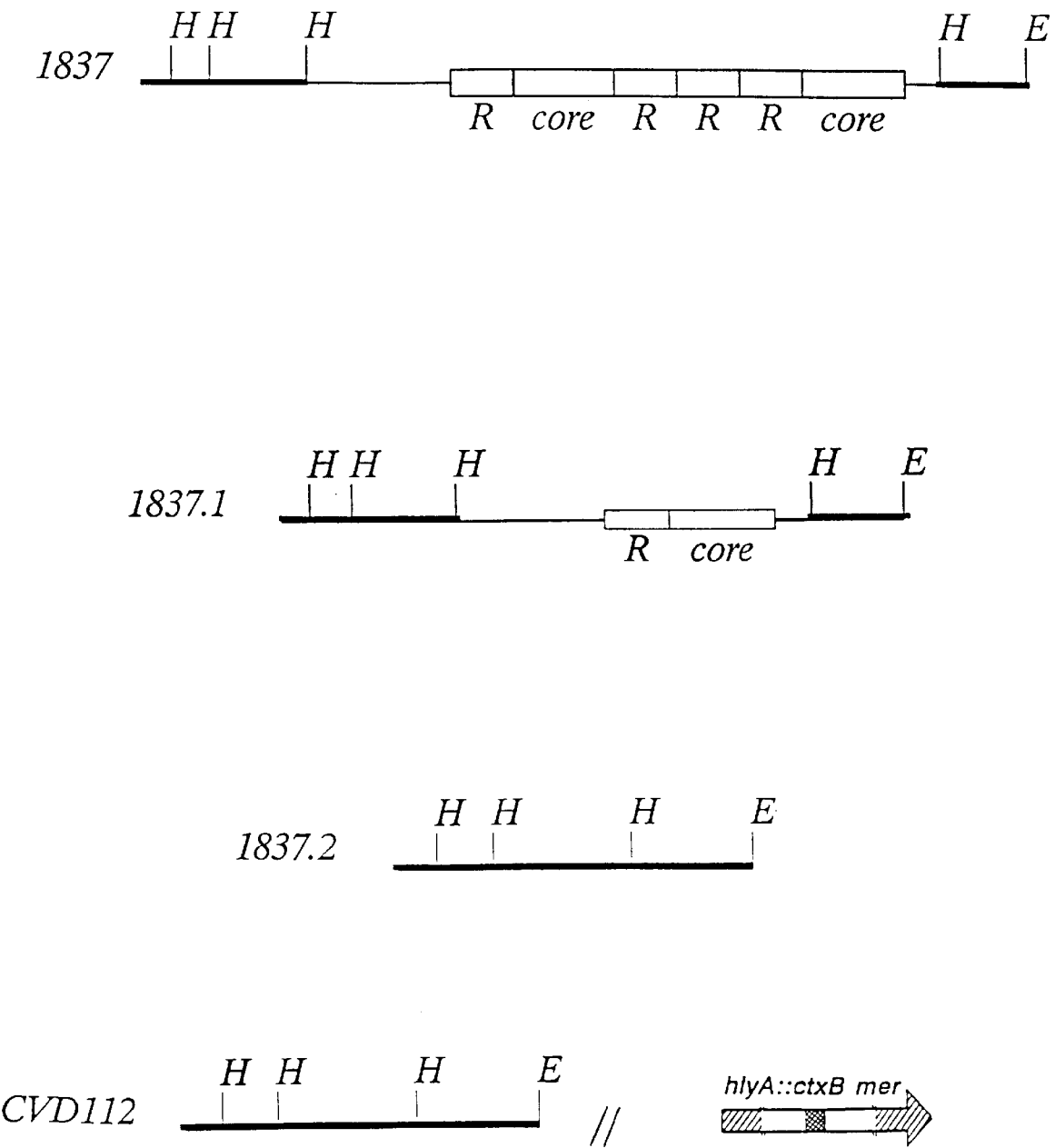

Plasmid pCVD51 was introduced into strain 1837 as described in Example 10. This plasmid recombined into the bacterial chromosome and a second recombination event resulted in the loss of one copy of the toxin genes and 3 copies of the RS1 elements. The resulting strain, *V. cholerae* 1837.1, is shown on the second line of FIG. 24 For simplicity, in FIG. 24 the cep, orfu, ace, zot, ctxAB sequences are together referred to as the *V. cholerae* toxin "core." The *V. cholerae* chromosomal locus comprises the one or more core regions and associated RS1 elements.

Figure 25:
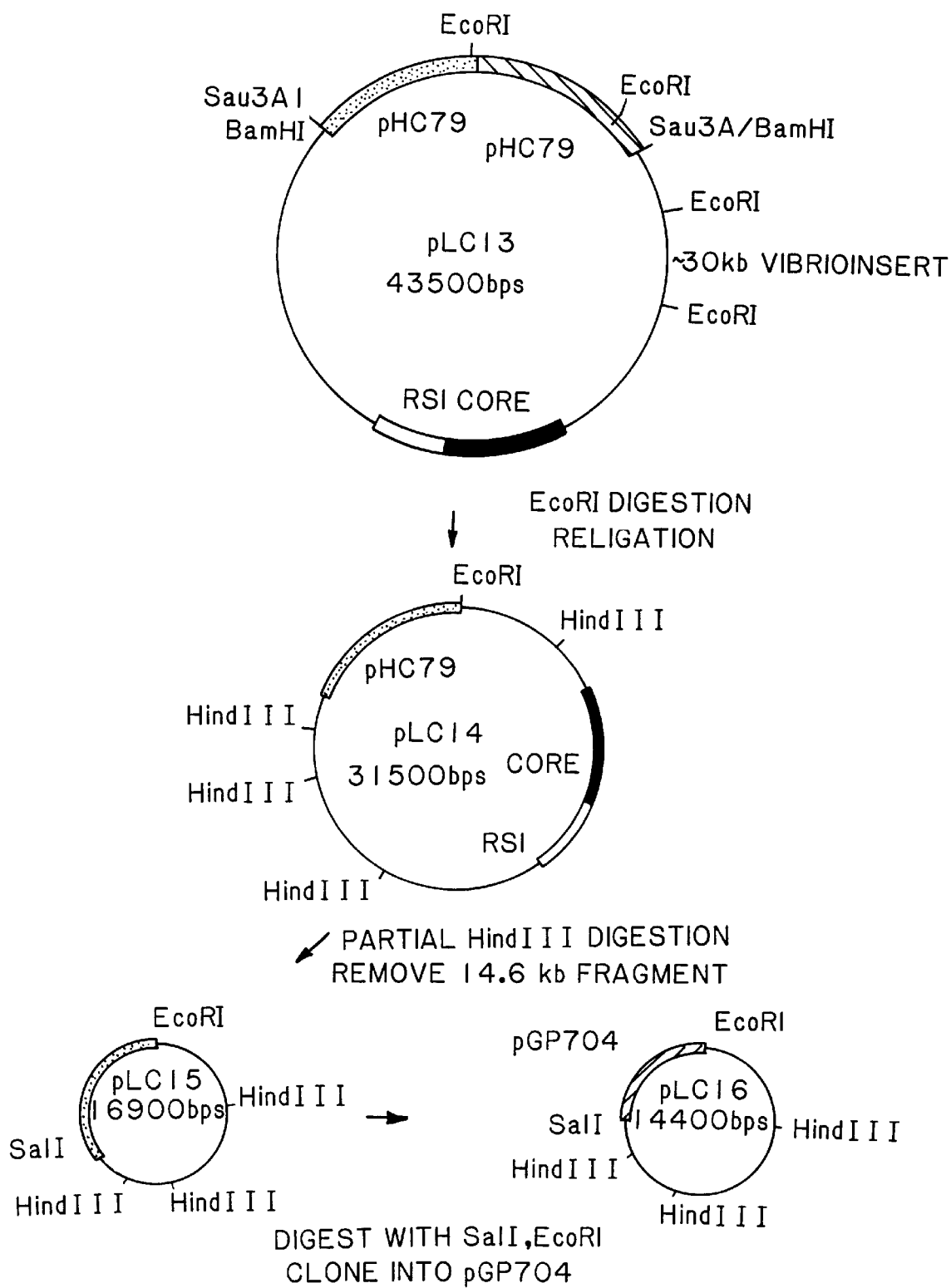

The remaining core sequences of strain 1837.1 were deleted as follows:

Chromosomal DNA from strain 1837.1 was prepared and partially digested with the restriction endonuclease Sau3a to yield fragments ca. 30 to 40 kb in size. These fragments were cloned into the cosmid cloning vector pHC79 (Hohn and Collins, *Gene,* 11, 291–298, 1980) and the resultant clones were screened after introduction into *E. coli* by DNA hybridization using ctx gene sequences as probe. A clone containing the cxt genes on a ca. 30 kb vibrio insert was identified and isolated and the resultant plasmid partially mapped. The isolated construct was designated pLC13 FIG. 25. This plasmid was digested with EcoRI and religated onto itself, thereby reducing the size of the insert to ca. 25 kb. The resulting plasmid was designated pLC14. pLC14 was partially digested with HindIII and then religated onto itself to remove an ca. 14.6 kb HindIII fragment containing the core region, the RS1 sequences and approximately 7.4 kb of uncharacterized *V. cholerae* DNA. The resulting plasmid, which lacks the core, RS1 sequences was designated pLC15. A similar HindIII fragment was removed in an attenuated strain construction described in Pearson et al., P. N. A. S. (USA), 90, 3750–3754, 1993. Plasmid pLC15 was then digested with SalI and EcoRI and the vibrio DNA was cloned into the suicide vector pGP704, described in Example 10. The resulting plasmid was designated pLC16.

The suicide vector pLC16 containing *V. cholerae* strain 1837.1 chromosomal sequences which flank the ctx locus was mobilized into *V. cholerae* strain 1837.1, by the method described in Example 10. Homologous recombination of the vector sequences into the chromosome was detected by screening for ampicillin resistant colonies, as ampicillin resistance is encoded by the vector sequences.

An ampicillin resistant *V. cholerae* produced by this method and having the plasmid sequences integrated into the bacterial chromosome was thereafter grown in the absence of ampicillin and the ampicillin sensitive colonies were selected. A second recombination event resulted in the loss of the ctxA, ctxB, zot, ace, orfu, cep and RS1 sequences along with the plasmid vector encoding ampicillin resistance. This resulting strain was designated 1837.2. The vibrio chromosome in strain 1837.2 is graphically depicted in the third line of FIG. 24.

The gene encoding the B subunit of cholera toxin along with a gene encoding mercury resistance was added to strain 1837.2 as described in Example 11 above. The same suicide vector, pCVD622.2B, was used as was employed to make strain CVD110. The event resulting in the incorporation of the B subunit sequences is depicted in FIG. 26. The final strain, CVD112, is deleted of all ctx, zot, ace, cep and RS1 sequences, expresses CTB subunit, and is mercury resistant.
Preparation of CVD112 and Al1837 for vaccine studies The *V. cholerae* CVD112 and Al1837 strains were stored in TSB containing 18% glycerol at −70° C. Before administration to volunteers, a vial of the appropriate strain was thawed and streaked onto blood agar, TCBS, and BI agar. After 24 hours incubation at 37° C., colonies that agglutinate the appropriate sera were chosen and plated onto BHI, and further incubated at 37° C. for about 20 hours. The *V. cholerae* was re-plated, followed by 5 hours incubation at 37° C. and harvested with sterile saline. The concentrations were determined by optical density of the solutions compared to that of known standards. Further quantitation was made by the replica plate technique before and after administration of the organism to volunteers.
Vaccine clinical trials Adult volunteers 18 to 40 years of age were recruited and informed, signed consent was obtained. Volunteers were carefully screened to ensure that they were in excellent physical and mental health.

A group of 14 volunteers were admitted to a medical isolation ward and acclimated to the environment for two days while medical screening was completed and baseline samples collected for antibody measurement.

Volunteers were randomized to receive one of the following, in double-blind manner, on the third day:

(i) CVD112 at $5 \times 10^8$ cfu with buffer (n=6)

(ii) CVD112 at $5 \times 10^6$ cfu buffer (n=6)

(iii) buffer alone

The two unvaccinated volunteers who received buffer only were kept with the vaccinees to determine whether person-to-person transmission of the vaccine strain occurred in this setting. Vaccinees were closely observed for 5 days after vaccination and then treated with a 5 day course of tetracycline.

The volunteers were challenged approximately four weeks later with the pathogenic *V. cholerae* O139 strain Al1837 to access vaccine efficacy against homologous challenge. The challenge dose comprised approximately $10^6$ cfu of *V. cholerae* O139 strain Al1837. Volunteers were closely monitored for about 120 hours following the challenge. All volunteers received tetracycline (500 mg every 6 hours for 5 days) beginning 5 days after vaccination and 4 days after challenge to eradicate carriage of the vaccine and challenge strains.

Eight vaccinees were challenged, four from the $5 \times 10^8$ group and four from the $5 \times 10^6$ group. Fifteen unvaccinated controls were also given a challenge dose. One of the eight vaccinees (13%) and twelve of the controls (80%) developed diarrhea after challenge, giving a vaccine efficacy of 84%. The one vaccinee who developed diarrhea had received the $5 \times 10^6$ dose of the CVD112 vaccine.

Three (38%) of the eight vaccinees and 14 (93%) of the controls shed the challenge strain, although the peak excretion was 100-fold less in the vaccinees, indicating that the vaccine strain had effectively colonized the vaccinees.

These results indicate that *V. cholerae* CVD112 is a safe and effective vaccine for protection against the symptoms of cholera for non-O1 vibrio strains of the O139 serotype.

EXAMPLE 14

Construction of *V. cholerae* CVD112 RM—An attenuated, recA⁻ *V. cholerae* derivative of the O139 serogroup.

*V. cholerae* strain CVD112 is the starting strain for the construction of a recA deficient, O139 serogroup, attenuated *V. cholerae* vaccine strain. Mutation of the recA gene is thought to be desirable to lower the already low probability that an attenuated strain would become virulent via recombination with wild-type ctx genes in vivo. The recA mutant was constructed in a manner similar to that described in Ketley et al., *Infect. and Immun.,* 58 (5), 1481–1484, 1980 and Goldberg et al., *J. Bacter.,* 165 (3), 715–722, 1986.

Plasmid pCVD831, which contains a ca. 7 kb NarI-NheI fragment having the recA gene of *V. cholerae* El Tor strain N16961 cloned into the broad host plasmid pCVD316, a derivative of the IncP plasmid pRK290 previously described above. pCVD831 was digested with XbaI and PvuII to remove a ca. 50 bp fragment internal to the recA gene coding sequences. The ends of the restricted DNA were made blunt and the plasmid was religated to itself. The ca. 50 bp deletion inactivates the recA protein. The resulting plasmid was designated pCVD832.

Figure 27:
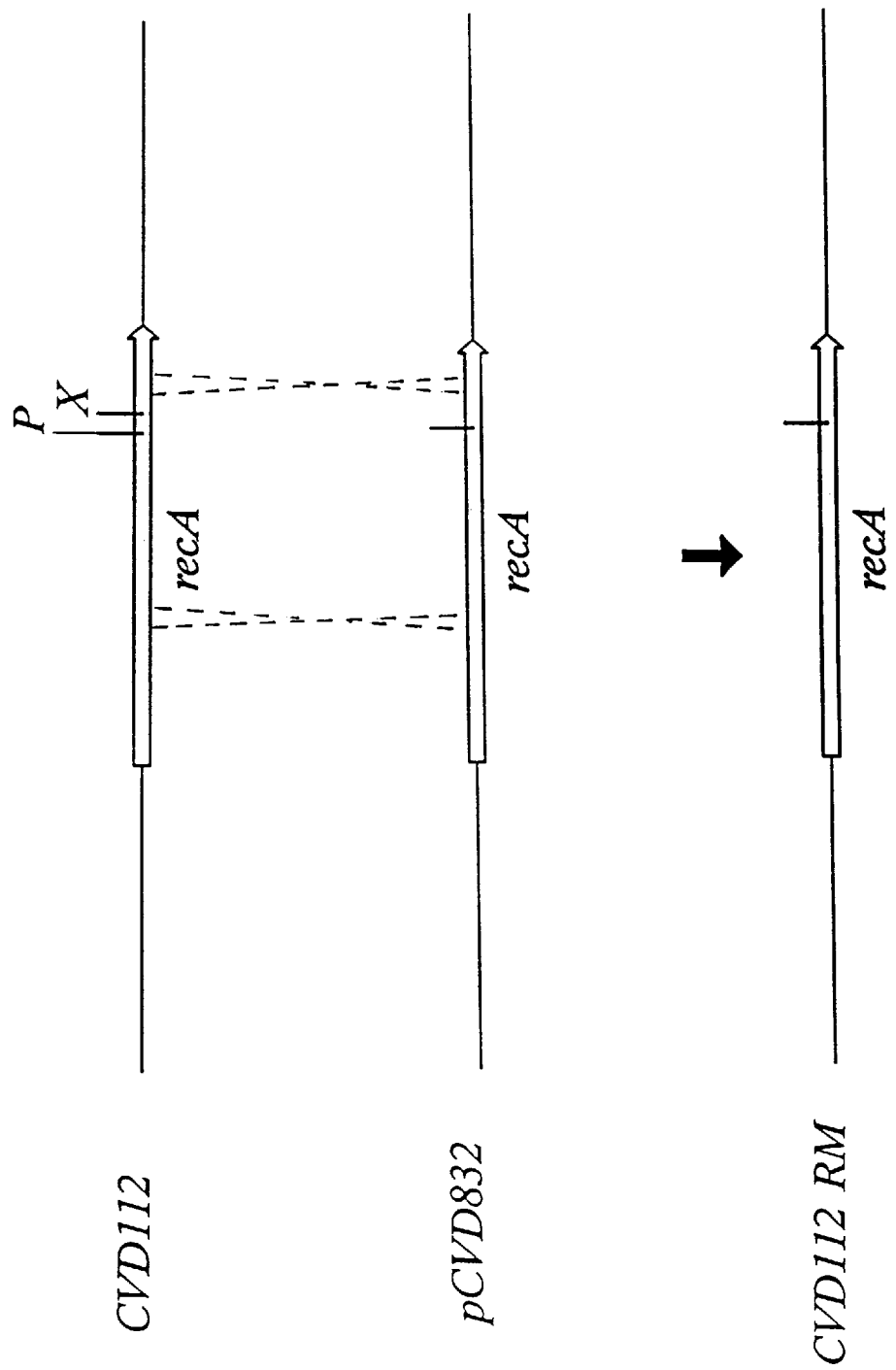
Figure 28A:
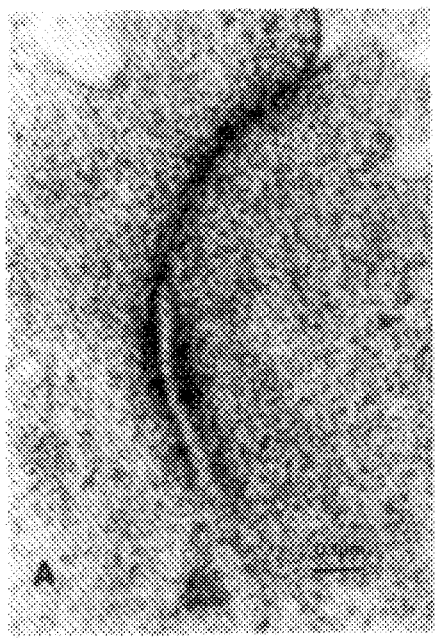
Figure 28B:
Figure 28C:
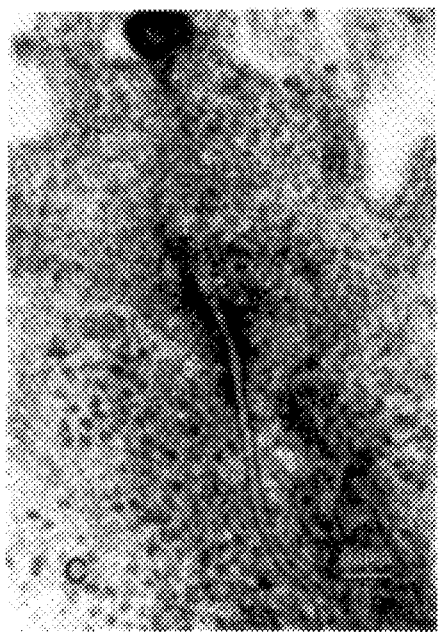
Figure 28D:
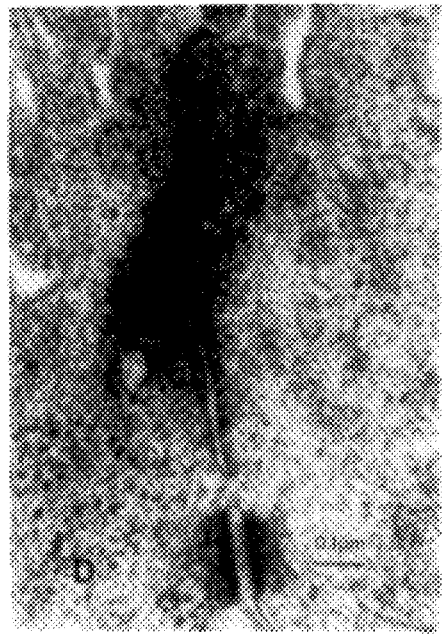
Figure 29A:
Figure 29B:
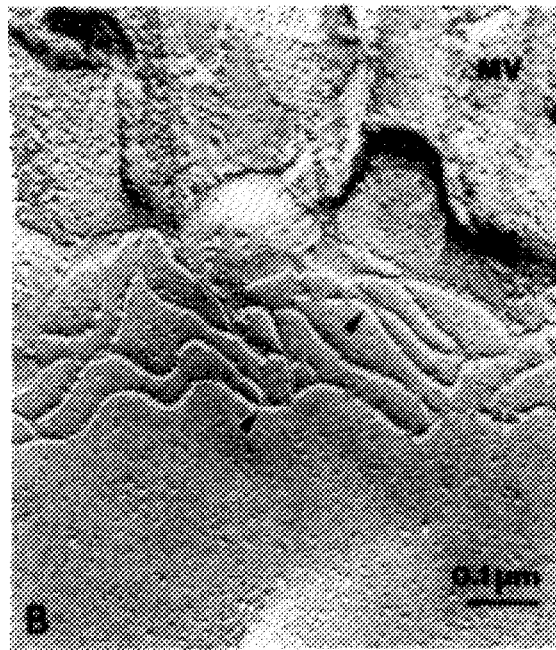

Plasmid pCVD832 is mobilized into *V. cholerae* CVD112 and homologous recombination replaces the native recA gene with the mutant recA gene. The homologous recombination event is detected by screening for sensitivity to methylmethanesulfonate (MMS), essentially as described by Kettler et al., (1980). supra. The strain resulting from the above procedure is deleted of all ctx, cep, orfu, ace, and RS1 sequences and has an inactivating mutation in the chromosomal recA locus (i.e., is a recA⁻ strain). The recombination event that occurs at the *V. cholerae* recA locus in the generation of strain CVD112 RM is graphically depicted in FIG. 27.

*V. cholerae* strains CVD112 and CVD112 RM are substantially efficient vaccine strains and afford substantial protection against virulent O139 serotype and other non-O1 strains upon subsequent challenge with these virulent strains.

CVD112 and CVD112RM may also be employed with one or more *V. cholerae* vaccine strains, toxoids, procholeragenoid, etc., in a combination vaccine for protection against both virulent O1 strains and virulent non-O1 strains, for example strains of the Ogawa or Inaba serotype, of *V. cholerae*.

Recently, it has been reported that the cep locus, which encodes the core encoded pilus, might act as an accessory colonization factor. However, the cep gene product is not thought to substantially interfere with the ability of *Vibrio cholerae* strains under the invention to colonize the intestines of a host organism, in particular, the human intestine. However, if desirable, the sequences comprising the cep, or any other suitable colonization factor, can be re-inserted into the chromosome of the *V. cholerae* of the invention following the guidance and methods described herein.

As example, in re-inserting DNA encoding the cholera toxin B subunit and a DNA encoding for resistance to mercury into the chromosome at the hemolysin locus, one can conveniently include the gene of interest, operably linked to expression signal, into the plasmid employed in the recombination procedure.

The resultant strain of such a recombination event produces the B subunit of cholera toxin, a protein conferring resistance to mercury and other heavy metals, and the additional gene of interest.

EXAMPLE 15

*V. cholerae* CVD111 vaccine strain

Another *V. cholerae* vaccine strain designated *V. cholerae* CVD111 (ctxA⁻, zot⁻, ace⁻, mer, ctxB) was constructed in the same manner as that described above for vaccine strains CVD109 and CVD110. However, the starting strain for this additional vaccine was instead *V. cholerae* El Tor Ogawa N16117. This strain produces cholera toxin, ZOT and ACE. However, despite producing cholera toxin, strain N16117 did not cause diarrhea when tested in volunteers. Strain N16117 was initially described in Levine et al. *Acute Enteric Infections in Children, New Prospects for Treatment and Prevention*, 1981, supra. It should be understood that the recA mutation described above in CVD112RM may also be generated in the CVD111 *V. cholerae* by the methods described if such is desired.

As *V. cholerae* CVD111 is derived from a strain which does not cause diarrhea, deletion of the ctxA, zot and ace genes provides a vaccine strain that has minimal reactogenicity but, by still expressing the cholera toxin B subunit, elicits substantial immunogenic response.

*V. cholerae* CVD111 is administered in dosage regimens as described above, to produce protection against the symptoms of cholera upon subsequent exposure to virulent *V. cholerae* strains.

While the invention has been described in connection with specific embodiments thereof, it will be understood that it is capable of further modification and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. An avirulent *Vibrio cholerae* strain of a non-O1 serogroup having the DNA comprising the cholera toxin core and the RS1 sequences of the cholera toxin locus deleted, and further having a DNA encoding a resistance to mercury, and a DNA encoding the cholera toxin B subunit re-inserted in the chromosome.

2. The avirulent *V. cholerae* according to claim 1, where said strain is of the O139 serogroup.

3. The avirulent *Vibrio cholerae* according to claim 2, wherein said DNA encoding a resistance to mercury, and a DNA encoding the cholera toxin B subunit are inserted at the chromosomal site of a hemolysin gene.

4. The avirulent *V. cholerae* according to claim 3, wherein said strain is *V. cholerae* CVD112 or a derivative thereof.

5. An avirulent *Vibrio cholerae* strain of a non-O1 serogroup having the DNA comprising the cholera toxin core and the RS1 sequences of the cholera toxin locus deleted, a deletion of the recA gene, and further having a DNA encoding a resistance to mercury, and a DNA encoding the cholera toxin B subunit re-inserted in the chromosome.

6. The avirulent *V. cholerae* according to claim 5, where said strain is of the O139 serogroup.

7. The avirulent *Vibrio cholerae* according to claim 6, wherein said DNA encoding a resistance to mercury, and a DNA encoding the cholera toxin B subunit, or a part thereof, are inserted at the chromosomal site of a hemolysin gene.

8. The avirulent *Vibrio cholerae* according to claim 6, wherein said deletion in the recA gene is a deletion in the recA coding sequences.

9. The avirulent *V. cholerae* according to claim 8, wherein said strain is *V. cholerae* CVD112 RM or a derivative thereof.

10. A method of making an avirulent *V. cholerae* non-O1, having a deletion of the cholera toxin core and RS1 sequences but expressing sequences of the cholera toxin B subunit, or a part thereof sufficient to confer immunogenicity, and sequences encoding a product which confers resistance to heavy metals, comprising the steps of:

(a) providing a first plasmid comprising DNA of the *Vibrio cholerae* cholera toxin core region and flanking sequences of sufficient length to promote detectable in vivo recombination, ligated to a gene encoding a first selectable marker of foreign origin which confers resistance to a selective agent, wherein said first plasmid is incapable of replicating extrachromosomally in *V. cholerae;*

(b) mating a virulent strain of *Vibrio cholerae* of a non-O1 serogroup with a first microorganism carrying the first plasmid;

(c) selecting for and isolating *Vibrio cholerae* expressing the first selectable marker;

(d) growing the *V. cholerae* isolated in step (c) in the absence of said selective agent;

(e) screening the *V. cholerae* of step (d) for the loss of expression of said first selectable marker;

(f) providing a second plasmid comprising *Vibrio cholerae* non-O1 chromosomal sequences which flank the cholera toxin locus, deleted of DNA of the cholera toxin core and RS1 sequences, ligated to a second selectable marker of foreign origin which confers resistance to a second selective agent;

(g) mating the screened product of step (e) with a second microorganism carrying said second plasmid; and (h) selecting for *Vibrio cholerae* which express the second selectable marker;

(i) growing the selected product of step (h) in the absence of the second selective agent;

(j) screening the *V. cholerae* of step (i) for the loss of said second selectable marker;

(k) isolating the screened product of step (j);

(l) providing a third plasmid comprising *V. cholerae* chromosomal sequences of sufficient length to promote detectable in vivo recombination flanking sequences of the cholera toxin B subunit sufficient to confer immunogenicity, and sequences encoding a product which confers resistance to heavy metals, and ligated to a third selectable marker of foreign origin, wherein said third plasmid is incapable of replicating extrachromosomally in *V. cholerae;*

(m) mating the screened product of step (j) with a third microorganism carrying said third plasmid;

(n) selecting for *Vibrio cholerae* which express the third selectable marker; and (o) isolating the selected product of step (n).

11. The method of making an avirulent *V. cholerae* non-O1 according to claim 10, wherein said virulent strain of *Vibrio cholerae* non-O1 is of the O139 serogroup.

12. The method of making an avirulent *V. cholerae* non-O1 according to claim 11, wherein said virulent strain of *V. cholerae non-O1* is strain 1837.

13. The method of making an avirulent *V. cholerae* non-O1 according to claim 12, wherein said isolated selected product of step (o) is *V. cholerae* CVD112.

14. A method of making an avirulent, recombination-deficient *V. cholerae* non-O1 having a deletion of the cholera toxin core and RS1 sequences but expressing sequences of the cholera toxin B subunit, or a part thereof sufficient to confer immunogenicity, and sequence which encodes a product which confers resistance to heavy metals comprising the steps of:

(a) providing a first plasmid comprising DNA of the *Vibrio cholerae* cholera toxin core region and flanking sequences of sufficient length to promote detectable in vivo recombination, ligated to a gene encoding a first selectable marker of foreign origin which confers resistance to a selective agent, wherein said first plasmid is incapable of replicating extrachromosomally in *V. cholerae;*

(b) mating a virulent strain of *Vibrio cholerae* of a non-O1 serogroup with a first microorganism carrying the first plasmid;

(c) selecting for and isolating *Vibrio cholerae* expressing the first selectable marker;

(d) growing the *V. cholerae* isolated in step (c) in the absence of said selective agent;

(e) screening the *V. cholerae* of step (d) for the loss of expression of said first selectable marker;

(f) providing a second plasmid comprising *Vibrio cholerae* non-O1 chromosomal sequences which flank the cholera toxin locus, deleted of DNA of the cholera toxin core and RS1 sequences, ligated to a second selectable marker of foreign origin which confers resistance to a second selective agent;

(g) mating the screened product of step (e) with a second microorganism carrying said second plasmid; and (h) selecting for *Vibrio cholerae* which express the second selectable marker;

(i) growing the selected product of step (h) in the absence of the second selective agent;

(j) screening the *V. cholerae* of step (i) for the loss of said second selectable marker;

(k) isolating the screened product of step (j);

(l) providing a third plasmid comprising *V. cholerae* chromosomal sequences of sufficient length to promote detectable in vivo recombination flanking sequences of the cholera toxin B subunit sufficient to confer immunogenicity, and sequences encoding a product which confers resistance to heavy metals, and ligated to a third selectable marker of foreign origin, wherein said third plasmid is incapable of replicating extrachromosomally in *V. cholerae;*

(m) mating the screened product of step (j) with a third microorganism carrying said third plasmid;

(n) selecting for *Vibrio cholerae* which express the third selectable marker;

(o) isolating the selected product of step (n);

(p) providing a fourth plasmid comprising flanking sequences sufficient in length to promote detectable recombination at the *V. cholerae* recA locus, flanking recA gene sequences deleted to inactivate the recA gene product, ligated to a fourth selectable marker, wherein said fourth plasmid is incapable of replicating extrachromosomally in *V. cholerae;*

(q) mating the isolated product of step (p) with a fourth microorganism carrying said fourth plasmid;

(r) selecting for *Vibrio cholerae* which express the fourth selectable marker; and (s) isolating the selected product of step (r).

15. The method of making an avirulent *V. cholerae* non-O1 according to claim 14, wherein said virulent strain of *Vibrio cholerae* non-O1 is of the 0139 serogroup.

16. The method of making an avirulent *V. cholerae* non-O1 according to claim 15, wherein said virulent strain of *V. cholerae* non-O1 is strain 1837.

17. The method of making an avirulent *V. cholerae* non-O1 according to claim 16, wherein said isolated selected product of step (s) is *V. cholerae* CVD112 RM.

18. A vaccine for the protection against cholerae upon exposure to *V. cholerae* non-O1 comprising the avirulent *V. cholerae* non-O1 according to claim 1.

19. A vaccine for the protection against cholerae upon exposure to *V. cholerae* non-O1 comprising the avirulent *V. cholerae* non-O1 according to claim 5.

20. An avirulent *V. cholerae* of the O1 serotype having a genotype comprising ctxA$^-$, zot$^-$, mer, and ctxB, wherein the DNA comprising the cholera toxin core and the RS1 sequences of the cholera toxin locus are deleted, and a DNA encoding a resistance to mercury and a DNA molecule encoding the cholera toxin B subunit are inserted in the chromosome.

21. The avirulent *V. cholerae* according to claim 20, wherein said *V. cholerae* is of the Ogawa serotype.

22. The avirulent *V. cholerae* according to claim 21, wherein said *V. cholerae* is derived from strain N16117.

23. An avirulent *V. cholerae* having substantially all of the identifying characteristics of *V. cholerae* CVD111.

24. *V. cholerae* CVD111.

25. A culture comprising *V. cholerae* CVD111.

26. A vaccine for protecting against cholera comprising *V. cholerae* CVD111 in a pharmaceutically acceptable carrier.

27. The vaccine for protecting against cholera according to claim 26, wherein said vaccine is a live vaccine.

28. A method for protecting humans against cholera comprising:

obtaining a culture comprising *V. cholerae* CVD111 and administering an effective amount of said culture to a human.

29. The method for protecting humans against cholera according to claim 28, wherein said culture is administered orally.

* * * * *

UNITED STATES PATENT AND TRADEMARK OFFICE
CERTIFICATE OF CORRECTION

PATENT NO. : 5,882,653
DATED : March 16, 1999
INVENTOR(S) : James B. Kaper, et al.

It is certified that error appears in the above-identified patent and that said Letters Patent is hereby corrected as shown below:

Column 14, line 6, change "FIG. 22A-f)" to --FIG. 22(A-F)--.

Column 32, line 23, change "FIG. 22" to --FIG. 22(A-F)--.

Column 62, line 6, change "(p)" to --(0)--.

Signed and Sealed this

Twenty-fifth Day of May, 1999

*Attest:*

Q. TODD DICKINSON

*Attesting Officer*   Acting Commissioner of Patents and Trademarks

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 2912 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Vibrio cholerae
        ( B ) STRAIN: classical 395

( v i i ) IMMEDIATE SOURCE:
        ( B ) CLONE: ace/orfU ( x i ) SEQUENCE DESCRIPTION: SEQ ID NO:1:

| | | | | | | |
|---|---|---|---|---|---|---|
| GATATCCACT | CACGCATTAA | GTGGGCTCGT | CGTCAGGTCG | GTAAGACGTT | GTTTGATATT | 60 |
| TCAAAGCATT | TTGGTGGTGA | TTTGGAAAGG | GTGTTTGGGG | CGTTGATTTC | TAAGGAAATT | 120 |
| CACGACGATT | CACTCAACCT | TCCAGATTCT | TATATGAAGT | TAATTGATGA | AATTATGGGT | 180 |
| GATTAATATG | AAATCTCGTT | TTGTTGTTTT | TGGTGCCTCT | CATTCTGAAG | GGGTGAGTAA | 240 |
| GACTGGTGCT | CCTTACCTTA | TCCCAGTGCT | TTTTGTTGGT | AAGCCGATTC | GCCAGTGGAA | 300 |
| AAACGATAAA | GGCCAATGTT | TGACGTTTGG | CTTGCAGCAT | CAGGAAGTGA | AATTTGTATC | 360 |
| CAGTGACGCG | ATGACCAGAA | AACTCGAACA | GACCGCCTTT | CCGGTTCTTG | TCACGTTTGA | 420 |
| CAATGAGCCA | GACCCAGAAG | ACCCATCGCG | TAACCTCGTG | ATTGATTATC | AAGTGGTGTG | 480 |
| TTCCTTGTTT | GACAACGTGC | CGGGCGCAAG | CCATTGGATA | AACCTCAACC | CATTAAATCT | 540 |
| TGATGGACTT | AACCCATTAT | GTCTGGAGCG | AGGCGCTCTA | TTTCGCGGTG | GTCAAGGCCG | 600 |
| TTCTCGTTCT | GTTCTTTACA | TCCTTTGGGA | TTGGCGCGGT | TGCCAGTCTC | ATTTTATCCA | 660 |
| CGGTAAAGGA | GAAGCTACAT | GTTAGCTCA | CTGAAAAACA | AACTTAATAC | CTTTAAAAGC | 720 |
| ACCCTTTCAC | TCGGGGTTTT | CTTGCTGTTT | TCCGCATTTG | CTAACCAAGC | ACTCGCGGCT | 780 |
| GCTGATACGG | GTTTGGTCGC | GGAAGTCACC | AAAACACTGG | GCACCAGTAA | AGATACGGTG | 840 |
| ATTGCGCTTG | GGCCGCTTAT | CATGGGCGTG | GTGGGAGCAA | TTGTTCTGAT | TGTTACCGTG | 900 |
| ATTGGCTTAA | TTCGTAAGGC | TAAATAGTGC | TTGAGTTGTG | GCTGGGTCTC | TTTGGCTCAG | 960 |
| CGGTCATCAT | TATCGGCTTT | GTGTCGGGCT | TATATTTGGT | TTAAGGAGG | AGGGCGAGCG | 1020 |
| TTCGCCCTTT | TTTATGCGCT | ATTTTCTACT | GTTTTGACA | TTGCTCTTTC | TTTCTCCATC | 1080 |
| GGTAACAGCT | TCCTCCATCA | ATTGTGATCC | TAATACTACT | ACGTCACACC | AGTTACTTTT | 1140 |
| CGGTTTTGGC | TCTCCCATTG | TGCAATCGGT | GTTATTTGAT | GGCTGCATGC | TTGATATTGA | 1200 |
| AAAAGATGAC | TATGGTTTTG | TTTGGTCTTG | TCTCTCAAAT | GAAAATGGGG | ACTATTGCAA | 1260 |
| GGGGCTCTAC | AAACCCCGTT | TTACACAAGG | GGTGTCCCCG | AACTGGCCGA | TGTGCGACTT | 1320 |
| GTCCGGAGCA | TCTGCAGAGC | GCTGCATTTA | TCCTTATTGC | CCTGAGGGGG | AAGAGTGCGT | 1380 |
| TCCCTTACCA | CCTTCACCGC | CCAGTGATTC | CCCTGTTGAT | GGGCTGAGCA | GCTCGTTTAA | 1440 |
| GTCTGCGTTC | AATCAGGTCT | ATAAAAACCA | ATCAGAGATG | GCTTCGACTC | TCAATCATGT | 1500 |
| CAGTGGTCAG | GTGTCCCACT | CTCAAGATAT | GGTTCAGCTC | AATACGAAGT | TCACGCGGA | 1560 |
| CCGTGTTCTT | GAAAAAGTGA | ACGCAATCAA | CAATCGATTG | AATGGGCAGA | TAAACTATCT | 1620 |
| TGAAGAAGTT | CGCATCGATG | TATGGGATAC | ACAACGGGAG | GTCAGAAAAG | CCAAGGATGA | 1680 |
| ACTCTCTTCA | CGTGTTGGTT | CTGTTGCACA | CGATGTTTAC | CAAAGTAAGA | ATGCTGTGCT | 1740 |
| TCGGGCGATT | GATGAGCTTA | AAGATTCACT | CGGTGGGGTT | GTCGTTCCGC | CTAACCCAGA | 1800 |
| CCAACCCAAT | CCCACGCCAC | CCGATAGCAG | CAGCCCCAAT | TATACAGGGG | CGCTTAATAC | 1860 |
| CATCTCTAAA | AAGCTCAATA | CCTTAGAGAC | GATTTCACAG | CAACTCGACA | CCATGAACAC | 1920 |
| GGCGCTATCA | GGGCGCTGTA | GTAACCCTGC | TCGCTGTCAG | TTTCCGATAC | GCGAGGCCGA | 1980 |
| GACCGAGTTA | GAAACGGCTC | AGCAGAATTT | AAAGCAGATG | ATCAACGATA | AATCACCCA | 2040 |
| GTCGGCTTTG | CATCAGTTCA | AAGGCTCGGC | GGCGGTGCCT | TCGTTTGCT | CCTATGTCGA | 2100 |
| GGAGTTTGGT | TACAACCTCT | GTTTTGACTT | CTCCCTCTTT | TCTGAAAACC | TGCACATCAT | 2160 |
| CCGCATGATA | GTGCTCGCGA | TGGCGTACAT | TCTGGCCGCC | ATGCTCATTT | TGTTTAGGTG | 2220 |
| ATGCTTATGA | TGGACCCCCT | TTATGACTGG | CTAATTGATG | GCTTACGTG | GCTTGTGATC | 2280 |
| AAGCTCGGTA | TTATGTGGAT | TGAGAGCAAG | ATTTTTGTCA | TCCAATTCTT | CTGGGAGATG | 2340 |

| TCCCAGAAAG | TGATTGATAT | GTTTACCATC | TATCCGCTTA | TCCAACAGGC | TATCGATATG | 2400 |
| CTGTCTCCTC | AATACAGCGG | CTTTCTGTTC | TTTTTAGGGT | TAGACCAAGC | GCTGGCTATC | 2460 |
| GTGCTTCAGG | CTTTGATGAC | CCGTTTCGCC | CTGCGAGCGT | TAAACCTATG | AGTATCTTTA | 2520 |
| TTCATCACGG | CGCGCCAGGC | TCTTATAAAA | CGTCCGGGGC | ATTATGGCTT | CGTCTGCTGC | 2580 |
| CGGCGATTAA | GTCAGGCCGT | CACATCATCA | CGAATGTGCG | AGGCTTAAAC | CTTGAACGCA | 2640 |
| TAGCTAAGTA | CTTAAAAATG | GACGTCTCAG | ACATCAGTAT | CGAGTTTATT | GATACAGACC | 2700 |
| ATCCAGACGG | TCGCTTAACG | ATGGCGCGTT | TTTGGCACTG | GGCGAGAAAG | GACGCGTTTC | 2760 |
| TCTTTATTGA | TGAATGTGGT | CGCATCTGGC | CGCCGAGACT | GACGGCCACC | AATTTAAAGG | 2820 |
| CGCTCGACAC | GCCGCCGGAT | TTGGTCGCAG | AGGATAGGCC | TGAGAGCTTT | GAGGTGGCTT | 2880 |
| TTGACATGCA | TCGTCACCAC | GGCTGGGATA | TC | | | 2912 |

(2) INFORMATION FOR SEQ ID NO:2:

(i) SEQUENCE CHARACTERISTICS:
    (A) LENGTH: 291 base pairs
    (B) TYPE: nucleic acid
    (C) STRANDEDNESS: double
    (D) TOPOLOGY: linear (ii) MOLECULE TYPE: DNA (genomic)

(iii) HYPOTHETICAL: NO (iv) ANTI-SENSE: NO (v) ORIGINAL SOURCE:
    (A) ORGANISM: Vibrio cholerae
    (B) STRAIN: classical 395

(vii) IMMEDIATE SOURCE:
    (B) CLONE: ace (xi) SEQUENCE DESCRIPTION: SEQ ID NO:2:

| ATGCTTATGA | TGGACCCCCT | TTATGACTGG | CTAATTGATG | GCTTTACGTG | GCTTGTGATC | 60 |
| AAGCTCGGTA | TTATGTGGAT | TGAGAGCAAG | ATTTTTGTCA | TCCAATTCTT | CTGGGAGATG | 120 |
| TCCCAGAAAG | TGATTGATAT | GTTTACCATC | TATCCGCTTA | TCCAACAGGC | TATCGATATG | 180 |
| CTGTCTCCTC | AATACAGCGG | CTTTCTGTTC | TTTTTAGGGT | TAGACCAAGC | GCTGGCTATC | 240 |
| GTGCTTCAGG | CTTTGATGAC | CCGTTTCGCC | CTGCGAGCGT | TAAACCTATG | A | 291 |

(2) INFORMATION FOR SEQ ID NO:3:

(i) SEQUENCE CHARACTERISTICS:
    (A) LENGTH: 1188 base pairs
    (B) TYPE: nucleic acid
    (C) STRANDEDNESS: double
    (D) TOPOLOGY: linear (ii) MOLECULE TYPE: DNA (genomic)

(iii) HYPOTHETICAL: NO (iv) ANTI-SENSE: NO (v) ORIGINAL SOURCE:
    (A) ORGANISM: Vibrio cholerae
    (B) STRAIN: classical 395

(vii) IMMEDIATE SOURCE:
    (B) CLONE: orfU (xi) SEQUENCE DESCRIPTION: SEQ ID NO:3:

| ATGCGCTATT | TTCTACTGTT | TTTGACATTG | CTCTTTCTTT | CTCCATCGGT | AACAGCTTCC | 60 |

```
TCCATCAATT  GTGATCCTAA  TACTACTACG  TCACACCAGT  TACTTTTCGG  TTTTGGCTCT    120

CCCATTGTGC  AATCGGTGTT  ATTTGATGGC  TGCATGCTTG  ATATTGAAAA  AGATGACTAT    180

GGTTTTGTTT  GGTCTTGTCT  CTCAAATGAA  AATGGGGACT  ATTGCAAGGG  GCTCTACAAA    240

CCCCGTTTTA  CACAAGGGGT  GTCCCCGAAC  TGGCCGATGT  GCGACTTGTC  CGGAGCATCT    300

GCAGAGCGCT  GCATTTATCC  TTATTGCCCT  GAGGGGAAG   AGTGCGTTCC  CTTACCACCT    360

TCACCGCCCA  GTGATTCCCC  TGTTGATGGG  CTGAGCAGCT  CGTTTAAGTC  TGCGTTCAAT    420

CAGGTCTATA  AAAACCAATC  AGAGATGGCT  TCGACTCTCA  ATCATGTCAG  TGGTCAGGTG    480

TCCCACTCTC  AAGATATGGT  TCAGCTCAAT  ACGAAGTTTC  ACGCGGACCG  TGTTCTTGAA    540

AAAGTGAACG  CAATCAACAA  TCGATTGAAT  GGGCAGATAA  ACTATCTTGA  AGAAGTTCGC    600

ATCGATGTAT  GGGATACACA  ACGGGAGGTC  AGAAAAGCCA  AGGATGAACT  CTCTTCACGT    660

GTTGGTTCTG  TTGCACACGA  TGTTTACCAA  AGTAAGAATG  CTGTGCTTCG  GGCGATTGAT    720

GAGCTTAAAG  ATTCACTCGG  TGGGGTTGTC  GTTCCGCCTA  ACCCAGACCA  ACCCAATCCC    780

ACGCCACCCG  ATAGCAGCAG  CCCCAATTAT  ACAGGGGCGC  TTAATACCAT  CTCTAAAAAG    840

CTCAATACCT  TAGAGACGAT  TTCACAGCAA  CTCGACACCA  TGAACACGGC  GCTATCAGGG    900

CGCTGTAGTA  ACCCTGCTCG  CTGTCAGTTT  CCGATACGCG  AGGCCGAGAC  CGAGTTAGAA    960

ACGGCTCAGC  AGAATTTAAA  GCAGATGATC  AACGATAAAA  TCACCCAGTC  GGCTTTGCAT   1020

CAGTTCAAAG  GCTCGGCGGC  GGTGCCTTCG  TTTTGCTCCT  ATGTCGAGGA  GTTTGGTTAC   1080

AACCTCTGTT  TTGACTTCTC  CCTCTTTTCT  GAAAACCTGC  ACATCATCCG  CATGATAGTG   1140

CTCGCGATGG  CGTACATTCT  GGCCGCCATG  CTCATTTTGT  TTAGGTGA                 1188
```

( 2 ) INFORMATION FOR SEQ ID NO:4:

( i ) SEQUENCE CHARACTERISTICS:
        ( A ) LENGTH: 2915 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Vibrio cholerae
        ( B ) STRAIN: El Tor E7946

( v i i ) IMMEDIATE SOURCE:
        ( B ) CLONE: ace/orfU ( x i ) SEQUENCE DESCRIPTION: SEQ ID NO:4:

```
GATAACCACT  CACGCATTAA  GTGGGCTCGT  CGTCAGGTCG  GTAAGACGTT  GTTTGATATT     60

TCAAAGCATT  TTGGTGGTGA  TTTGGAAAGG  GTGTTTGGGG  CGTTGATTTC  TAAGGAAATT    120

CACGACGATT  CACTCAACCT  TCCAGATTCT  TATATGAAGT  TAATTGATGA  AATTATGGGT    180

GATTAATATG  AAATCTCGTT  TTGTTGTTTT  TGGTGCCTCT  CATTCTGAAG  GGGTGAGTAG    240

TAAGACTGGT  GCACCTTATC  TTATCCCAGT  GCTTTTTGTT  GGTAAGCCGA  TTCGCCAGTG    300

GAAAAACGAT  AAAGGCCAAT  GTTTGACGTT  TGGCTTGCAG  CATCAGGAAG  TGAAATTTGT    360

ATCCAGTGAC  GCGATGACCA  GAAAACTCGA  ACAGACCGCC  TTTCCGGTTC  TTGTCACGTT    420

TGACAATGAG  CCAGACCCAG  AAGACCCATC  ACGCAACCTC  GTGATTGATT  ATCAAGTGGT    480

GTGTTCCTTG  TTTGACAACG  TGCCGGGCGC  AAGCCATTGG  ATAAACCTCA  ACCCATTAAA    540
```

```
TCTTGATGGA  CTTAACCCAT  TATGTCTGGA  ACGAGGCGCT  CTATTTCGCG  GTGGTCAAGG      600
CCGTTCTCGT  TCTGTTCTTT  ACATCCTTTG  GGATTGGCGC  GGTTGCTAGT  CTCATTTTAT      660
CCACGGTAAA  GGAGAAGCTA  CATGTTTAGC  TCACTGAAAA  ACAAACTTAA  TACCTTTAAA      720
AGCACGCTTT  CACTCGGGGT  TTTCTTGCTG  TTTTCCGCAT  TTGCTAACCA  AGCACTCGCG      780
GCTGCTGATG  CGGGTTTGGT  CACGGAAGTC  ACCAAAACAC  TGGGCACCAG  TAAAGATACG      840
GTGATTGCGC  TTGGGCCGCT  CATCATGGGC  GTGGTGGGGG  CAATTGTTCT  GATTGTTACC      900
GTGATTGGCT  TAATTCGTAA  GGCTAAATAG  TGCTTGAGTT  GTGGCTGGGT  CTCTTTGGCT      960
CAGCGGTCAT  CATTATCGGC  TTTGTGTCGG  GCTTATATTT  GGTTTAAGGG  AGGAGGGCGA     1020
GCGTTCGCCC  TTTTTTATGC  GCTATTTCT   ACTGTTTTTG  ACATTGCTCT  TTCTTTCTCC     1080
ATCGGTAACG  GCTTCCGCCA  TCAATTGTGA  TCCTAATACT  ACTACGTCAC  ACCAGTTACT     1140
TTTCGGTTTT  GGCTCTCCCA  TTGTGCAATC  GGTGTTATTT  GATGGCTGCA  TGCTTGATAT     1200
TGAAAAAGAT  GACTATGGTT  TTGTTTGGTC  TTGTCTCTCA  AATGAAAATG  GGGACTATTG     1260
CAAGGGGCTC  TACAAACCCC  GTTTTTCACA  AGGGGTATCC  CCGAACTGGC  CGATGTGCGA     1320
CTTGTCCGGA  GCATCTGCAG  AGCGCTGCAT  TTATCCTTAT  TGCCCTGAGG  GGGAAGAGTG     1380
CGTTCCCTTA  CCACCTTCAC  CGCCCAGTGA  TTCCCTGTT   GATGGGCTGA  GCAGCTCGTT     1440
TAAGTCTGCG  TTCAATCAGG  TCTATAAAAA  CCAATCAGAG  ATGGCTTCGA  CTCTCAATCA     1500
TGTCAGTGGT  CAGGTGTCCC  ACTCTCAAGA  TATGGTTCAG  CTCAATACGA  AGTTTCACGC     1560
GGATCGTGTT  CTTGAGAGTG  TCACCGCAGT  CAACAATCGT  TTGGGTGGGC  AAATGGAGTA     1620
TCTTGAGGAA  ATCCGCATTG  ATGTTTGGGA  TACGCAACGG  GAGGTAAGAA  AAGCCAAGGA     1680
TGAGCTTTAC  TCTCGTGTTG  CGGCTGTTTC  ATACGATGTG  CTTTATAGCG  AGCTTAATGT     1740
CCTTCGGGCG  ATTGATGAAC  TTAAAGACTC  ACTCGGTGGG  ACTGTCGTTC  CGCCTAACCC     1800
AGACCAACCC  AATCCCACGC  CACCCGATAG  CAGCAGCCCC  AATTATACAG  GGGCGCTTAA     1860
TACCATCTCT  AAAAAGCTCA  ATACCTTAGA  GACGATTTCA  CAGCAACTCG  ACACCATGAA     1920
CACGGCGCTA  TCAGGGCGCT  GTAGTAACCC  TGAACGCTGT  CAGTTTCCGA  TACGAGAGGC     1980
CGAGACCGAG  TTAGAAACGG  CTCAGCAGAA  TTTAAAGCAG  ATGATCAACG  AGAAAATCAC     2040
CCAGTCGGCT  TTGCATCAGT  TCAAAGGCTC  GGCGGCGGTG  CCTTCGTTTT  GCTCCTATGT     2100
CGAGGCGTTT  GGTTACAACC  TCTGTTTTGA  CTTCTCCCTC  TTTTCTGAAA  ACCTGCACAT     2160
CATCCGCATG  ATAGTGCTCG  CGATGGCGTA  CATTCTGGCC  GCCATGCTCA  TTTTGTTTAG     2220
GTGATGCTTA  TGATGGACAC  CCTTTATGAC  TGGCTAATTG  ATGGCTTTAC  GTGGCTTGTG     2280
ATCAAGCTCG  GTATTATGTG  GATTGAGAGC  AAGATTTTTG  TTATCCAATT  CTTCTGGGAG     2340
ATGTCCCAGA  AAGTGATTGA  TATGTTACC   ATCTATCCGC  TTATCCAACA  GGCTATCGAT     2400
ATGCTGCCTC  CTCAATACAG  CGGCTTTCTG  TTCTTTTTAG  GGTTAGACCA  AGCGCTGGCT     2460
ATCGTGCTTC  AGGCTTTGAT  GACCCGTTTT  GCCCTGCGAG  CGTTAAACCT  ATGAGTATCT     2520
TTATTCATCA  CGGCGCGCCA  GGCTCTTATA  AACGTCAGG   GGCATTATGG  CTTCGTCTGC     2580
TGCCGGCGAT  TAAGTCAGGC  CGTCACATCA  TCACGAATGT  GCGAGGCTTA  AACCTTGAAC     2640
GCATGGCTAA  GTACTTAAAA  ATGGATGTCT  CGGACATCAG  TATCGAGTTT  ATTGATACAG     2700
ACCATCCTGA  CGGTCGCTTA  ACGATGGCGC  GTTTTGGCA   CTGGGCGAGA  AAGGACGCGT     2760
TTCTCTTTAT  CGATGAATGT  GGTCGCATCT  GGCCGCCGAG  ACTGACGGTC  ACCAATTTAA     2820
AGGCGCTCGA  CACGCCGCCG  GATTGGTCG   CAGAGGATAG  GCCTGAGAGC  TTTGAGGTGG     2880
CTTTTGACAT  GCATCGTCAC  CACGGCTGGG  ATATC                                  2915
```

( 2 ) INFORMATION FOR SEQ ID NO:5:

( i ) SEQUENCE CHARACTERISTICS:
        ( A ) LENGTH: 291 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Vibrio cholerae
        ( B ) STRAIN: El Tor E7946

( v i i ) IMMEDIATE SOURCE:
        ( B ) CLONE: ace ( x i ) SEQUENCE DESCRIPTION: SEQ ID NO:5:

```
ATGCTTATGA TGGACACCCT TTATGACTGG CTAATTGATG GCTTTACGTG GCTTGTGATC        60
AAGCTCGGTA TTATGTGGAT TGAGAGCAAG ATTTTTGTTA TCCAATTCTT CTGGGAGATG       120
TCCCAGAAAG TGATTGATAT GTTTACCATC TATCCGCTTA TCCAACAGGC TATCGATATG       180
CTGCCTCCTC AATACAGCGG CTTTCTGTTC TTTTTAGGGT TAGACCAAGC GCTGGCTATC       240
GTGCTTCAGG CTTTGATGAC CCGTTTTGCC CTGCGAGCGT TAAACCTATG A                291
```

( 2 ) INFORMATION FOR SEQ ID NO:6:

( i ) SEQUENCE CHARACTERISTICS:
        ( A ) LENGTH: 1188 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Vibrio cholerae
        ( B ) STRAIN: El Tor E7946

( v i i ) IMMEDIATE SOURCE:
        ( B ) CLONE: orfU ( x i ) SEQUENCE DESCRIPTION: SEQ ID NO:6:

```
ATGCGCTATT TTCTACTGTT TTTGACATTG CTCTTTCTTT CTCCATCGGT AACGGCTTCC        60
GCCATCAATT GTGATCCTAA TACTACTACG TCACACCAGT TACTTTTCGG TTTTGGCTCT       120
CCCATTGTGC AATCGGTGTT ATTTGATGGC TGCATGCTTG ATATTGAAAA AGATGACTAT       180
GGTTTTGTTT GGTCTTGTCT CTCAAATGAA AATGGGGACT ATTGCAAGGG GCTCTACAAA       240
CCCCGTTTTT CACAAGGGGT ATCCCCGAAC TGGCCGATGT GCGACTTGTC CGGAGCATCT       300
GCAGAGCGCT GCATTTATCC TTATTGCCCT GAGGGGAAG AGTGCGTTCC CTTACCACCT        360
TCACCGCCCA GTGATTCCCC TGTTGATGGG CTGAGCAGCT CGTTTAAGTC TGCGTTCAAT       420
CAGGTCTATA AAAACCAATC AGAGATGGCT TCGACTCTCA ATCATGTCAG TGGTCAGGTG       480
TCCCACTCTC AAGATATGGT TCAGCTCAAT ACGAAGTTTC ACGCGGATCG TGTTCTTGAG       540
AGTGTCACCG CAGTCAACAA TCGTTTGGGT GGGCAAATGG AGTATCTTGA GGAAATCCGC       600
ATTGATGTTT GGGATACGCA ACGGGAGGTA AGAAAAGCCA AGGATGAGCT TTACTCTCGT       660
```

-continued

| | | | | | |
|---|---|---|---|---|---|
| GTTGCGGCTG | TTTCATACGA | TGTGCTTTAT | AGCGAGCTTA | ATGTCCTTCG | GGCGATTGAT | 720 |
| GAACTTAAAG | ACTCACTCGG | TGGGACTGTC | GTTCCGCCTA | ACCCAGACCA | ACCCAATCCC | 780 |
| ACGCCACCCG | ATAGCAGCAG | CCCCAATTAT | ACAGGGGCGC | TTAATACCAT | CTCTAAAAAG | 840 |
| CTCAATACCT | TAGAGACGAT | TTCACAGCAA | CTCGACACCA | TGAACACGGC | GCTATCAGGG | 900 |
| CGCTGTAGTA | ACCCTGAACG | CTGTCAGTTT | CCGATACGAG | AGGCCGAGAC | CGAGTTAGAA | 960 |
| ACGGCTCAGC | AGAATTTAAA | GCAGATGATC | AACGAGAAAA | TCACCCAGTC | GGCTTTGCAT | 1020 |
| CAGTTCAAAG | GCTCGGCGGC | GGTGCCTTCG | TTTTGCTCCT | ATGTCGAGGC | GTTTGGTTAC | 1080 |
| AACCTCTGTT | TTGACTTCTC | CCTCTTTTCT | GAAAACCTGC | ACATCATCCG | CATGATAGTG | 1140 |
| CTCGCGATGG | CGTACATTCT | GGCCGCCATG | CTCATTTTGT | TTAGGTGA | | 1188 |

(2) INFORMATION FOR SEQ ID NO:7:

(i) SEQUENCE CHARACTERISTICS:
        (A) LENGTH: 1428 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (v) ORIGINAL SOURCE:
        (A) ORGANISM: Vibrio cholerae
        (B) STRAIN: El Tor E7946

(vii) IMMEDIATE SOURCE:
        (B) CLONE: zot (xi) SEQUENCE DESCRIPTION: SEQ ID NO:7:

| | | | | | |
|---|---|---|---|---|---|
| ATACAGCGGC | TTTCTGTTCT | TTTTAGGGTT | AGACCAAGCG | CTGGCTATCG | TGCTTCAGGC | 60 |
| TTTGATGACC | CGTTTCGCCC | TGCGAGCGTT | AAACCTATGA | GTATCTTTAT | TCATCACGGC | 120 |
| GCGCCAGGCT | CTTATAAAAC | GTCCGGGGCA | TTATGGCTTC | GTCTGCTGCC | GGCGATTAAG | 180 |
| TCAGGCCGTC | ACATCATCAC | GAATGTGCGA | GGCTTAAACC | TTGAACGCAT | AGCTAAGTAC | 240 |
| TTAAAAATGG | ACGTCTCAGA | CATCAGTATC | GAGTTTATTG | ATACAGACCA | TCCAGACGGT | 300 |
| CGCTTAACGA | TGGCGCGTTT | TTGGCACTGG | GCGAGAAAGG | ACGCGTTTCT | CTTTATTGAT | 360 |
| GAATGTGGTC | GCATCTGGCC | GCCGAGACTG | ACGGCCACCA | ATTTAAAGGC | GCTCGACACG | 420 |
| CCGCCGGATT | TGGTCGCAGA | GGATAGGCCT | GAGAGCTTTG | AGGTCGCTTT | TGACATGCAT | 480 |
| CGTCACCACG | GCTGGGATAT | CTGCCTAACC | ACGCCTAACA | TTGCCAAAGT | GCACAACATG | 540 |
| ATAAGAGAGG | CGGCGGAGAT | AGGCTATCGC | CACTTTAACC | GCGCCACGGT | GGGGCTAGGG | 600 |
| GCAAAGTTTA | CCCTGACCAC | CCACGATGCA | GCCAACTCTG | GACAGATGGA | TTCGCACGCG | 660 |
| CTGACACGCC | AAGTCAAAAA | AATTCCAAGT | CCGATTTTTA | AGATGTACGC | AAGCACCACC | 720 |
| ACAGGCAAAG | CACGCGACAC | GATGGCCGGA | ACGGCGCTGT | GGAAAGACAG | AAAGATCCTT | 780 |
| TTCTTGTTCG | GCATGGTTTT | TTTGATGTTC | TCTTATTCGT | TTTACGGCTT | ACACGACAAT | 840 |
| CCAATTTTTA | CAGGGGGAAA | TGATGCAACT | ATCGAGTCAG | AGCAATCCGA | GCCTCAGTCA | 900 |
| AAGGCTACTG | CTGGGAATGC | TGTCGGGAGC | AAGGCGGCTG | CTCCTGCGTC | TTTTGGTTTT | 960 |
| TGTATTGGTC | GGCTTTGTGT | CCAAGATGGT | TTTGTCACTG | TTGGTGATGA | GCGTTATCGC | 1020 |
| CTCGTAGACA | ATTTGGACAT | TCCTTATCGT | GGTCTATGGG | CGACAGGTCA | TCACATTTAC | 1080 |
| AAGGATACGC | TTACAGTGTT | TTTTGAAACC | GAGAGTGGCA | GCGTCCCAAC | AGAGCTGTTT | 1140 |

```
GCATCGAGCT  ACCGCTACAA  GGTGCTACCG  TTACCGGATT  TCAATCACTT  TGTGGTGTTC    1200

GATACCTTTG  CAGCGCAAGC  GCTGTGGGTA  GAAGTGAAAC  GGGGTTTACC  GATAAAAACA    1260

GAAAATGATA  AAAAGGACT   AAATAGTATA  TTTTGATTTT  TGATTTTTGA  TTTTTGATTT    1320

TTGATTTTTG  ATTTTTGATT  TTTGATTTCA  AATAATACAA  ATTTATTTAC  TTATTTAATT    1380

GTTTTGATCA  ATTATTTTTC  TGTTAAACAA  AGGGAGCATT  ATATGGTA                  1428
```

(2) INFORMATION FOR SEQ ID NO:8:

(i) SEQUENCE CHARACTERISTICS:
        (A) LENGTH: 400 amino acids
        (B) TYPE: amino acid
        (C) STRANDEDNESS:
        (D) TOPOLOGY: linear (ii) MOLECULE TYPE: peptide (iii) HYPOTHETICAL: NO (iv) ANTI-SENSE: NO (vi) ORIGINAL SOURCE:
        (A) ORGANISM: Vibrio cholerae
        (B) STRAIN: El Tor 7946

(vii) IMMEDIATE SOURCE:
        (B) CLONE: zot (xi) SEQUENCE DESCRIPTION: SEQ ID NO:8:

```
Met  Ser  Ile  Phe  Ile  His  His  Gly  Ala  Pro  Gly  Ser  Tyr  Lys  Thr  Ser
 1              5                        10                       15

Gly  Ala  Leu  Asn  Leu  Arg  Leu  Leu  Pro  Ala  Ile  Lys  Ser  Gly  Arg  His
             20                       25                       30

Ile  Ile  Thr  Asn  Val  Arg  Gly  Leu  Asn  Leu  Glu  Arg  Ile  Ala  Lys  Tyr
         35                       40                       45

Leu  Lys  Met  Asp  Val  Ser  Asp  Ile  Ser  Ile  Glu  Phe  Ile  Asp  Thr  Asp
     50                       55                       60

His  Pro  Asp  Gly  Arg  Leu  Thr  Met  Ala  Arg  Phe  Trp  His  Trp  Ala  Arg
 65                       70                       75                       80

Lys  Asp  Ala  Phe  Leu  Phe  Ile  Asp  Glu  Cys  Gly  Arg  Ile  Asn  Pro  Pro
                  85                       90                       95

Arg  Leu  Thr  Ala  Thr  Asn  Leu  Lys  Ala  Leu  Asp  Thr  Pro  Pro  Asp  Leu
             100                      105                      110

Val  Ala  Glu  Asp  Arg  Pro  Glu  Ser  Pro  Glu  Val  Ala  Phe  Asp  Met  His
             115                      120                      125

Arg  His  His  Gly  Trp  Asp  Ile  Cys  Leu  Thr  Thr  Pro  Asn  Ile  Ala  Lys
         130                      135                      140

Val  His  Asn  Met  Ile  Arg  Glu  Ala  Ala  Glu  Ile  Gly  Tyr  Arg  His  Phe
145                      150                      155                      160

Asn  Arg  Ala  Thr  Val  Gly  Leu  Gly  Ala  Lys  Phe  Thr  Leu  Thr  Ile  His
                  165                      170                      175

Asp  Ala  Ala  Asn  Ser  Gly  Gln  Met  Asp  Ser  His  Ala  Leu  Thr  Arg  Gln
             180                      185                      190

Val  Lys  Lys  Ile  Pro  Ser  Pro  Ile  Phe  Lys  Met  Tyr  Ala  Ser  Thr  Thr
             195                      200                      205

Thr  Gly  Lys  Ala  Arg  Asp  Thr  Met  Ala  Gly  Thr  Ala  Leu  Trp  Lys  Asp
     210                      215                      220

Arg  Lys  Ile  Leu  Phe  Leu  Phe  Gly  Met  Val  Phe  Leu  Met  Phe  Ser  Tyr
225                      230                      235                      240

Ser  Phe  Tyr  Gly  Leu  His  Asp  Asn  Pro  Ile  Phe  Thr  Gly  Gly  Asn  Asp
```

|     |     |     |     | 245 |     |     |     | 250 |     |     |     | 255 |     |     |
|---|---|---|---|---|---|---|---|---|---|---|---|---|---|---|
| Ala | Thr | Ile | Glu 260 | Ser | Glu | Gln | Ser | His 265 | Pro | Gln | Ser | Lys | Ala 270 | Thr | Ala |
| Gly | Asn | Ala 275 | Val | Gly | Ser | Lys | Ala | Ala 280 | Ala | Pro | Ala | Ser 285 | Phe | Gly | Phe |
| Cys | Ile 290 | Gly | Arg | Leu | Cys 295 | Val | Gln | Asp | Gly | Phe | Val 300 | Thr | Val | Gly | Asp |
| Glu 305 | Arg | Tyr | Arg | Leu | Val 310 | Asp | Asn | Leu | Asp | Ile 315 | Pro | Tyr | Arg | Gly | Leu 320 |
| Trp | Ala | Thr | Gly | His 325 | His | Ile | Tyr | Lys | Asp 330 | Thr | Leu | Thr | Val | Phe 335 | Phe |
| Glu | Thr | Glu | Ser 340 | Gly | Ser | Val | Pro | Thr 345 | Glu | Leu | Phe | Ala | Ser 350 | Ser | Tyr |
| Arg | Tyr | Lys 355 | Val | Leu | Pro | Leu | Pro 360 | Asp | Phe | Asn | His | Phe 365 | Val | Val | Phe |
| Asp | Thr 370 | Phe | Ala | Ala | Gln | Ala 375 | Leu | Trp | Val | Glu | Val 380 | Lys | Arg | Gly | Leu |
| Pro 385 | Ile | Lys | Thr | Glu | Asn 390 | Asp | Asp | Lys | Lys | Gly 395 | Leu | Asn | Ser | Ile | Phe 400 |

( 2 ) INFORMATION FOR SEQ ID NO:9:

( i ) SEQUENCE CHARACTERISTICS:
        ( A ) LENGTH: 12 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Vibrio cholerae
        ( B ) STRAIN: classical 395

( v i i ) IMMEDIATE SOURCE:
        ( B ) CLONE: XbaI site at end of A subunit 550 bp fragment ( x i ) SEQUENCE DESCRIPTION: SEQ ID NO:9:

GATTCTAGAC CT                                              12

( 2 ) INFORMATION FOR SEQ ID NO:10:

( i ) SEQUENCE CHARACTERISTICS:
        ( A ) LENGTH: 12 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Vibrio cholerae
        ( B ) STRAIN: classical 395

( v i i ) IMMEDIATE SOURCE:
        ( B ) CLONE: ClaI site at end of 550 bp fragment of the A
                subunit ( x i ) SEQUENCE DESCRIPTION: SEQ ID NO:10:

TCATCGATGA GT 12

(2) INFORMATION FOR SEQ ID NO:11:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
        (A) ORGANISM: Vibrio cholerae
        (B) STRAIN: classical 395

(vii) IMMEDIATE SOURCE:
        (B) CLONE: amino acid sequence of region containing XbaI
            site (xi) SEQUENCE DESCRIPTION: SEQ ID NO:11:

Asp Ser Arg Pro
1

(2) INFORMATION FOR SEQ ID NO:12:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
        (A) ORGANISM: Vibrio cholerae
        (B) STRAIN: classical 395

(vii) IMMEDIATE SOURCE:
        (B) CLONE: amino acid sequence of ClaI site (xi) SEQUENCE DESCRIPTION: SEQ ID NO:12:

Ser Ser Met Ser
1

(2) INFORMATION FOR SEQ ID NO:13:

(i) SEQUENCE CHARACTERISTICS:
        (A) LENGTH: 15 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Vibrio cholerae
        (B) STRAIN: classical 395

-continued ( v i i ) IMMEDIATE SOURCE:
    ( B ) CLONE: CVD101- deletion junction +XbaI linker ( x i ) SEQUENCE DESCRIPTION: SEQ ID NO:13:

GATTCTAGAG CGATG                                                                15

( 2 ) INFORMATION FOR SEQ ID NO:14:

( i ) SEQUENCE CHARACTERISTICS:
        ( A ) LENGTH: 5 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
        ( A ) ORGANISM: Vibrio cholerae
        ( B ) STRAIN: classical 395

( v i i ) IMMEDIATE SOURCE:
        ( B ) CLONE: CVD101-amino acid sequence at deletion
            junction ( x i ) SEQUENCE DESCRIPTION: SEQ ID NO:14:

Asp  Ser  Arg  Ala  Met
    1                    5

( 2 ) INFORMATION FOR SEQ ID NO:15:

( i ) SEQUENCE CHARACTERISTICS:
        ( A ) LENGTH: 395 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
        ( A ) ORGANISM: Vibrio cholerae
        ( B ) STRAIN: classical 395

( v i i ) IMMEDIATE SOURCE:
        ( B ) CLONE: orfU protein ( x i ) SEQUENCE DESCRIPTION: SEQ ID NO:15:

Met  Arg  Tyr  Phe  Leu  Leu  Phe  Leu  Thr  Leu  Leu  Phe  Leu  Ser  Pro  Ser
    1                   5                        10                       15

Val  Thr  Ala  Ser  Ser  Ile  Asn  Cys  Asp  Pro  Asn  Thr  Thr  Thr  Ser  His
                        20                       25                       30

Gln  Leu  Leu  Phe  Gly  Phe  Gly  Ser  Pro  Ile  Val  Gln  Ser  Val  Leu  Phe
                   35                       40                       45

Asp  Gly  Cys  Met  Leu  Asp  Ile  Glu  Lys  Asp  Asp  Tyr  Gly  Phe  Val  Trp
              50                       55                       60

Ser  Cys  Leu  Ser  Asn  Glu  Asn  Gly  Asp  Tyr  Cys  Lys  Gly  Leu  Tyr  Lys
    65                       70                       75                       80

Pro  Arg  Phe  Thr  Gln  Gly  Val  Ser  Pro  Asn  Trp  Pro  Met  Cys  Asp  Leu
                        85                       90                       95

Ser  Gly  Ala  Ser  Ala  Glu  Arg  Cys  Ile  Tyr  Pro  Tyr  Cys  Pro  Glu  Gly

|     |     |     |     | 100 |     |     |     | 105 |     |     |     | 110 |     |     |
|-----|-----|-----|-----|-----|-----|-----|-----|-----|-----|-----|-----|-----|-----|-----|
| Glu | Glu | Cys<br>115 | Val | Pro | Leu | Pro | Pro<br>120 | Ser | Pro | Pro | Ser | Asp<br>125 | Ser | Pro | Val |
| Asp | Gly<br>130 | Leu | Ser | Ser | Ser | Phe<br>135 | Lys | Ser | Ala | Phe | Asn<br>140 | Gln | Val | Tyr | Lys |
| Asn<br>145 | Gln | Ser | Glu | Met | Ala<br>150 | Ser | Thr | Leu | Asn | His<br>155 | Val | Ser | Gly | Gln | Val<br>160 |
| Ser | His | Ser | Gln | Asp<br>165 | Met | Val | Gln | Leu | Asn<br>170 | Thr | Lys | Phe | His | Ala<br>175 | Asp |
| Arg | Val | Leu | Glu<br>180 | Lys | Val | Asn | Ala | Ile<br>185 | Asn | Asn | Arg | Leu | Asn<br>190 | Gly | Gln |
| Ile | Asn | Tyr<br>195 | Leu | Glu | Glu | Val | Arg<br>200 | Ile | Asp | Val | Trp | Asp<br>205 | Thr | Gln | Arg |
| Glu | Val | Arg<br>210 | Lys | Ala | Lys | Asp<br>215 | Glu | Leu | Ser | Ser | Arg<br>220 | Val | Gly | Ser | Val |
| Ala<br>225 | His | Asp | Val | Tyr | Gln<br>230 | Ser | Lys | Asn | Ala | Val<br>235 | Leu | Arg | Ala | Ile | Asp<br>240 |
| Glu | Leu | Lys | Asp | Ser<br>245 | Leu | Gly | Gly | Val | Val<br>250 | Val | Pro | Pro | Asn | Pro<br>255 | Asp |
| Gln | Pro | Asn | Pro<br>260 | Thr | Pro | Pro | Asp | Ser<br>265 | Ser | Ser | Pro | Asn | Tyr<br>270 | Thr | Gly |
| Ala | Leu | Asn<br>275 | Thr | Ile | Ser | Lys | Lys<br>280 | Leu | Asn | Thr | Leu | Glu<br>285 | Thr | Ile | Ser |
| Gln | Gln<br>290 | Leu | Asp | Thr | Met | Asn<br>295 | Thr | Ala | Leu | Ser | Gly<br>300 | Arg | Cys | Ser | Asn |
| Pro<br>305 | Ala | Arg | Cys | Gln | Phe<br>310 | Pro | Ile | Arg | Glu | Ala<br>315 | Glu | Thr | Glu | Leu | Glu<br>320 |
| Thr | Ala | Gln | Gln | Asn<br>325 | Leu | Lys | Gln | Met | Ile<br>330 | Asn | Asp | Lys | Ile | Thr<br>335 | Gln |
| Ser | Ala | Leu | His<br>340 | Gln | Phe | Lys | Gly | Ser<br>345 | Ala | Ala | Val | Pro | Ser<br>350 | Phe | Cys |
| Ser | Tyr | Val<br>355 | Glu | Glu | Phe | Gly | Tyr<br>360 | Asn | Leu | Cys | Phe | Asp<br>365 | Phe | Ser | Leu |
| Phe | Ser<br>370 | Glu | Asn | Leu | His | Ile<br>375 | Ile | Arg | Met | Ile | Val<br>380 | Leu | Ala | Met | Ala |
| Tyr<br>385 | Ile | Leu | Ala | Ala | Met<br>390 | Leu | Ile | Leu | Phe | Arg<br>395 |     |     |     |     |     |

( 2 ) INFORMATION FOR SEQ ID NO:16:

( i ) SEQUENCE CHARACTERISTICS:
        ( A ) LENGTH: 95 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
        ( A ) ORGANISM: Vibrio cholerae
        ( B ) STRAIN: classical 395

( v i i ) IMMEDIATE SOURCE:
        ( B ) CLONE: ace protein ( x i ) SEQUENCE DESCRIPTION: SEQ ID NO:16:

-continued

| Met 1 | Leu | Met | Met | Asp 5 | Pro | Leu | Tyr | Asp | Trp 10 | Leu | Ile | Asp | Gly | Phe 15 | Thr |
| Trp | Leu | Val | Ile 20 | Lys | Leu | Gly | Ile | Met 25 | Trp | Ile | Glu | Ser | Lys 30 | Ile | Phe |
| Val | Ile | Gln 35 | Phe | Phe | Trp | Glu | Met 40 | Ser | Gln | Lys | Val | Ile 45 | Asp | Met | Phe |
| Thr | Ile 50 | Tyr | Pro | Leu | Ile | Gln 55 | Gln | Ala | Ile | Asp | Met 60 | Leu | Ser | Pro | Gln |
| Tyr 65 | Ser | Gly | Phe | Leu | Phe 70 | Phe | Leu | Gly | Leu | Asp 75 | Gln | Ala | Leu | Ala | Ile 80 |
| Val | Leu | Gln | Ala | Leu 85 | Met | Thr | Arg | Phe | Ala 90 | Leu | Arg | Ala | Leu | Asn 95 | |